US007630790B2

(12) United States Patent
Handfield et al.

(10) Patent No.: US 7,630,790 B2
(45) Date of Patent: Dec. 8, 2009

(54) MEDICAMENT INVENTORY SYSTEM AND METHOD

(76) Inventors: Michael Handfield, 910 Sherwood Ct., Rochester Hills, MI (US) 48307; Helene Laliberte, 910 Sherwood Ct., Rochester Hills, MI (US) 48307

( * ) Notice: Subject to any disclaimer, the term of this patent is extended or adjusted under 35 U.S.C. 154(b) by 188 days.

(21) Appl. No.: 11/056,521

(22) Filed: Feb. 11, 2005

(65) Prior Publication Data
US 2006/0058918 A1 Mar. 16, 2006

Related U.S. Application Data

(63) Continuation of application No. 10/939,620, filed on Sep. 13, 2004, now Pat. No. 7,080,755.

(51) Int. Cl.
*G06F 17/00* (2006.01)
(52) U.S. Cl. .................. 700/236; 700/237; 700/241
(58) Field of Classification Search .................. 700/236
See application file for complete search history.

(56) References Cited

U.S. PATENT DOCUMENTS

| 3,227,127 | A |   | 1/1966  | Gayle            |         |
|-----------|---|---|---------|------------------|---------|
| 3,248,156 | A |   | 4/1966  | Repko            |         |
| 3,586,208 | A | * | 6/1971  | Hussey           | 221/299 |
| 3,604,562 | A |   | 9/1971  | Loeffler         |         |
| 3,762,601 | A |   | 10/1973 | Mc Laughlin      |         |
| 3,830,411 | A |   | 8/1974  | Krechmar         |         |
| 4,018,358 | A |   | 4/1977  | Johnson et al.   |         |
| 4,207,992 | A |   | 6/1980  | Brown            |         |
| 4,360,125 | A |   | 11/1982 | Martindale et al.|         |
| 4,437,579 | A |   | 3/1984  | Obland           |         |
| 4,483,626 | A |   | 11/1984 | Noble            |         |
| 4,504,153 | A |   | 3/1985  | Schollmeyer et al.|        |

(Continued)

FOREIGN PATENT DOCUMENTS

EP          0 050 423   A1    4/1982

(Continued)

OTHER PUBLICATIONS

Buerger, D., "Medication Management in Assisted Living: Pharmacy Rises to the Challenge", American Society of Consultant Pharmacists, Inc., 1998, [online] [retrieved on Mar. 11, 2004]. Retrieved from the Internet: URL:http://www.ascp.com/public/pubs/tcp/1998/jun/medmng.shtml.

(Continued)

*Primary Examiner*—Gene Crawford
*Assistant Examiner*—Timothy R Waggoner
(74) *Attorney, Agent, or Firm*—Morrison & Foerster LLP

(57) ABSTRACT

The invention relates to a method and system that utilizes one or more cassettes or trays, which hold one or more types of medicaments, the cassettes or trays being configured for intelligent dispensing of the medicaments. In one embodiment, a smart tray for dispensing medicaments includes: a housing; an information storage device that maintains inventory information regarding medicament units in the tray; and a communication device to transfer the inventory information between the information storage device and an external computing apparatus to facilitate inventory maintenance. In a further embodiment, the smart tray includes a mechanism to determine a quantity of medicament units dispensed from the tray to facilitate inventory tracking.

32 Claims, 28 Drawing Sheets

U.S. PATENT DOCUMENTS

| | | | |
|---|---|---|---|
| 4,526,474 A | 7/1985 | Simon | |
| 4,546,901 A | 10/1985 | Buttarazzi | |
| 4,573,606 A | 3/1986 | Lewis et al. | |
| 4,616,316 A | 10/1986 | Hanpeter et al. | |
| 4,617,557 A | 10/1986 | Gordon | |
| 4,626,105 A | 12/1986 | Miller | |
| 4,664,289 A | 5/1987 | Shimizu et al. | |
| 4,674,651 A | 6/1987 | Scidmore et al. | |
| 4,674,652 A | 6/1987 | Aten et al. | |
| 4,695,954 A | 9/1987 | Rose et al. | |
| 4,725,997 A | 2/1988 | Urquhart et al. | |
| 4,732,411 A | 3/1988 | Siegel | |
| 4,733,362 A | 3/1988 | Haraguchi | |
| 4,733,797 A | 3/1988 | Haber | |
| 4,785,969 A | 11/1988 | McLaughlin | |
| 4,811,764 A * | 3/1989 | McLaughlin | 221/2 |
| 4,823,982 A | 4/1989 | Aten et al. | |
| 4,835,372 A | 5/1989 | Gombrich et al. | |
| 4,839,806 A | 6/1989 | Goldfischer et al. | |
| 4,847,764 A | 7/1989 | Halvorson | |
| 4,857,713 A | 8/1989 | Brown | |
| 4,857,716 A | 8/1989 | Gombrich et al. | |
| 4,869,394 A | 9/1989 | Hurst | |
| 4,911,327 A | 3/1990 | Shepherd et al. | |
| 4,939,705 A | 7/1990 | Hamilton et al. | |
| 4,953,745 A | 9/1990 | Rowlett, Jr. | |
| 4,967,928 A | 11/1990 | Carter | |
| 4,971,221 A | 11/1990 | Urquhart et al. | |
| 4,984,709 A | 1/1991 | Weinstein | |
| 5,014,875 A | 5/1991 | McLaughlin et al. | |
| 5,047,948 A | 9/1991 | Turner | |
| 5,088,056 A | 2/1992 | McIntosh et al. | |
| 5,099,463 A | 3/1992 | Lloyd et al. | |
| 5,176,285 A | 1/1993 | Shaw | |
| 5,181,189 A | 1/1993 | Hafner | |
| 5,208,762 A | 5/1993 | Charhut et al. | |
| 5,213,232 A | 5/1993 | Kraft et al. | |
| 5,233,571 A | 8/1993 | Wirtschafter | |
| 5,272,318 A | 12/1993 | Gorman | |
| 5,289,157 A | 2/1994 | Rudick et al. | |
| 5,313,439 A | 5/1994 | Albeck | |
| 5,337,919 A | 8/1994 | Spaulding et al. | |
| 5,347,453 A | 9/1994 | Maestre | |
| 5,348,061 A | 9/1994 | Riley et al. | |
| 5,392,952 A | 2/1995 | Bowden | |
| 5,401,059 A | 3/1995 | Ferrario | |
| 5,405,048 A | 4/1995 | Rogers et al. | |
| 5,408,443 A | 4/1995 | Weinberger | |
| 5,412,372 A | 5/1995 | Parkhurst et al. | |
| 5,431,299 A | 7/1995 | Brewer et al. | |
| 5,460,294 A | 10/1995 | Williams | |
| 5,472,113 A | 12/1995 | Shaw | |
| 5,480,062 A | 1/1996 | Rogers et al. | |
| 5,502,944 A | 4/1996 | Kraft et al. | |
| 5,508,499 A | 4/1996 | Ferrario | |
| 5,522,525 A | 6/1996 | McLaughlin et al. | |
| 5,593,267 A | 1/1997 | McDonald et al. | |
| 5,609,268 A | 3/1997 | Shaw | |
| 5,623,242 A | 4/1997 | Dawson, Jr. et al. | |
| 5,657,236 A | 8/1997 | Conkright | |
| 5,671,592 A | 9/1997 | Yuyama et al. | |
| RE35,743 E | 3/1998 | Pearson | |
| 5,745,366 A | 4/1998 | Higham et al. | |
| 5,755,357 A | 5/1998 | Orkin et al. | |
| 5,826,217 A | 10/1998 | Lerner | |
| 5,852,590 A | 12/1998 | De La Huerga | |
| 5,897,024 A | 4/1999 | Coughlin et al. | |
| 5,945,651 A | 8/1999 | Chorosinski et al. | |
| 6,021,918 A | 2/2000 | Dumont et al. | |
| 6,032,155 A | 2/2000 | De La Huerga | |
| 6,085,938 A | 7/2000 | Coughlin | |
| 6,169,707 B1 | 1/2001 | Newland | |
| 6,170,230 B1 | 1/2001 | Chudy et al. | |
| 6,219,587 B1 | 4/2001 | Ahlin et al. | |
| 6,253,953 B1 | 7/2001 | Ishizuka | |
| 6,259,654 B1 | 7/2001 | De La Huerga | |
| 6,263,259 B1 | 7/2001 | Bartur | |
| 6,317,390 B1 | 11/2001 | Cardoza | |
| 6,324,123 B1 | 11/2001 | Durso | |
| 6,332,100 B1 | 12/2001 | Sahai et al. | |
| 6,343,711 B1 | 2/2002 | Coughlin | |
| 6,349,848 B1 * | 2/2002 | Uema et al. | 221/6 |
| 6,380,858 B1 | 4/2002 | Yarin et al. | |
| 6,470,234 B1 * | 10/2002 | McGrady | 700/236 |
| 6,529,446 B1 | 3/2003 | De La Huerga | |
| 6,535,637 B1 | 3/2003 | Wootton et al. | |
| 6,539,281 B2 | 3/2003 | Wan et al. | |
| 6,554,157 B2 * | 4/2003 | Geltser et al. | 221/200 |
| 6,564,121 B1 | 5/2003 | Wallace et al. | |
| 6,592,005 B1 | 7/2003 | Coughlin et al. | |
| 6,601,729 B1 | 8/2003 | Papp | |
| 6,611,733 B1 * | 8/2003 | De La Huerga | 700/236 |
| 6,616,037 B2 | 9/2003 | Grimm et al. | |
| 6,625,952 B1 | 9/2003 | Chudy et al. | |
| 6,636,780 B1 | 10/2003 | Haitin et al. | |
| 6,652,455 B1 | 11/2003 | Kocher | |
| 6,722,525 B1 | 4/2004 | Boyer et al. | |
| 6,865,444 B2 | 6/2004 | Howard | |
| 6,771,174 B2 | 8/2004 | Broas | |
| 6,902,083 B1 * | 6/2005 | Michael et al. | 221/2 |
| 6,957,126 B2 | 10/2005 | Kim | |
| 6,968,876 B2 | 11/2005 | Yacko et al. | |
| 7,014,063 B2 * | 3/2006 | Shows et al. | 221/211 |
| 7,061,831 B2 | 6/2006 | De La Huerga | |
| 7,080,755 B2 | 7/2006 | Handfield et al. | |
| 7,118,006 B2 * | 10/2006 | Williams et al. | 700/236 |
| 7,151,982 B2 * | 12/2006 | Liff et al. | 700/241 |
| 7,194,333 B2 * | 3/2007 | Shoenfeld | 700/243 |
| 7,228,198 B2 | 6/2007 | Vollm et al. | |
| 7,440,817 B2 | 10/2008 | Fu | |
| 2001/0037216 A1 | 11/2001 | Oscar et al. | |
| 2002/0062175 A1 | 5/2002 | Lion | |
| 2002/0147526 A1 | 10/2002 | Siegel | |
| 2003/0034392 A1 | 2/2003 | Grimm et al. | |
| 2003/0036683 A1 | 2/2003 | Kehr et al. | |
| 2003/0099158 A1 | 5/2003 | De La Huerga | |
| 2003/0183642 A1 | 10/2003 | Kempker | |
| 2004/0122554 A1 | 6/2004 | Howard | |
| 2004/0140013 A1 | 7/2004 | Yacko et al. | |
| 2004/0164088 A1 | 8/2004 | Baranowski | |

FOREIGN PATENT DOCUMENTS

| | | |
|---|---|---|
| EP | 0 078 356 A1 | 5/1983 |
| EP | 0 115 989 A1 | 8/1984 |
| EP | 0 131 414 A2 | 1/1985 |
| EP | 0 115 989 B1 | 4/1986 |
| EP | 0 078 356 B1 | 11/1986 |
| EP | 0 239 173 A2 | 9/1987 |
| EP | 0 310 933 A2 | 4/1989 |
| EP | 0 311 229 A2 | 4/1989 |
| EP | 0 131 414 B1 | 12/1989 |
| EP | 0 360 456 A2 | 3/1990 |
| EP | 0 392 196 A1 | 10/1990 |
| EP | 0 538 159 A1 | 4/1993 |
| EP | 0 557 661 A1 | 9/1993 |
| EP | 0 800 869 A1 | 10/1997 |
| GB | 1400317 | 7/1975 |
| GB | 2 055 758 A | 3/1981 |
| GB | 2 275 123 A | 8/1994 |
| GB | 2 288 040 A | 10/1995 |
| WO | WO-95/25546 | 9/1995 |
| WO | WO-96/10240 | 4/1996 |
| WO | WO-00/22440 | 4/2000 |

| | | |
|---|---|---|
| WO | WO-01/12239 | 2/2001 |
| WO | WO-2004/012647 | 2/2004 |
| WO | WO-2004/065285 | 8/2004 |

OTHER PUBLICATIONS

Tassone, A., Pharm.D., & Tomecki, M., Pharm.D., "Medication Errors in the Community Pharmacy", Drug Store News TechEd Program No. 401-000-02-002-H01, Release Date: Jan. 30, 2002, [online] [retrieved on Mar. 11, 2004]. Retrieved from the Internet: URL:https://www.cedrugstorenews.com/userapp/lessons/lesson_view_detail.cfm?lessonuid=401%2D000%2D02%2D002%2DH01.

International Search Report for PCT/CA2005/001388, mailed on Jan. 3, 2006, 4 pages.

Non-Final Office Action for U.S. Appl. No. 11/445,408, mailed on Oct. 24, 2008, 7 pages.

Non-Final Office Action for U.S. Appl. No. 11/445,105, mailed on Sep. 22, 2008, 6 pages.

Addington, W., "President's Column - Why We Need a Systems Approach to Prevent Deadly Medical Errors", American College of Physicians-American Society of Internal Medicine ACP-ASIM Observer, Nov. 1999.

Alliance for Pharmaceutical Care, "America's Pharmacists . . . Improve Patient Care", [online] [retrieved on Mar. 11, 2004]. Retrieved from the Internet: URL: http://www.accp.com/position/paper11.pdf.

Alliance for Pharmaceutical Care, "Today's Pharmacist . . . the Patient's Partner in Medication Management", [online] [retrieved on Mar. 11, 2004]. Retrieved from the Internet: URL: http://www.ncspae.org/documents/NCSLbrochur.pdf.

American College of Clinical Pharmacy, "A Vision of Pharmacy's Future Roles, Responsibilities, and Manpower Needs in the United States", Pharmacotherapy 2000;20(8):991-1022.

American College of Clinical Pharmacy, "Evidence of the Value of the Pharmacist", [online] [retrieved on Mar. 11, 2004]. Retrieved from the Internet: URL: http://www.accp.com/position/paper6.pdf.

American College of Clinical Pharmacy, "Issues in Medication Use in the United States", [online] [retrieved on Mar. 11, 2004]. Retrieved from the Internet: URL: http://www.accp.com/position/paper8.pdf.

American College of Clinical Pharmacy, "Pharmacists' Services can Save Medicaid Billions Annually", [online] [retrieved on Mar. 11, 2004]. Retrieved from the Internet: URL: http://www.accp.com/position/paper9.pdf.

American Health Information Management Association, "Flow of Patient Health Information Inside and Outside the Healthcare Industry", [online] [retrieved on Mar. 11, 2004]. Retrieved from the Internet: URL: http://www.ahima.org/infocenter/current/patientflowchartweb.pdf.

American Society of Health-System Pharmacists, "ASHP Statement on the Pharmacist's Role in Primary Care", [online ] [retrieved on Mar. 11, 2004]. Retrieved from the Internet: URL: http://www.ashp.org/bestpractices/MedTherapy/Med%20Therapy%20&%20Patient%20Care%20Spec.%20Prac.%20Areas%20State.%20Phar.%20Role%20in%20Pri.%20Care.pdf.

Barker, K., PhD., Felkey, B., MS, Flynn, E., PhD & Carper, J., RPh, "White Paper on Automation in Pharmacy", The American Society of Consultant Pharmacists, Mar. 1998, [online] [retrieved on Mar. 11, 2004]. Retrieved from the Internet: URL: http://www.ascp.com/public/pubs/tcp/1998/mar/feature2.shtml.

Barrett, L., Ph.D., "Prescription Drug Use Among Persons Age 45+", AARP, Jun. 2002.

Barrett, M., Holmes, B. and McAuley, S., "Healthcare Unbound," Wholeview™ TechStrategy™ Research, Dec. 17, 2002 [online] [retrieved on Jul. 29, 2004]. Retrieved from the internet: URL: http://www.forrester.com/Research/PDF/0,5110,15452,00.pdf.

Bedell, S. MD; Jabbour, S. MD, MPH, Goldberg, R. PhD et. al, "Discrepancies in the Use of Medications -Their Extent and Predictors in an Outpatient Practice", Arch Intern Med. 2000;160:2129-2134.

Beers, M., M.D., & Berkow, R., M.D., Editors, "Section 1. Basics of Geriatric Care, Chapter 10. Pharmacy" in "The Merck Manual of Geriatrics", 2004, [online] [retrieved on Mar. 11, 2004]. Retrieved from the Internet: URL: http://www.merck.com/mrkshared/mm_geriatrics/home.jsp.

Beers, M., M.D., & Berkow, R., M.D., Editors, "Section 22. Clinical Pharmacology, Chapter 301. Factors Affecting Drug Response" in "The Merck Manual of Diagnosis and Therapy", 2004, [online] [retrieved on Mar. 11, 2004]. Retrieved from the Internet: URL: http://www.merck.com/mrkshared/mmanual/sections.jsp.

Beers, M., MD, Editor-in-Chief, "Section 2. Drugs, Chapter 9. Drugs and Aging" in "The Merck Manual - Second Home Edition", 2003, [online] [retrieved on Mar. 11, 2004]. Retrieved from the Internet: URL: http://www.merck.com/mrkshared/mmanual_home2/contents.jsp.

Beers, M., MD, Editor-in-Chief, "Section 2. Drugs, Chapter 11. Compliance With Drug Treatment" in "The Merck Manual - Second Home Edition", 2003, [online] [retrieved on Mar. 11, 2004]. Retrieved from the Internet: URL: http://www.merck.com/mrkshared/mmanual_home2/contents.jsp.

Bernstein, L., PharmD, "Pharmacist's Guide to Patient Monitoring", Power-Pak C.E. Program No. 424-000-02-006-H04, Published: May 1, 2002, [online] [retrieved on Mar. 11, 2004]. Retrieved from the Internet: URL: http://www.powerpak.com/print.asp?page=courses/2098/lesson.htm.

Bloom, D., "High-Tech Drug Packaging Can Boost Patient Compliance", Managed Care, Jun. 1997.

Borel, J.M. & Rascati, K.L., "Effect of an Automated, Nursing Unit-Based Drug-Dispensing Device on Medication Errors", Am J Health Syst Pharm, Sep. 1, 1995; 52(17), pp. 1875-1879.

Borfitz, D., "Dispense the Drugs you Prescribe?", Medical Economics, 2001;22:44.

Borfitz, D., "Make your practice more profitable", Medical Economics, 2001;1:106.

Buckley, M., M.P.P., "Improving Drug Prescribing Practices in the Outpatient Setting: A Market Analysis", California Healthcare Foundation, Oct. 2002, [online] [retrieved on Mar. 11, 2004]. Retrieved from the Internet: URL: http://www.chcf.org/documents/ihealth/improvingDrugPrescribing.pdf.

Buerger, D., "Medication Management in Assisted Living: Pharmacy Rises to the Challenge", American Society of Consultant Pharmacists, Inc., 1998, [online] [retrieved on Mar. 11, 2004]. Retrieved from the Internet: URL: http://www.ascp.com/public/pubs/tcp/1998/jun/medmng.shtml.

Carmichael, J, Pharm.D., FCCP, O'Connell, M., Pharm.D. et. al., "Collaborative Drug Therapy Management by Pharmacists", Pharmacotherapy 1997;17(5):1050-1061.

Centers for Disease Control, "Profile of the Nation's Health - CDC Fact Book 2000/2001", [online] [retrieved on Mar. 11, 2004]. Retrieved from the Internet: URL: http://www.cdc.gov/maso/factbook/Fact%20Book.pdf.

Chervenak, L., "Medication Management: What's The Best Solution?", Assisted Living Success, Jun. 2001.

Cohen, J., "E-Diaries (Tap, Tap) Aid Drug Trials", New York Times, May 30, 2002.

Computer Sciences Corporation Life Sciences Practice "Alliancing Around E-Care", published in Pharmaceutical Visions, Apr. 2001, [online] [retrieved on Mar. 11, 2004]. Retrieved from the Internet: URL: http://www.csc.com/industries/healthservices/knowledgelibrary/uploads/785_1.pdf.

Computer Sciences Corporation Life Sciences Practice, "Life is a Trial", published in Scrip Magazine, Jan. 2001, [online] [retrieved on Mar. 11, 2004]. Retrieved from the Internet: URL: http://www.csc.com/industries/healthservices/knowledgelibrary/uploads/784_1.pdf.

Consumer Health Information Corporation. Several articles on its website (www.consumer-health.com) about drug advertising, patient education, patient compliance and behavior modification programs.

DeBor, G., "Finding the Good Stuff in the Healthcare Connectivity Bazaar", Apr. 2001, [online] [retrieved on Mar. 11, 2004]. Retrieved from the Internet: URL: http://www.csc.com/industries/healthservices/knowledgelibrary/uploads/783_1.pdf.

Erickson, A., "Point-of-Service: Combining Medical, Pharmaceutical Treatment", Pharmacy Today 8(6):11, 2002.

Ernst, F. & Grizzle, A., "Drug-Related Morbidity and Mortality: Updating the Cost-of-Illness Model", J Am Pharm Assoc 41(2):192-199, 2001.

FDA, "Combating Counterfeit Drugs: A Report Of The Food And Drug Administration" Feb. 18, 2004, [online] [retrieved on Apr. 14, 2004]. Retrieved from the internet: URL: http://www.fda.gov /oc/initiatives/counterfeit/report02 04. pdf.

Felkey, B. & Fox, B., "Monograph 18: Utilizing Internet Technologies to Expand Pharmacy-Based Patient Care Services", The American Pharmaceutical Association, (ACPE I.D. # 202- 000-01-175-H04) 2001.

First Consulting Group, "Crossing the Chasm with Information Technology: Bridging the Quality Gap in Health Care", California Healthcare Foundation, Jul. 2002, [online] [retrieved on Mar. 11, 2004]. Retrieved from the Internet: URL: http://www.chcf.org/documents/ihealth/CrossingChasmIT.pdf.

First Consulting Group, "E-Disease Management", California Healthcare Foundation, Nov. 2001, [online] [retrieved on Mar. 11, 2004]. Retrieved from the Internet: URL: http://www.chcf.org/documents/ihealth/EDiseaseManagement.pdf.

First Consulting Group, "E-Encounters", California Healthcare Foundation, Nov. 2001, [online] [retrieved on Mar. 11, 2004]. Retrieved from the Internet: URL: http://www.chcf.org/documents/hospitals/EEncounters.pdf.

First Consulting Group, "Rural Health Care Delivery: Connecting Communities Through Technology", California Healthcare Foundation, Dec. 2002, [online] [retrieved on Mar. 11, 2004]. Retrieved from the Internet: URL: http://www.chcf.org/documents/hospitals/RuralHealthCareDelivery.pdf.

First Consulting Group, "Using Computerized Registries in Chronic Disease Care", California Healthcare Foundation, Feb. 2004. [online] [retrieved on Mar. 11, 2004]. Retrieved from the Internet: URL: http://www.chcf.org/documents/chronicdisease/ComputerizedRegistriesInChronicDisease.pdf.

Fisher, J., "Robot Rx: Filling the Pharmaceutical Gap", Raleigh News & Observer, Jan. 20, 2004.

Fleck, C., "Nursing Home Care Is Found Wanting", AARP Bulletin Online, Apr. 2002, [online] [retrieved on Mar. 11, 2004]. Retrieved from the Internet: URL: http://www.aarp.org/bulletin/yourhealth/Articles/a2003-06-23-nursinghome.html.

Fordahl, M., "Seeking High-Tech Solutions for Seniors - Companies are Developing Sensors and Appliances that Enable the Elderly to Continue Living Independently", Los Angeles Times, Sep. 15, 2003, p. C.2.

Foundation for Managed Care Pharmacy, Inc, "The Value of Pharmaceuticals and Managed Pharmaceutical Care", [online] [retrieved on Mar. 11, 2004]. Retrieved from the Internet: URL: http://www.fmcpnet.org/data/resource/updated_june2003.ppt.

Fox, C., "Tech Tools, Case Management Offer Remedy for Soaring Health Costs", San Antonio Business Journal, Aug. 30, 2002.

Gianutsos, G., RPh, PhD, JD, "Prescription Errors and Legal Responsibility", Power-Pak C.E. Program No. 424-000-02-028-H03, Published: Dec. 1, 2002, [online] [retrieved on Mar. 11, 2004]. Retrieved from the Internet: URL: http://www.powerpak.com/print.asp?page=courses/2434/lesson.htm.

Green, J., Pharm.D., FCP, "The EDC Value Proposition to the Pharmaceutical Industry", Datatrak International, Inc., Jul. 9, 2001, [online] [retrieved on Mar. 11, 2004]. Retrieved from the Internet: URL: http://www.datatraknet.com/valuepropositionofedc/ValuePropositionofEDC.pdf.

Haddad, C., "Fake Drugs, Real Disaster - As Operators Get More Canny, the FDA is Cracking Down on Counterfeit Medicine", Business Week Online, Feb 9, 2004.

Heffler, S., Smith, S., Keehan, S., Clemens, M., Zezza, M. & Truffer, C., "Health Spending Projections Through 2013", Health Affairs Web Exclusive, Feb. 11, 2004, [online] [retrieved on Mar. 11, 2004]. Retrieved from the Internet: URL: http://content.healthaffairs.org/cgi/reprint/hlthaff.w4.79v1.pdf2/10/04.

Hepler, C., "Medication-Use Process: Observations on the Conference: A Pharmacist's Perspective", Am J Health-Syst Pharm, vol. 57, Mar 15, 2000: 590-594.

Hoffman, J., Shah, N., Vermeulen, L., Hunkler, R. & Hontz, K., "Projecting Future Drug Expenditures-2004", Am J Health-Syst Pharm 61(2):145-158, 2004.

Holzman, M. & Hurwich, M., "It's Not Your Father's Pharmacy - How the Internet Will Reshape the Relationship Between Consumers, Doctors and Drug Manufacturers", Computer Science Corporation - CSC's Intersections Dec. 1999, [online] [retrieved on Mar. 11, 2004]. Retrieved from the Internet: URL: http://www.csc.com/industries/healthservices/knowledgelibrary/uploads/756_1.PDF.

Hope, J., "Come and Get It: Physicians Dispense Drugs as a Patient Convenience" Modern Physician, Aug. 1, 2001.

Institute for Safe Medication Practices, "Pharmacy Interventions Can Reduce Clinical Errors", ISMP Medication Safety Alert, Jun. 26, 2002.

Institute for Safe Medication Practices, "Survey of Automated Dispensing Shows Need for Practice Improvements and Safer System Design", ISMP Medication Safety Alert, Jun. 16, 1999.

Jackson, T, Phd, R.Ph., "Decreasing Medication Errors in the Community Pharmacy", Drug Store News C.E. Program No. 401-000-04-006-HOI, Release Date: May 14, 2004, [online] [retrieved on Jan. 11, 2005]. Retrieved from the internet: URL: https:/ /www.cedrugstorenews.com/userapp/lessons/iesson view ui.cfm?lessonuid=40 I%2DOOO%2D04%2DO06%2DHO1.

Johnson, A., "Why We Can't Wait to Implement Disease Management", Business and Health Oct. 15, 2003; 21.

Kaufman et al. "Recent Patterns of Medication Use in the Ambulatory Adult Population of the United States", JAMA Jan. 16, 2002 - vol. 287, No. 3, pp. 337-344.

Kohn, L.T., Corrigan, J.M. & Donaldson, M.S., eds. "To Err is Human. Building a Safer Health System", Committee on Quality of Health Care in America, Institute of Medicine. 1999.

Lash, S. & Harding, J., "Abandoned Prescriptions - A Quantitative Assessment of Their Cause", J Managed Care Pharm 1995: 1: 193-199.

Lee, R., "Physician Dispensing", Orthopedic Technology Review, vol. 2, No. 10, Nov. 2000.

Levy, S., "Physician Dispensing - What's Behind the New Surge in the Sale of Drugs by Doctors in Their Offices?", Drug Topics, Jan. 1, 2001.

McCartney, J., "Meds-O-Matic - The InstyMeds Vending Machine Allows Patients to Get Prescriptions Without Visiting the Pharmacist", Pioneer Press, Nov. 9, 2002.

McDonough, R. & Doucette, W., "Developing Collaborative Working Relationships Between Pharmacists and Physicians", Journal of the American Pharmaceutical Association, Sep./Oct. 2001 vol. 41, No. 5; 682-692.

Mercer Human Resource Consulting, "Navigating the Pharmacy Benefits Marketplace", California Healthcare Foundation, Jan. 2003, [online] [retrieved on Mar. 11, 2004] Retrieved from the Internet: URL: http://www.chcf.org/documents/hospitals/NavPharmBenefits.pdf.

MetLife Mature Market Institute, "The MetLife Market Survey of Assisted Living Costs", Oct. 2003, [online] [retrieved on Mar. 11, 2004] Retrieved from the Internet: URL: http://www.metlife.corn/WPSAssets/16670870001065792597V1F2003%20Assisted%20Living%20Survey.pdf.

MetLife Mature Market Institute, "The MetLife Market Survey of Nursing Home & Home Care Costs", Aug. 2003, [online] [retrieved on Mar. 11, 2004]. Retrieved from the Internet: URL: http://www.metlife.com/WPSAssets/22802718901060258447V1F2003%20NH%20HC%20Market%20survey.pdf.

Mintz, S., M.S., "Empowering the Caregiver", Drug Store News TechEd Program No. 401-000-03-024-H01, Release Date: Nov. 1, 2003, [online] [retrieved on Mar. 11, 2004]. Retrieved from the Internet: URL: https://www.cedrugstorenews.com/userapp/lessons/lesson_view_ui.cfm?lessonuid=401%2D000%2D03%2D024%2DH01.

Morgan, T., MD, "The Economic Impact of Wasted Prescription Medication in an Outpatient Population of Older Adults", The Journal of Family Practice, Sep. 2001, vol. 50, No. 9.

Muirhead, G., "M.D. Dispensing Goes On-Line, Opening New Links to R.Ph.s", Drug Topics, Feb. 19, 1996.

Muirhead, G., "Where Does the Time Go? - Exclusive New Drug Topics Survey of R.Ph.s Offers Some Clues", Drug Topics, Jun. 10, 1996.

Murray, M., PharmD, MPH, "Chapter 11. Automated Medication Dispensing Devices" in Shojania, K.G., Duncan, B.W. & McDonald, K.M., et al., eds., "Making Health Care Safer: A Critical Analysis of Patient Safety Practices. Evidence Report/Technology Assessment No. 43" (Prepared by the University of California at San Francisco-Stanford Evidence-based Practice Center under Contract No. 290-97-0013), Agency for Healthcare Research and Quality. Jul. 2001.

Nash, D., MD, MBA, Koenig, J. & Chatterton, M., PharmD., "Why the Elderly Need Individualized Pharmaceutical Care", Office of Health Policy and Clinical Outcomes, Thomas Jefferson University, Apr. 2000.

National Institute on Drug Abuse, "Research Report Series - Prescription Drugs, Abuse and Addiction", NIH Publication No. 01-4881, Jul. 2001.

Nichols-English, G, & Poirier, S., "Monograph 15: Monitoring Patient Adherence to Pharmaceutical Care Plans", The American Pharmaceutical Association, (ACPE I.D. # 202-000-00-158-H04) 2001.

Noffsinger, R. & Chin, S., RPh, "Improving the Delivery of Care and Reducing Healthcare Costs with the Digitization of Information", Journal of Healthcare Information Management, vol. 14, No. 2, Summer 2000, pp. 23-30.

O'Brien, M., Petrie, K. & Raeburn, J., "Adherence to Medication Regimes: Updating a Complex Medical Issue", Medical Care Review (1992), 49(4), 435-154.

Oh, Y., Mccombs, J., Cheng, R. & Johnson, K., "Pharmacist Time Requirements for Counseling in an Outpatient Pharmacy", Am J Health-Syst Pharm 59(23):2346-2355, 2002.

Page, D., "Is the Long-Distance Dispensing of Drugs the Remedy for Patients in Remote Areas?", Drug Topics, Mar. 6, 2000.

Pandya, S. & Coleman, B. "Caregiving and Long-Term Care", AARP Public Policy Institute, Dec. 2000.

Partnership for Solutions, "Chronic Conditions: Making the Case for Ongoing Care", Dec. 2002, [online] [retrieved on Mar. 11, 2004]. Retrieved from the Internet: URL: http://www.partnershipforsolutions.com/DMS/files/chronicbook2002.pdf.

Partnership for Solutions, "Disease Management and Multiple Chronic Conditions", [online] [retrieved on Mar. 11, 2004]. Retrieved from the Internet: URL: http://www.partnershipforsolutions.com/DMS/files/DMfactsheet21final.pdf.

Partnership for Solutions, "Multiple Chronic Conditions: Complications in Care and Treatment", May 2002, [online] [retrieved on Mar. 11, 2004]. Retrieved from the Internet: URL: http://www.partnershipforsolutions.com/DMS/files/2002/multiplecoitions.pdf.

Peddicord, H., "A New Health Care & Business Model for Home Care Agencies", [online] [retrieved on Mar. 11, 2004]. Retrieved from the Internet: URL: http://www.hommed.com/healthcare_professionals/model_print.html.

Pomerantz, J., MD, "Recycling Expensive Medication: Why Not?", Medscape General Medicine, posted Apr. 23, 2004 [online] [retrieved on May 5, 2004]. Retrieved from the intemet: URL: http://www.medscape.com/viewarticle/472851.

Public Broadcast System, "Fred Friendly Seminars, Who Cares?: Chronic Illness in America", Broadcast Fall 2001, [summary information online] [retrieved on Mar. 11, 2004]. Retrieved from the Internet: URL: http://www.pbs.org/fredfriendly/whocares/about_the program/about_the_program.html.

Reece, R., MD, "New Sources of Revenue Open Up Possibilities", MD Options, Feb. 15, 2002, [online] [retrieved on Mar. 11, 2004]. Retrieved from the Internet: URL: http://www.mdoptions.com/cgi-bin/article.cgi?article_id=1097.

Reece, R., MD, "Office Dispensing Can Enhance Care Quality by Helping to Cut Drug Errors", MD Options, Apr. 2003, [online] [retrieved on Mar. 11, 2004]. Retrieved from the Internet: URL: http://www.mdoptions.com/cgi-bin/article.cgi?article_id=1412.

Reece, R., MD, "Office Dispensing Enhances Revenue, Compliance, Industry Leader Says", Physician Practice Options, May 15, 2002, pp. 13-15.

Reece, R., MD, "Will Dispensing Make a Comeback?", MD Options, Feb. 15, 2002, [online] [retrieved on Mar. 11, 2004]. Retrieved from the Internet: URL: http://www.mdoptions.com/cgi-bin/article.cgi?article_id=1098.

Rubin, R., PhD, CDE & Polonsky, W., PhD, CDE, "Medication Compliance in Diabetes: A Strategic Guide for the Practicing Pharmacist", Power-Pak C.E. Program No. 424-999-03-022-H01, Release Date: Nov. 2003, [online] [retrieved on Mar. 11, 2004]. Retrieved from the Internet: URL: http://www.powerpak.com/print.asp?page=courses/2995/lesson.htm.

RxHub LLC, "The Challenges of Today's Prescribing Process", Aug. 2002, [online] [retrieved on Mar. 11, 2004]. Retrieved from the Internet: URL: http://www.rxhub.net/pdf/PrescrProc.pdf.

Schlesselman, L., Pharm.D., "Compliance Issues", Drug Store News TechEdProgram No. 401-000-04-005-H01, Initial release date: Feb. 1, 2004, [online] [retrieved on Mar. 11, 2004]. Retrieved from the Internet: URL: https://www.cedrugstorenews.com/userapp/lessons/lesson_view_ui.cfm?lessonuid=401%2D000%2D04%2D005%2DH01.

Schneider, P., "Digital Rx", Healthcare Informatics, Feb. 1998.

Sellers, J., "Editorial: Too Many Medication Errors, Not Enough Pharmacists", Am, 1 Health-Syst Pharm vol. 57 Feb. 15, 2000, p. 337.

Smith, D., Pharm.D., "Consumers Hold the Key to Controlling Health Care Costs", Pharmacy Connects, Feb. 1998.

Smith, D., Pharm.D., "Staggering Cost of Home Medication Errors: The Overlooked Cost in Prescription Drug Coverage" in "Taking Control of Your Medicines: vol. 1 No. 1", Consumer Health Information Corporation, 2001, [online] [retrieved on Mar. 11, 2004]. Retrieved from the Internet: URL: http://www.consumer-health.com/services/cons_take15.htm.

Smith, D., Pharm.D., 97% of Patient Education Materials Don't Work . . . Do Yours? in "Patient Information Update, vol. 1, No. 1", Consumer Health Information Corporation, 2002, [online] [retrieved on Mar. 11, 2004]. Retrieved from the Internet: URL: http://www.consumer-health.com/pharm/peu/peu_vol1_no1.htm.

Snyder, K., "Telemedicine, the New Frontier", Drug Topics, Aug. 4, 1997.

Stensland, S., Pharm.D., "Prescription Refills: Are They Really Important?", Drug Store News TechEdProgram No. 401-000-02-029-H01, Initial release date: Nov. 15, 2002, [online] [retrieved on Mar. 11, 2004]. Retrieved from the Internet URL: https://www.cedrugstorenews.com/userapp/lessons/lesson_view_ui.cfm?lessonuid=401%2D000%2D02%2D029%2DH01.

Stergachis, A., PhD, RPh, "The Role of the Pharmacist in Improving Patient Adherence with Medication Regimes", Power-Pak C.E. Program No. 424-000-03-021-H04, Release Date: Oct. 2003, [online] [retrieved on Mar. 11, 2004]. Retrieved from the Internet: URL: http://www.powerpak.com/print.asp?page=courses/2957/lesson.htm.

Tanner, L., "Home Health Care Goes High-Tech -Telemedicine Permits Close Monitoring of Patients With Fewer Nurse Visits", Dallas Business Journal, Oct. 18, 2002.

Tassone, A., Pharm.D., & Tomecki, M., Pharm.D., "Medication Errors in the Community Pharmacy", Drug Store News TechEd Program No. 401-000-02-002-H01, Release Date: Jan. 30, 2002, [online] [retrieved on Mar. 11, 2004]. Retrieved from the Internet: URL: https://www.cedrugstorenews.com/userapp/lessons/lesson_view_detail.cfm?lessonuid=401%2D000%2D02%2D002%2DH01 .

The Academy of Managed Care Pharmacy, "Concepts in Managed Care Pharmacy - Pharmaceutical Care", [online] [retrieved on Mar. 11, 2004]. Retrieved from the Internet: URL: http://www.amcp.org/amcp.ark?c=legislative&sc=concepts&id=2.

The Academy of Managed Care Pharmacy, "Concepts in Managed Care Pharmacy - Medication Errors", [online] [retrieved on Nov. 3, 2004]. Retrieved from the Internet: URL: http://www.amcp.org/amcp.ark?c=legislative&sc=concepts&id=0.

The Academy of Managed Care Pharmacy, "Concepts in Managed Care Pharmacy - Disease State Management/Health Management", [online] [retrieved on Mar. 11, 2004]. Retrieved from the Internet: URL: http://www.amcp.org/amcp.ark?c=legislative&sc=concepts&id=3.

The American Society of Consultant Pharmacists, "ASCP Policy Statement - Statement on the Return and Reuse of Medications in Long-term Care Facilities", [online] [retrieved on Mar. 11, 2004]. Retrieved from the Internet: URL: http://www.ascp.com/public/pr/policy/return.shtml.

The American Society of Consultant Pharmacists, "Assisted Living Residents Need Medication Management Services", Jun. 19, 2002 [online] [retrieved on Mar. 11, 2004]. Retrieved from the Internet: URL: http://www.ascp.com/public/news/2002/06/19-management.shtml.

The American Society of Consultant Pharmacists, "Largest Study of Medication Use in U.S. Nursing Facilities Since 1997 Yields Current, Definitive Benchmark Data", Mar. 5, 2001, [online] [retrieved on Mar. 11, 2004]. Retrieved from the Internet: URL: http://www.ascp.com/public/news/2001/03/05-meduse.shtmi.

The American Society of Consultant Pharmacists, "Medication Use Levels in U.S. Assisted Living Facilities Are Comparable to Those in Skilled Nursing Facilities, New Research Indicates", Mar. 2, 2001, [online] [retrieved on Mar. 11, 2004]. Retrieved from the Internet: URL: http://www.ascp.com/public./news/2001/03/02-alf_snf.shtml.

The National Institute for Health Care Management Research and Educational Foundation, "Prescription Drugs and Mass Media Advertising, 2000". Nov. 2001.

The Virginia Department of Health Professions, Hospital Pharmacy "Dirty Dozen" [online] [retrieved on Mar. 11, 2004]. Retrieved from the Internet: URL: http://www.dhp.state.va.us/enforcement/guidelines/76-20.2.doc.

The United States Pharmacopeia, "Computer Entry a Leading Cause of Medication Errors in U.S. Health Systems", Dec. 20, 2004 Press Release [online] [retrieved on Jan. 11, 2005] Retrieved from the Internet: URL: http://vocuspr.vocus.com/NocusPR30/DotNet/Newsroom/Query .as px?SiteName =uspnews&Entity= PRA s set &SF PRAsset PRAssetID EO=95555&XSL =PressRelease &Cache=True].

Thompson, T, and Brailer, D. MD, Pill, "The Decade of Health Information Technology: Delivering Consumer-centric and Information-rich Health Care - Framework for Strategic Action", U.S. Dept. of Health and Human Services, Jul. 21, 2004 [online] [retrieved on Oct. 6, 2004]. Retrieved from the intemet: URL: http://www.hhs.gov/onchit/framework/hitframeworkpdf.

Triller, D., Clause. S. & Domarew, C., "Analysis of Medication Management Activities for Home-Dwelling Patients", Am J Health-Syst Pharm 59(23):2356-2359, 2002.

Troiano, D., "A Primer on Pharmacy Information Systems", Journal of Healthcare Information Management, vol. 13, No. 3, Fall 1999, pp. 41-52.

Ukens, C., "Automation: Pharmacists' friend or foe?", Drug Topics 1999; 19:74.

Ukens, C., "Deadly Dispensing", Drug Topics, Mar. 3, 1997.

Ukens, C., "Pharmacist Shortage Boosts Telepharmacy", Drug Topics, 2002;11:53.

Ukens, C., "Remote Control -Automation Puts Retail R.Ph.'s Foot in Doctor's Door", Drug Topics, Jan. 20, 1997.

Ukens, C., "Technopharmacy - Love it or Hate it, Technology is Here to Stay. So Here are the Results of our Exclusive Survey on What's Out There, What's Ahead, and How it Will Impact Your Practice", Drug Topics, Nov. 2, 1998.

Urquhart, J., "New Insight into Patient Noncompliance with Prescribed Drug Regimens", Clinical Researcher, vol. 1., No. 6, Jun. 2001, pp. 26-32.

U.S. Census Bureau "2002 Statistical Abstract of the U.S. - Section 3 Health and Nutrition", [online] [retrieved on Mar. 11, 2004]. Retrieved from the Internet: URL http://www.census.gov/prod/2003pubs/02statab/health.pdf.

U.S. Dept of Health and Human Services Office of the Inspector General, "Reducing Medication Problems of the Elderly", OEI-04-89-89122, Oct. 1990.

Vecchione. T., "Medication Error Reduction Driving Technology Trends", Drug Topics, Jan. 21, 2002.

Williams, B., Pharm.D., FASCP, CGP, "Therapeutic Interventions for Seniors", Drug Store Newts TechEdProgram No. 401-000-03-023-H01, Initial release date: Nov. 1, 2003, [online] [retrieved on Mar. 11, 2004]. Retrieved from the Internet: URL: http://www.cedrugstorenews.com/userapp/lessons/lesson_view_detaii.cfm?lessonuid=401%2D000%2D03%2D023%2DH01.

Wogen, S., MHA, Fulop, G., MD, MS & Heller, J., RN, "Electronic Prescribing - Improving the Efficiency of the Prescription Process and Promoting Plan Adherence", Drug Benefit Trends 15(9):35-40, 2003.

Wolff J., Starfield B. & Anderson G., "Prevalence, Expenditures, and Complications of Multiple Chronic Conditions in the Elderly" Archives of Internal Medicine, Nov. 11, 2002, vol. 162, pp. 2269-2276.

World Health Organization, "Adherence to Long-Term Therapies: Evidence for Action", 2003, [online] [retrieved on Mar. 11, 2004]. Retrieved from the Internet: URL: http://www.who.int/chronic_conditions/adherencereport/en/.

Zuger, A., "The 'Other' Drug Problem: Forgetting to Take Them", New York Times, Jun. 2, 1998.

Drug Management Systems For Hospitals: Website for McKesson Automation Solutions for Pharmacy: http://www.mckessonautomation.com/wt/auto/pharm_index.

Drug Management Systems For Hospitals: Website for Med-Dispense: http://www.med-dispense.com/.

Drug Management Systems For Hospitals: Website for Omnicell, Inc.: http://www.omnicell.com.

Drug Management Systems For Hospitals: Website for Pyxis Corporation, a division of Cardinal Health: http://www.pyxis.com.

Drug Dispensing Equipment for The Drug Store and Hospital Market: Website for Asteres, Inc: http://www.asteres.com/products.html.

Drug Dispensing Equipment for The Drug Store and Hospital Market: Website for AutoMed Technologies, Inc.: http://www.automedrx.com.

Drug Dispensing Equipment for The Drug Store and Hospital Market: Website for Scriptpro LLC: http://www.scriptpro.com.

Dispensing Systems for Physician's Offices: Website for Allscripts Healthcare Solutions: http://www.allscripts.com.

Dispensing Systems for Physician's Offices: Website for Dispensing Solutions: http://www.dispensingsolutionsinc.com.

Dispensing Systems for Physician's Offices: Website for DRx, The Doctor's Dispensing Network: http://www.drxnet.com.

Dispensing Systems for Physician's Offices: Website for Medvantx: http://www.medvantx.com.

Dispensing Systems for Physician's Offices: Website for Mendota Healthcare, producer of InstyMeds: http://www.instymeds.com.

Dispensing Systems for Physician's Offices: Website for PD-RX Pharmaceuticals, Inc: http://www.pdrx.com.

Dispensing Systems for Physician's Offices: Website for Physicians Total Care: http://www.physicianstotalcare.com.

Dispensing Systems for Physician's Offices: Website for Telepharmacy Solutions: http://www.telepharmacysolutions.com.

Personal Automatic Pill Dispensers and Monitoring Systems: Website for CompuMed, Inc.: http://www.compumed.com/index1.htm.

Personal Automatic Pill Dispensers and Monitoring Systems: Website for e-pill, LLC.: http://www.epill.com.

Personal Automatic Pill Dispensers and Monitoring Systems: Website for HomMed LLC: http://www.hommed.com/.

Personal Automatic Pill Dispensers and Monitoring Systems: Website for Information Mediary Corporation, producer of the The Med-ic™ ECM™: http://www.informationmediary.com/med-ic.htm.

Personal Automatic Pill Dispensers and Monitoring Systems: Website for InforMedix. Inc., producer of the Med-eMonitor System: http://www.informedix.com.

Personal Automatic Pill Dispensers and Monitoring Systems: Website for Interactive Medical Developments, L.C., producer of the MD.2: http://www.imd2.com/.

Personal Automatic Pill Dispensers and Monitoring Systems: Website for Sharper Image, Inc.: http://www.sharperimage.com.

Non-Final Office Action for U.S. Appl. No. 11/548,130, mailed on May 22, 2009, 8 pages.

* cited by examiner

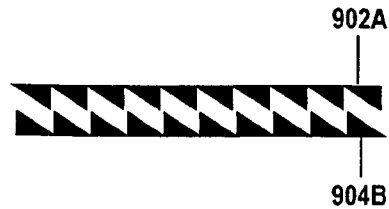
FIG. 14A    FIG. 14B
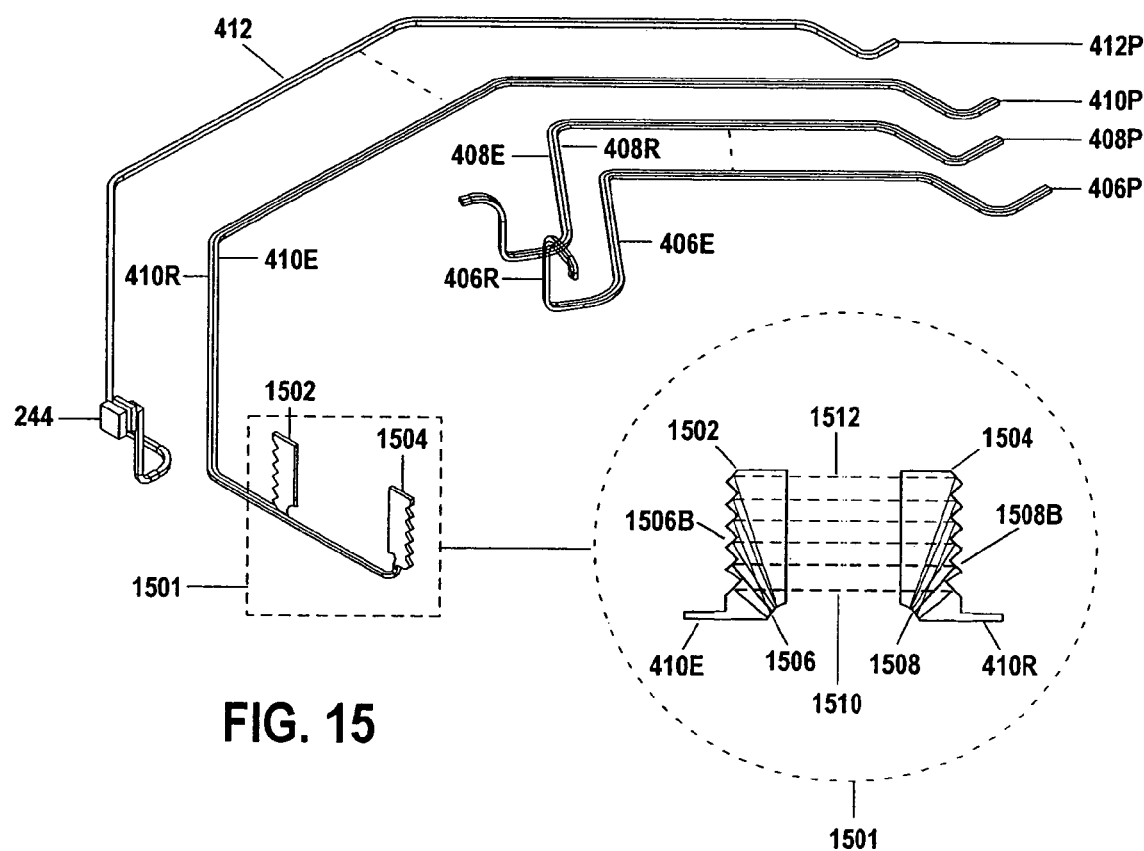
FIG. 15
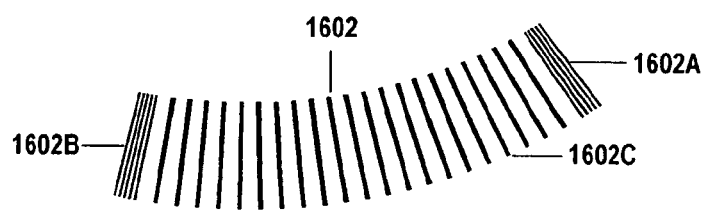
FIG. 16

1726 — PATIENT A: INFORMATION

| PATIENT ID NO. | | MALE ☐ YES | FEMALE ☐ YES |
|---|---|---|---|
| LAST NAME | | | |
| FIRST NAME | | MIDDLE INITIAL | |
| SOC. SEC. NO. | | DATE OF BIRTH | |
| ADDRESS 1 | | | |
| ADDRESS 2 | | | |
| CITY | | STATE | |
| ZIP CODE | | PHONE NO. | |
| CELL NO. | | PAGER NO. | |
| E-MAIL | | | |

1728 — PATIENT A: ALLERGIES

| NONE KNOWN | ☐ YES | LATEX | ☐ YES |
|---|---|---|---|
| ASPIRIN | ☐ YES | LADOCAINE | ☐ YES |
| BARBITURITES | ☐ YES | MORPHINE | ☐ YES |
| CODEINE | ☐ YES | NOVOCAINE | ☐ YES |
| DEMEROL | ☐ YES | PENICILLIN | ☐ YES |
| ENVIRONMENTAL | ☐ YES | SULFA | ☐ YES |
| ERYTHROMYCIN | ☐ YES | TETRACYCLINE | ☐ YES |
| HORSE SERUM | ☐ YES | X-RAYS DYES | ☐ YES |
| INSECT STINGS | ☐ YES | OTHER | |

1730 — PATIENT A: MEDICAL CONDITIONS

| NONE KNOWN | ☐ YES | HEMOLYTIC ANEMIA | ☐ YES |
|---|---|---|---|
| ABNORMAL EKG | ☐ YES | HIGH BLOOD PRESSURE | ☐ YES |
| ACTIVE ULCER | ☐ YES | HYPERTENSION | ☐ YES |
| ADRENAL INSUFFICIENCY | ☐ YES | HYPERTHYROID | ☐ YES |
| ALZHEIMER'S | ☐ YES | HYPOGLYCEMIA | ☐ YES |
| ANGINA | ☐ YES | HYPOTHYROID | ☐ YES |
| ARTHRITIS | ☐ YES | KIDNEY DISORDER | ☐ YES |
| ASTHMA | ☐ YES | LARYNGECTOMY | ☐ YES |
| BLEEDING DISORDER | ☐ YES | LEUKEMIA | ☐ YES |
| CARDIAC DYSRHYTHMIA | ☐ YES | LIVER DISORDER | ☐ YES |
| CARDIOVASCULAR | ☐ YES | LOW BLOOD PRESSURE | ☐ YES |
| CATARACTS | ☐ YES | LYMPHOMA | ☐ YES |
| CLOTTING DISORDER | ☐ YES | MALIGNANT HYPOTHERMIA | ☐ YES |
| CONGESTIVE | ☐ YES | MEMORY IMPAIRED | ☐ YES |
| CORONARY BYPASS GRAFT | ☐ YES | MYASTHENIA GRAVIS | ☐ YES |
| DEMENTIA | ☐ YES | PACEMAKER | ☐ YES |
| DEPRESSION | ☐ YES | RENAL FAILURE | ☐ YES |
| DIABETES | ☐ YES | SEIZURE DISORDER | ☐ YES |
| DIABETES/INSULIN DEPENDENT | ☐ YES | SICKLE CELL ANEMIA | ☐ YES |
| EYE SURGERY | ☐ YES | STROKE | ☐ YES |
| GLAUCOMA | ☐ YES | VISION IMPAIRED | ☐ YES |
| HEARING IMPAIRED | ☐ YES | BLOOD TYPE | |
| HEART FAILURE | ☐ YES | OTHER | |
| HEART VALVE PROSTHESIS | ☐ YES | | |
| HEMODIALYSIS | ☐ YES | | |

1732 — PATIENT A: PRESCRIBER INFORMATION

| DOCTOR ID NO. | | | |
|---|---|---|---|
| LAST NAME | | | |
| FIRST NAME | | MIDDLE INITIAL | |
| ADDRESS 1 | | | |
| ADDRESS 2 | | | |
| CITY | | STATE | |
| ZIP CODE | | PHONE NO. | |
| E-MAIL | | | |

FIG. 17B

1734 — PATIENT A: PRESCRIPTION INSURANCE INFORMATION

| CARRIER NAME | | | |
|---|---|---|---|
| GROUP NO. | | CONTRACT NO. | |
| DRUG DISCOUNT | | | |
| CARRIER NAME | | | |
| CARD NO. | | | |
| MEDICARE NO. | | | |
| MEDICAID NO. | | | |
| OHP STANDARD | ☐ YES | OHP PLUS | ☐ YES |

1736 — PATIENT B: INFORMATION

| PATIENT ID NO. | | MALE ☐ YES | FEMALE ☐ YES |
|---|---|---|---|
| LAST NAME | | | |
| FIRST NAME | | MIDDLE INITIAL | |
| SOC. SEC. NO. | | DATE OF BIRTH | |
| ADDRESS 1 | | | |
| ADDRESS 2 | | | |
| CITY | | STATE | |
| ZIP CODE | | PHONE NO. | |
| CELL NO. | | PAGER NO. | |
| E-MAIL | | | |

1738 — PATIENT B: ALLERGIES

| NONE KNOWN | ☐ YES | LATEX | ☐ YES |
|---|---|---|---|
| ASPIRIN | ☐ YES | LADOCAINE | ☐ YES |
| BARBITURITES | ☐ YES | MORPHINE | ☐ YES |
| CODEINE | ☐ YES | NOVOCAINE | ☐ YES |
| DEMEROL | ☐ YES | PENICILLIN | ☐ YES |
| ENVIRONMENTAL | ☐ YES | SULFA | ☐ YES |
| ERYTHROMYCIN | ☐ YES | TETRACYCLINE | ☐ YES |
| HORSE SERUM | ☐ YES | X-RAYS DYES | ☐ YES |
| INSECT STINGS | ☐ YES | OTHER | |

1740 — PATIENT B: MEDICAL CONDITIONS

| NONE KNOWN | ☐ YES | HEMOLYTIC ANEMIA | ☐ YES |
|---|---|---|---|
| ABNORMAL EKG | ☐ YES | HIGH BLOOD PRESSURE | ☐ YES |
| ACTIVE ULCER | ☐ YES | HYPERTENSION | ☐ YES |
| ADRENAL INSUFFICIENCY | ☐ YES | HYPERTHYROID | ☐ YES |
| ALZHEIMER'S | ☐ YES | HYPOGLYCEMIA | ☐ YES |
| ANGINA | ☐ YES | HYPOTHYROID | ☐ YES |
| ARTHRITIS | ☐ YES | KIDNEY DISORDER | ☐ YES |
| ASTHMA | ☐ YES | LARYNGECTOMY | ☐ YES |
| BLEEDING DISORDER | ☐ YES | LEUKEMIA | ☐ YES |
| CARDIAC DYSRHYTHMIA | ☐ YES | LIVER DISORDER | ☐ YES |
| CARDIOVASCULAR | ☐ YES | LOW BLOOD PRESSURE | ☐ YES |
| CATARACTS | ☐ YES | LYMPHOMA | ☐ YES |
| CLOTTING DISORDER | ☐ YES | MALIGNANT HYPOTHERMIA | ☐ YES |
| CONGESTIVE | ☐ YES | MEMORY IMPAIRED | ☐ YES |
| CORONARY BYPASS GRAFT | ☐ YES | MYASTHENIA GRAVIS | ☐ YES |
| DEMENTIA | ☐ YES | PACEMAKER | ☐ YES |
| DEPRESSION | ☐ YES | RENAL FAILURE | ☐ YES |
| DIABETES | ☐ YES | SEIZURE DISORDER | ☐ YES |
| DIABETES/INSULIN DEPENDENT | ☐ YES | SICKLE CELL ANEMIA | ☐ YES |
| EYE SURGERY | ☐ YES | STROKE | ☐ YES |
| GLAUCOMA | ☐ YES | VISION IMPAIRED | ☐ YES |
| HEARING IMPAIRED | ☐ YES | BLOOD TYPE | |
| HEART FAILURE | ☐ YES | OTHER | |
| HEART VALVE PROSTHESIS | ☐ YES | | |
| HEMODIALYSIS | ☐ YES | | |

FIG. 17C

1742 — PATIENT B: PRESCRIBER INFORMATION

| DOCTOR ID NO. | | | |
|---|---|---|---|
| LAST NAME | | | |
| FIRST NAME | | MIDDLE INITIAL | |
| ADDRESS 1 | | | |
| ADDRESS 2 | | | |
| CITY | | STATE | |
| ZIP CODE | | PHONE NO. | |
| E-MAIL | | | |

1744 — PATIENT B: PRESCRIPTION INSURANCE INFORMATION

| CARRIER NAME | | | |
|---|---|---|---|
| GROUP NO. | | CONTRACT NO. | |
| DRUG DISCOUNT | | | |
| CARRIER NAME | | | |
| CARD NO. | | | |
| MEDICARE NO. | | | |
| MEDICAID NO. | | | |
| OHP STANDARD | ☐ YES | OHP PLUS | ☐ YES |

1746 — DRUG STORE INFORMATION

| BUSINESS NAME | |
|---|---|
| ADDRESS 1 | |
| ADDRESS 2 | |
| CITY | |
| STATE | |
| ZIP CODE | |
| PHONE NO. | |
| E-MAIL | |
| ORDER URL | |

1748 — PATIENT PAYMENT INFORMATION

| CREDIT CARD TYPE | |
|---|---|
| CREDIT CARD NO. | |
| EXPIRATION DATE | |
| CARD NAME | |
| CARD SECURITY NO. | |
| IF NOT PATIENT | ☐ YES |
| ADDRESS 1 | |
| ADDRESS 2 | |
| CITY | |
| STATE | |
| ZIP CODE | |
| PHONE NO. | |
| E-MAIL | |

FIG. 17D

1826 — 1 PRESCRIBER INFORMATION

| DOCTOR ID NO. | |
|---|---|
| LAST NAME | |
| FIRST NAME | MIDDLE INITIAL |
| ADDRESS 1 | |
| ADDRESS 2 | |
| CITY | STATE |
| ZIP CODE | PHONE NO. |
| E-MAIL | |

⋮

1828 — 20 PRESCRIBER INFORMATION

| DOCTOR ID NO. | |
|---|---|
| LAST NAME | |
| FIRST NAME | MIDDLE INITIAL |
| ADDRESS 1 | |
| ADDRESS 2 | |
| CITY | STATE |
| ZIP CODE | PHONE NO. |
| E-MAIL | |

1830 — PAYMENT ACCEPTED

| VISA | YES |
|---|---|
| MASTER CARD | YES |
| AMERICAN EXPRESS | YES |
| DEBIT CARD | YES |
| CHEQUE | YES |
| CASH | YES |
| OTHER | YES |
| | YES |
| | YES |

1832 — APPROVED PRESCRIPTION BY INSURANCE COMPANY

1834 — DRUG STORE INFORMATION

| BUSINESS NAME | |
|---|---|
| ADDRESS 1 | |
| ADDRESS 2 | |
| CITY | |
| STATE | |
| ZIP CODE | |
| PHONE NO. | |
| E-MAIL | |
| ORDER URL | |

FIG. 18B

MEDICAMENT INVENTORY SYSTEM AND METHOD

CROSS-REFERENCE TO RELATED APPLICATION

This application is a continuation of U.S. application Ser. No. 10/939,620, having a filing date of 13 Sep. 2004, the contents of which are incorporated herein by reference in their entirety.

BACKGROUND OF THE INVENTION

1. Field of the Invention

The present invention relates to a method and system for automatically dispensing medicaments. More particularly, the invention relates to a method and system that utilizes one or more cassettes or trays, which hold one or more types of medicaments, the cassettes or trays being configured for secure and intelligent dispensing of the medicaments.

2. Description of the Related Art

Conventionally, medicaments have been distributed or provided to patients in a manual fashion. In such manual distribution methods and systems, a patient receives a prescription from a medical practitioner in writing and the prescribed medicaments may thereafter be purchased at a pharmacy. This method of manual distribution of medicaments has several problems associated with it. One problem is that wrong medicines or wrong dosages may be dispensed due to human error, potentially causing serious injury to the patient or even death. Another problem with manual distribution methods is that unauthorized medicines that have not been prescribed by a medical practitioner can be dispensed in error or the medicaments can be stolen due to inadequate tracking and non-secure storage and transit of the medicaments. Furthermore, current manual distribution methods do not monitor for counterfeit medications, medication side effects and timely intake of prescribed medicines by the patient. For example, a patient may skip or delay the intake of a medicament, or take the medicament too frequently, which could reduce the effect of the medicament or even be harmful to the patient.

In order to overcome the above-mentioned problems, several automated medicament distribution systems have been developed. Typically, these automated drug dispensing systems are isolated units, placed at specified locations within a hospital, pharmacy, a patient's home, or other strategic location. These dispensing systems may be programmed for scheduled dispensation of medicines. To ensure authorized dispensing of medicaments, one or more automated drug dispensing systems can be connected to a remote computer or processor that monitors the activities of each dispensing machine. Such remote computers/processors serve an authorization node, which allows a practitioner or other authorized personnel to control the dispensing of medicaments to one or more patients. Additionally, each remote computer may be connected to a central computer or node that controls and monitors a larger number of automatic dispensing machines in a wider geographic area.

U.S. Pat. No. 6,564,121, entitled "Systems and Methods for Drug Dispensing", assigned to Telepharmacy Solutions, Inc. (North Billerica, Mass.), filed on Dec. 3, 1999, discloses a system and method for remotely dispensing medical products using a networked communications system. The disclosed system utilizes a computer network for delivery of patient information and dispensing instructions to a remote dispensing station. The system includes an authorization node to authorize dispensing, a dispensing node to dispense the medical product and a controlling node, which interfaces with the authorization and dispensing nodes. Similarly, U.S. Patent Publication No. 20030036683, entitled "Method, System and Computer Program Product for Internet-enabled, Patient Monitoring System," provides a health status and pharmaceutical compliance monitoring system. The system comprises a medication storing system that is linked to a medical information management system and database.

However, the above systems have certain limitations associated with them. For example, especially when used at the patient's end, these systems do not provide adequate security against tampering or theft. Moreover, in these systems, medicaments have to be sorted into numerous compartments or cups and loaded in the correct order so that they can be dispensed at the scheduled times.

In order to address the above-mentioned problems, several cassettes for use in conjunction with an automatic dispensing device or system have been developed. For example, U.S. Pat. No. 6,578,733, entitled "Cassette for Storing and Feeding Discrete Objects", assigned to Kirby-Lester, Inc. (Stamford, Conn.), filed on May 31, 2001, discloses a cassette for counting and dispensing objects. The cassette is adapted to feed and guide tablets having a range of sizes and shapes towards an exit. Another such patent is U.S. Pat. No. 4,018,358, entitled "Cassette Pill Storing, Dispensing and Counting Machine", assigned to Medicine Innovators, Ltd. (West Union, Iowa), and filed on Sep. 18, 1975. This patent relates to a system that includes separate cassettes for storing different pills. The cassettes are operated by a dispensing machine. The dispensing machine provides a vacuum supply and a drive for operating a wheel in the cassette to pick up pills in the bottom of the cassette and carry them to a discharge opening under the vacuum pressure. The system further comprises a fiber optic scanner at the discharge opening that counts each pill.

Various other prior art patents have disclosed similar mechanisms for dispensing medicaments. These include: U.S. Pat. No. 6,332,100, entitled "Apparatus and Method for Medication Dispensing and Messaging", assigned to Interactive Medical Developments, L.C.; U.S. Patent Publication No. 20030183642, entitled "Pill Dispensing Apparatus"; and U.S. Pat. No. 6,554,157, entitled "Cassette Systems for Feeding, Counting and Dispensing Discrete Objects," assigned to Kirby-Lester, Inc.

However the above cited patents suffer from one or more of the following drawbacks or limitations. Firstly, in the case of existing cassettes or compartments for dispensing of medicaments, it is difficult to identify the content of each cassette to ensure that the correct medicament(s) are stored therein. Secondly, in these systems, cups or cassettes containing the medicament units have to be manually filled, requiring significant manual labor which is prone to errors. Thirdly, these systems have to be programmed manually to indicate the positioning of each tray and the medicaments stored therein. Any error during the manual programming of the dispensing machine may lead to a wrong medication being dispensed.

In view of the above mentioned drawbacks and limitations of the existing systems, there is a need for a cassette or tray that, when used in conjunction with a dispensing machine or system, provides improved security against tampering or theft. Further, there is a need for a system, which minimizes manual operations (e.g., programming of the system) and is therefore less prone to errors. There is also a need for a method and system for automatic dispensing of medicaments, which is capable of correctly identifying the medicaments it is dispensing. Additionally, there is a need for a method and system that can identify the correct cassette or tray for dispensing a particular medicine, irrespective of the cassette's or tray's loading position in the dispensing machine. Furthermore, such systems should be hermetically sealed, so that they may be returnable to a pharmacy or other vendor or institution if not used by a hospital or patient.

BRIEF SUMMARY OF VARIOUS EMBODIMENTS OF THE INVENTION

The invention provides a cassette or tray that can be used in conjunction with an automatic medicament dispensing machine for secure and intelligent dispensing of medicament units.

In one embodiment, an automatic medicament dispensing system stores and communicates information regarding its contents, operations and/or functions to at least one remote device or computer. This information can include information such as, for example, inventory information pertaining to a number of medicament units in a medicament dispensing tray.

In one embodiment, the tray is capable of counting the medicaments being dispensed and stores the inventory of the tray in a storage device, which in one embodiment is a wireless communication device which can be read by a wireless communication device reader within an automatic dispensing machine or system or external to the machine or system. Information from the wireless communication device can also be relayed or transmitted to one or more external computers or devices that may be monitoring the contents, operations and/or status of the automatic dispensing machine.

In a further embodiment, a medicaments dispensing tray for dispensing medicament units, includes: a housing configured to contain the plurality of medicament units; an information storage device configured to maintain information pertaining to the plurality of medicament units in the medicaments dispensing container, the information pertaining to the plurality of medicament units comprising inventory information for the plurality of medicament units in the medicaments dispensing container; and a communication device communicatively coupled to the information storage device and configured to allow communication of the inventory information between the information storage device and a server to facilitate automated inventory tracking for at least one of a plurality of medicament units. In one embodiment, the inventory update logic can include a sensor unit, to sense a medicament unit being dispensed from the medicaments dispensing container, which can be implemented, for example as an optical sensor.

In one embodiment, the tray can be configured to track a number of medicament units dispensed from the medicaments dispensing container using software, firmware, hardware or any combination of the three. The inventory information can be updated to reflect a quantity of medicament units dispensed from the medicaments dispensing container, or the number of medicament units remaining in the medicaments dispensing container.

In another embodiment, the system, through either the tray or an external computing device, is configured to determine whether to reorder additional medicament units based on the updated inventory information. In embodiments in which the medicaments in the medicaments dispensing container are provided to a recipient (e.g., a patient) under a prescription, the system can be implemented to determine a number of refills remaining under the prescription. The system can be further configured to determine whether a patient for whom the medicament units in the medicaments dispensing container were prescribed is authorized to receive a refill of the prescription.

In a further embodiment, the tray is configured to send a signal to the server to reorder additional medicament units. The tray can also be configured to send a signal to the server indicating a quantity of medicament units remaining in the medicaments dispensing container.

In yet another embodiment of the invention, the medicaments dispensing tray is configured to determine a quantity of medicament units dispensed from the medicaments dispensing tray; and to determine whether to reorder additional medicament units based on medicament information when a quantity of medicament units remaining in the medicaments dispensing tray reaches a predetermined level. The medicaments dispensing tray can be configured to determine a quantity of medicament units dispensed from the medicaments dispensing container; and to determine whether to reorder medicament units based on patient information when a quantity of medicament units remaining in the medicaments dispensing container reaches a predetermined level.

In still another embodiment of the invention, the medicaments dispensing tray is configured to receive updates from a dispensing machine by way of the communication device. The updates can be entered by a caregiver in one embodiment. Additionally, in one embodiment, information pertaining medicament units in the medicaments dispensing container is communicated to an insurance agency to facilitate claim processing.

In still other embodiments, the medicaments dispensing container includes an indicator configured to be activated when a quantity of medicament units remaining in the medicaments dispensing container reaches a predetermined amount. The indicator can be implemented using, for example, a luminous indicator, an audible indicator, a radio frequency indicator or other like device. In one embodiment the indicator is configured to be activated upon a determination by the inventory control logic that the quantity of medicament units remaining in the medicaments dispensing container has reached a predetermined amount.

In another embodiment, a server or other external computing device is configured to receive the inventory information and to determine a quantity of medicament units remaining in the medicaments dispensing container. The inventory information can include a quantity of medicament units dispensed from the medicaments dispensing container and a quantity of medicament units remaining in the medicaments dispensing container. In embodiments where a server or other external computing device does the reordering, the server can be further configured to determine whether to reorder additional medicament units when the quantity of medicament units remaining in the medicaments dispensing container.

In still another embodiment of the invention, a method of dispensing medicament units from a medicament units container, is provided, wherein the method includes the steps of: dispensing at least one medicament unit from the medicament units container; tracking dispensation of the at least one medicament unit from the medicament units container; and determining, responsive to dispensation of the at least one medicament unit from the medicament units container, inventory information indicating the quantity of medicament units remaining in the medicaments dispensing container. The method can include the step of communicating the inventory information between the medicaments dispensing container and an external computing device to facilitate automated inventory tracking for the medicament units.

In one embodiment, communicating the inventory information signal to an external computing device thereby facilitates a reorder of medicament units in the medicaments dispensing container by the external computing device. The inventory information can be maintained at the medicaments dispensing container and an external computing device.

In yet another embodiment of the invention, the method further includes generating a reorder signal when the quantity of medicament units remaining in the medicaments dispensing container reaches a predetermined amount, wherein the reorder signal causes an order to be placed for additional medicament units. The reorder signal can be generated by the medicament units container or the server.

In still another embodiment of the invention, the method includes verifying that a refill of a prescription for the medicament units in the medicaments dispensing container is authorized for a patient being served by the medicaments dispensing container.

In yet another embodiment of the invention a computer program product for use in a medicaments dispensing container is provided. The computer program product includes machine readable code configured to cause a computing device to track dispensation of at least one medicament unit from the medicament dispensing container; and determine, inventory information indicating the quantity of medicament units remaining in the medicaments dispensing container.

BRIEF DESCRIPTION OF THE DRAWINGS

FIG. 14A and FIG. 14B are cross-sectional views of illustrating engagement gear-toothed surfaces on conical disks used in a medicament dispensing tray, in accordance with embodiments of the invention;

FIG. 15 is a perspective view of fiber optic cables with end shaped lens used in a medicament dispensing tray, in accordance with one embodiment of the invention;

FIG. 16 is an illustration of the main conical disk encoder layout used in a medicament dispensing tray, in accordance with one embodiment of the invention;

FIGS. 17A, 17B, 17C, 17D and 17E illustrate layouts of a patient memory table that may be stored within a medicament dispensing tray and/or an automatic dispensing machine, in accordance with one embodiment of the invention;

FIGS. 18A, 18B, and 18C illustrate layouts of a healthcare professional memory table that may be stored within a medicament dispensing tray and/or an automatic dispensing machine, in accordance with one embodiment of the invention.

DETAILED DESCRIPTION OF THE PREFERRED EMBODIMENTS OF THE INVENTION

Preferred embodiments of the invention are described in detail below with reference to the figures, wherein like elements are referenced with like numerals throughout. In one embodiment, the present invention provides a smart dispensing tray for storing, sorting and dispensing medicaments. The smart dispensing tray is used in conjunction with a medicaments dispensing machine or system configured to hold or carry one or more trays. Each tray can store, sort and dispense one or more types of medicament, which may include pills, tablets, capsules, bottles and other uniformly sized articles.

Figure 1A:
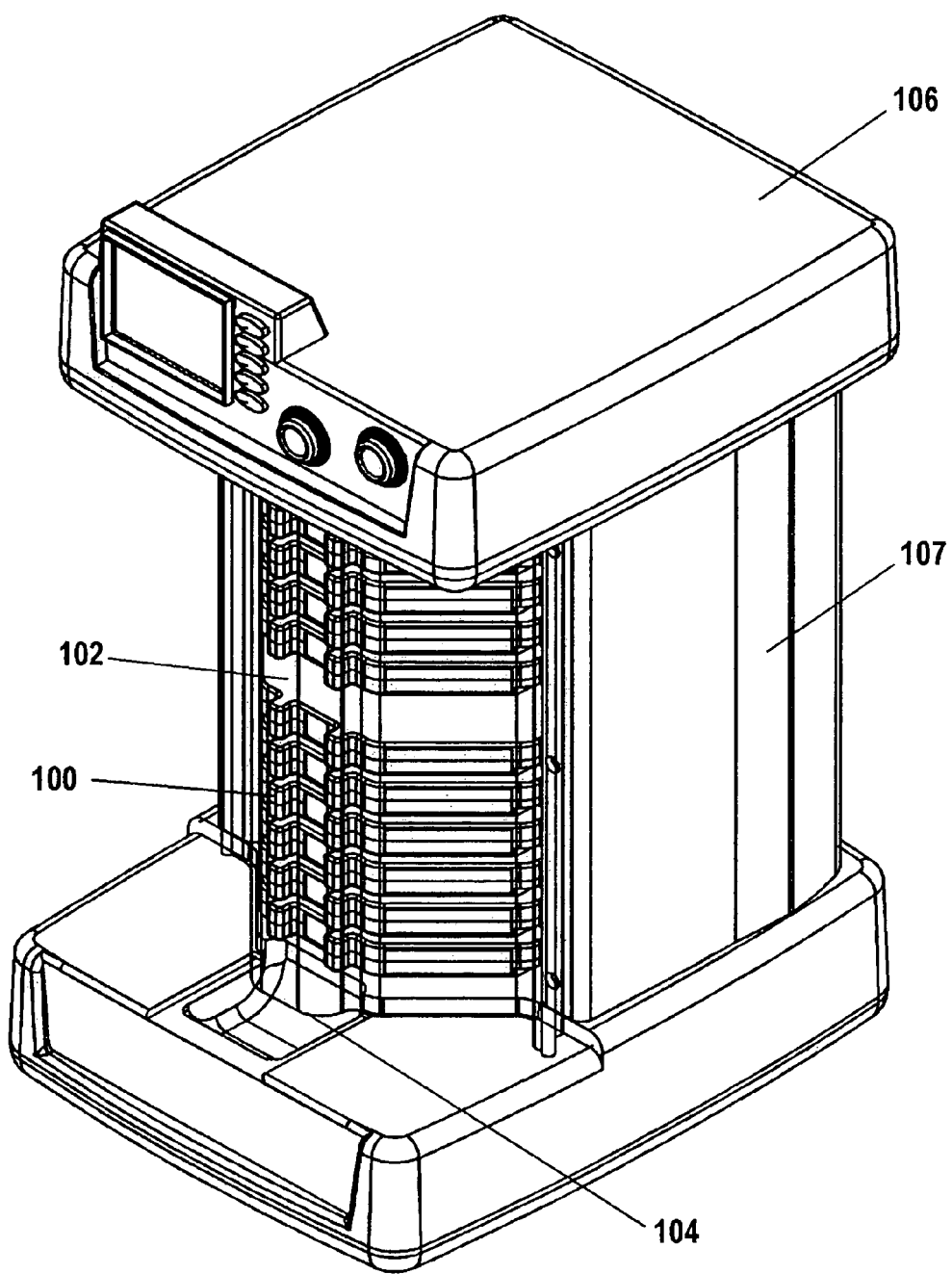
FIG. 1A is a perspective view of a medicaments dispensing machine for domestic use, in accordance with one embodiment of the invention.

FIG. 1A is a perspective view of a medicaments dispensing machine 106 which holds a plurality of medicament dispensing trays 100, in accordance with one embodiment of the invention. As shown in FIG. 1A, medicaments dispensing machine 106 comprises a vertical column in which several trays 100 may be inserted. Medicaments dispensing machine 106 may be used as a table top unit, may be mounted on a wall, under a kitchen cabinet or other desired positions. The vertical column of medicaments dispensing machine comprises a plurality of slots 102, where trays 100 may be inserted. In preferred embodiments, a tray 100 may be inserted in any available slot 102. As soon as a tray 100 is inserted in a slot 102, medicaments dispensing machine 106 automatically identifies the medicaments stored in tray 100 and tray 100 is automatically locked into the slot 102. These steps of automatically identifying the medicaments and locking the tray into slot 102 are discussed in further detail below with reference to FIGS. 4-6.

In another embodiment of the invention, medicaments dispensing machine 106 comprises a horizontal column having a plurality of vertically oriented slots configured to receive trays 100 therein. In one embodiment, trays 100 are configured to be inserted into a vertical or horizontal column of a dispensing machine 106 without any change in design of tray 100. In prior systems and trays, if a tray is not level or installed in a pre-specified orientation, such systems and trays are prone to jamming or malfunctioning because their sorting and dispensing mechanisms are not designed to operate in different orientations. Thus, as discussed in further detail below, the tray of the present invention provides a significant advantage in that it is designed to operate in various orientations while being less prone to getting jammed with medicaments or otherwise malfunctioning.

In one embodiment, medicaments dispensing machine 106 also comprises a see-through, shatter-proof door 104, which can be locked using an electronic lock, for example, to protect medicaments from theft or unauthorized dispensing. In a further embodiment, medicaments dispensing tray 106 comprises one or more biometric sensors for identifying authorized persons prior to dispensing medicaments and unlocks the electronic lock upon authorization. Biometric sensors for matching fingerprints with authorized fingerprint patterns stored in a memory, for example, are known in the art. Other types of biometric sensors such as voice recognition, retinal scanning, face recognition, etc., are also known in the art and may be utilized in the present invention.

Figure 1B:
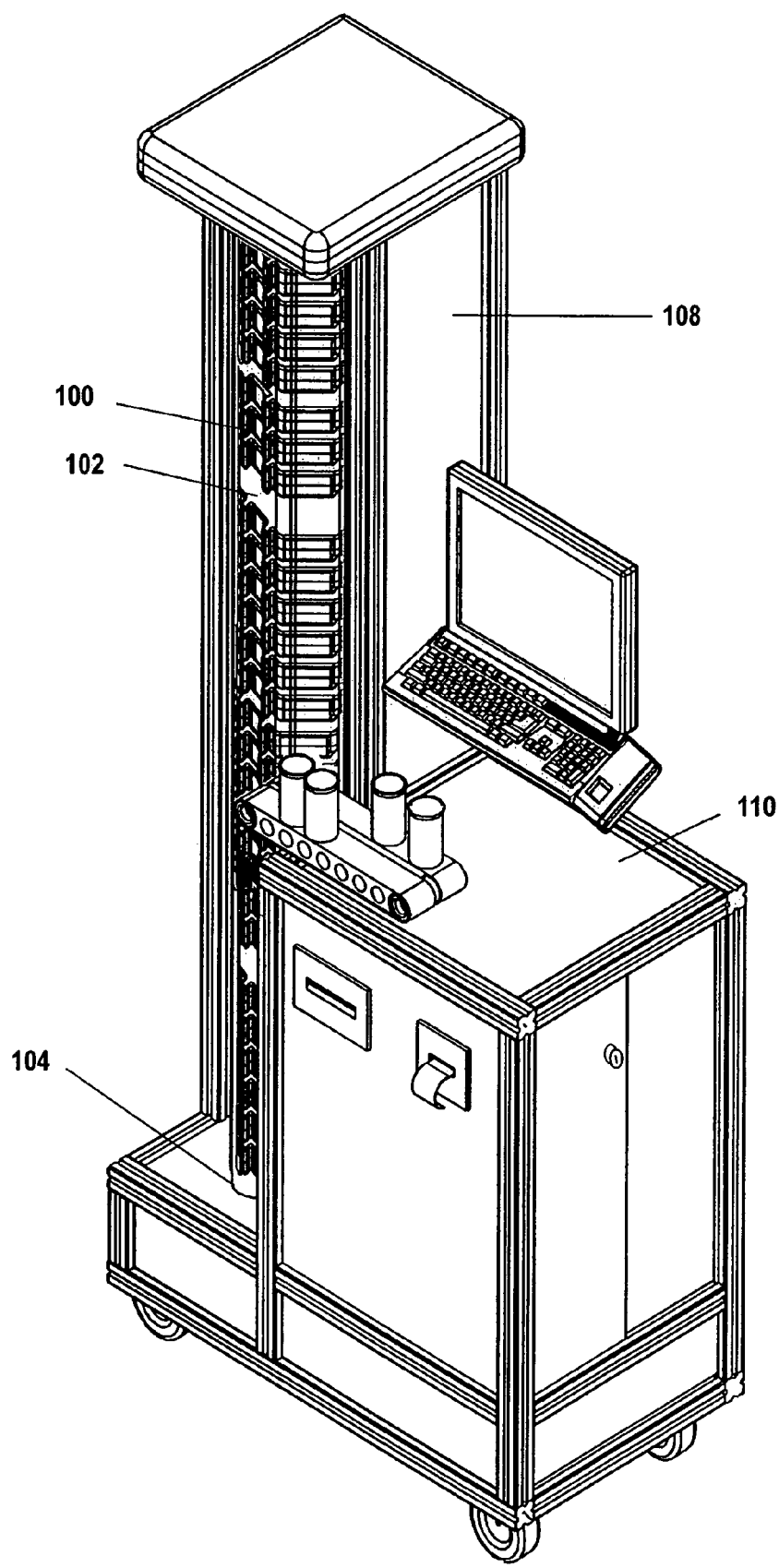
FIG. 1B is a perspective view of a medicaments dispensing machine for professional healthcare use, in accordance with one embodiment of the invention.

FIG. 1B is a perspective view of a medicaments dispensing machine 106 configured for use in a professional healthcare facility, in accordance with another embodiment of the invention. Such professional healthcare facility may be a medical practitioner's office, a nursing home, a hospital or other professional healthcare location. Medicaments dispensing machine 106 for professional healthcare use comprises a long vertical column 108 which can accommodate a large number of trays 100. Medicament dispensing machine 106 also comprises a secure storage cabinet 110 for storing an inventory of trays 100 for future use. The medicaments dispensing machine 106 further includes a computer 112 having a monitor/display and a keyboard. Via computer 112, a user can access, read and/or write data pertaining to one or more trays 100 held within the dispensing machine 106. Additionally, the computer 112 can upload information from a memory/data storage device (discussed in further detail below) contained within the tray 100, process sensor data (also discussed in further detail below) received from the tray 100, and also communicate with other network computers and devices to provide various functions. For example, if a central network computer (not shown) sends out a message recalling a certain type of medicament determined to be dangerous, the computer 112 can receive this information and upon communicating with a tray 100 containing the recalled medication, the computer 112 can disable dispensing of the medicament from that tray 100 and thereafter notify the central network computer of the status of tray 100.

Thus, via a computer network (e.g., the Internet), medicament dispensing machines dispersed in a wide geographic region may be monitored and intelligently controlled. This provides significant advantages in that medicament dispensing machines located in patient's homes as well as hospitals may be effectively monitored and controlled. As shown in FIGS. 1A and 1B, the medicaments dispensing machine 106 for home use (FIG. 1A) is a smaller and portable device, while medicaments dispensing machine 106 for professional healthcare use (FIG. 1B) is a taller device.

Figure 2:
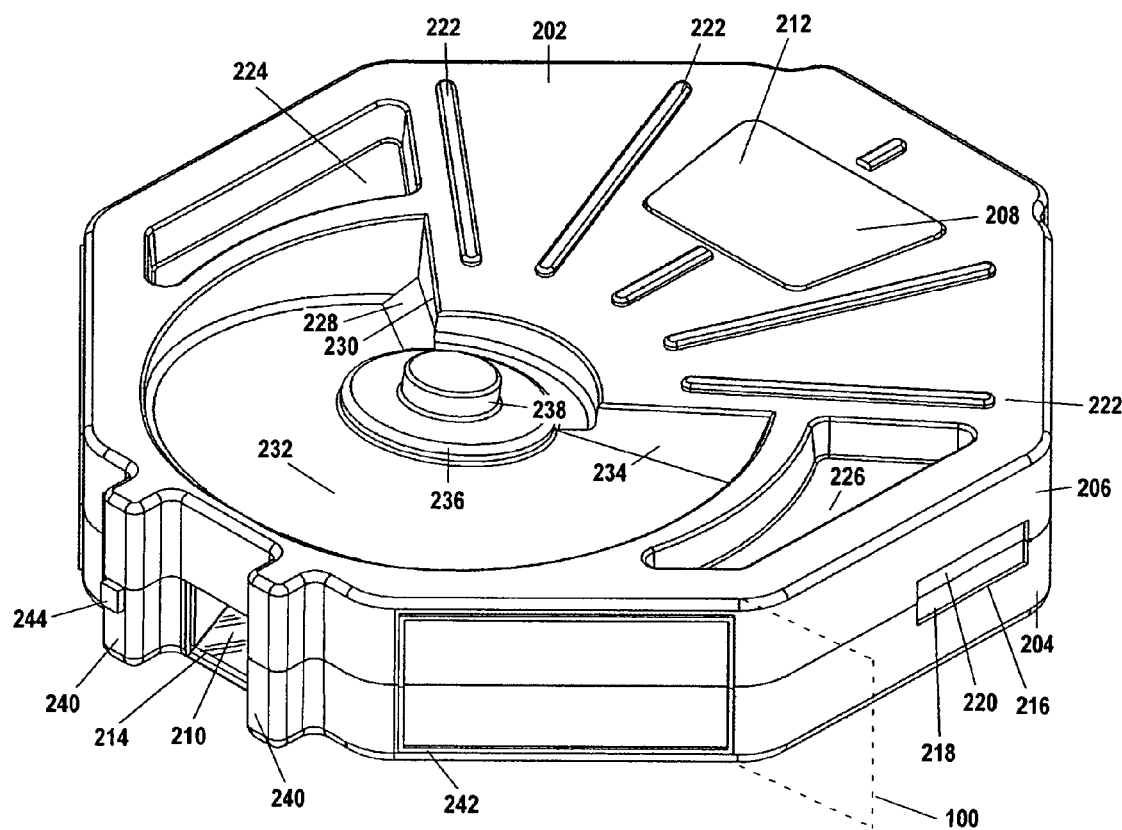
FIG. 2 is a perspective view of the tray illustrated in FIGS. 1A and 1B, in accordance with one embodiment of the invention.

FIG. 2 is a perspective view of tray 100 in accordance with one embodiment of the invention. The tray 100 comprises a plastic casing 202 made, for example, of a modified copolymer material, which is a tough, non-brittle and bio-friendly plastic. Further, this material possesses anti-static properties and has a UV-filtering capacity, which can extend the shelf life of medicaments stored within tray 100. Such materials are well known in the art and commercially available. For example, Provista Copolymer™ manufactured by Eastman Chemical Company may be utilized. This material has been tested so as to not produce toxic gases if burned in a fire. Additionally, this material has been demonstrated to be flame-retardant and, therefore, does not constitute an "exciter" for fires.

In one embodiment, casing 202 is made of two halves: a bottom casing 204 and an upper casing 206, which are hermetically sealed to each other. In a further embodiment of the invention, casing 202 has an octagonal shape (as shown in FIG. 2). Casing 202, however, may be configured in the shape of a square, circle, rectangle or any other desired shape. In the exemplary embodiment shown in FIG. 2, the dimensions of the tray are seven inches in diameter and three-quarters of an inch in height or thickness. Additionally, in one embodiment, the thickness of the casing walls 202 and 204 are 0.005 to 0.040 inches thick and reinforced with embossments 222 to provide additional strength and durability to the casing halves 202 and 204. The thinness of the casing walls in preferred embodiments allows the tray 100 to be manufactured more cheaply and efficiently. It is appreciated that the casing thickness is very thin for reducing the cost of materials and speeding up the rate of injection cycles of an injection molding process. In one embodiment, the shape, protrusions and/or depressions (e.g., the integral handle 240 and embossments 222) provided on the casing are engineered strengthening elements having a dual role of strengthening the casing and providing functionality to the operation of the smart tray. In one embodiment, the casing is made from a non brittle, anti static, fire retardant and bio-friendly plastic that does not produce harmful gases to humans in case of fire. In a further embodiment, the plastic provides ultra-violet (UV) and sun ray filtering to protect medications stored within the tray from the UV and sun ray exposure and prevent heat build-up inside the tray that can potentially damage the medicaments. Additionally, since the tray is bio-friendly, it can also be easily discarded in a waste dump or recycled for its materials.

Casing 202 further comprises an inlet 208 to load the medicaments in tray 100 and an outlet 210 to dispense the stored medicaments. A one-way snap door 212 closes inlet 208 and hermetically seals inlet 208. A self-sealing door 214 closes outlet 210. In one embodiment, door 214 is a spring-loaded door, which is kept closed by a spring (not shown) and is opened only at the time of dispensing a medicament. Casing 202 also comprises an opening 216 for admitting a rotational energy engagement mechanism or element such as drive gear into tray 100. The drive gear provides a driving force to a sorting and dispensing mechanism (discussed in further detail below with reference to FIG. 8), present within tray 100. As discussed below, this sorting and dispensing mechanism is used to dispense medicament units stored in tray 100.

In one embodiment, opening 216 is closed by a lower shutter 218 and an upper shutter 220 both of which are self-sealing spring loaded shutters. When tray 100 is inserted in the dispensing machine 106, shutters 218 and 220 open to allow an external rotational energy engagement element (e.g., a drive gear) to enter an internal compartment of tray 100 and engage an internal rotational energy engagement element (e.g. an internal drive gear), which is discussed in further detail below.

As mentioned above, in one embodiment, the outer surface of casing 202 comprises hollow embossments 222, which serve to strengthen casing 202. Embossments 222 also serve as guide-rails for a compression means (discussed in further detail below with reference to FIGS. 13A and 13B) inside tray 100. The surfaces of casing 202 and 204 further each comprise depression walls 224 and depression walls 226. In one embodiment, two depression walls 224 are provided at corresponding locations on casing half 202 and casing half 204 so as to provide support walls for desiccant and oxygen absorber canisters 1108 and 1110 (FIG. 11) inside tray 100. The chemical absorbers such as desiccants and oxygen absorbers are used to absorb moisture and oxygen from within tray 100, and thereby increase the shelf life of medicaments significantly and prevent stored medicaments from disintegrating and/or adhering to each other. Depression walls 226, also located at corresponding locations on casing halves 202 and 204 provide support for an engagement gear (discussed in detail below with reference to FIGS. 8 and 11) inside tray 100.

The top surface of casing 202 comprises a wall 228, a wall 230, a wall 232 and a wall 234. Wall 228 and wall 230 together form a double stepped wall that helps in filtering and sorting the medicaments. Wall 232 is a conical wall, which helps in guiding the movement of medicament units inside tray 100 while dispensing them. Wall 234 is a vertical wall that prevents the medicaments from entering into the sorting and dispensing mechanism inside tray 100 from the wrong direction. Hence wall 234 prevents the medicaments from jamming or back-filling into the sorting and dispensing mechanism. The top surface of casing 202 also comprises a projection 236 protruding outwards. Projection 236 prevents the medicaments from jamming in the central adjustment portion of the sorting and dispensing mechanism. Projection 236 further comprises a projection 238. Projection 238 includes an internally threaded wall that accommodates a top adjustment portion of the sorting and dispensing mechanism (discussed in further detail below). Because the top adjustment portion of the sorting and dispensing mechanism fits into projection 238, the sorting and dispensing mechanism is held in position inside tray 100.

As shown in FIG. 2, casing 202 comprises a pull handle 240 at the front end of tray 100. Pull handle 240 is used for manually handling tray 100 while inserting or removing tray 100 from the medicaments dispensing machine 106. In one embodiment, casing 202 further comprises a frame area 242, which acts as a location guide for holding a detachable coupon for displaying information concerning, for example, rebates, discounts or other advertising information. It is appreciated that allowing third parties to place human or machine readable advertisements and/or redeemable, detachable coupons in the frame area 242 will provide a revenue stream for manufacturers or vendors of the smart trays. In one embodiment, frame area 242 is formed of positive embossments, which also help in strengthening casing 202.

A multi-colored multi-functional display 244 is present on pull handle 240. In one embodiment, display 244 can display multiple different colors and/or characters. For example, display 244 changes colors and blinking status to indicate the working status of tray 100. Additionally, display 244 may show a solid green light to indicate that everything is working properly or a yellow light to indicate that tray 100 needs to be replenished soon. To indicate that tray 100 is empty, display 244 may flash a blinking red light. Thus, display 244 visually reports the status of tray 100.

Figure 3:
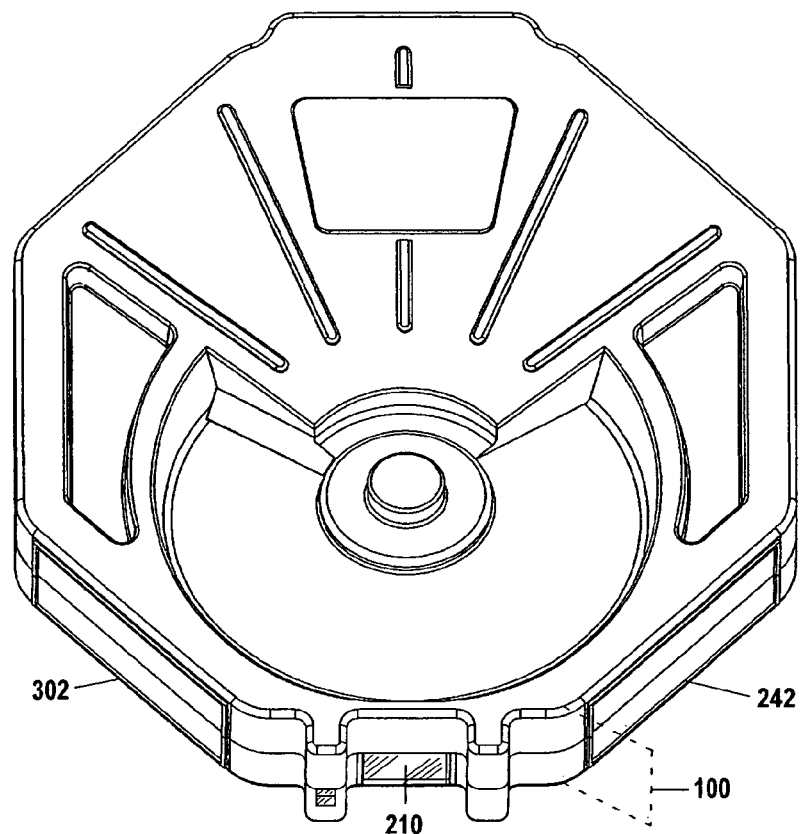
FIG. 3 is a front view of the tray illustrated in FIG. 2.

FIG. 3 is a front view of tray 100, which further shows a frame area 302 that provides space to attach a label (not shown). In one embodiment, the label contains information regarding the medicaments in tray 100 that are present on an ordinary medicine bottle. The information on the label includes, for example, medicament name, medicament type, usage instructions, medical practitioner name, patient name, batch number, manufacturer expiry date and other such information. The label may also include a bar code containing similar information. Frame area 302 is formed of positive embossments, which also help in strengthening casing 202.

Figure 4:
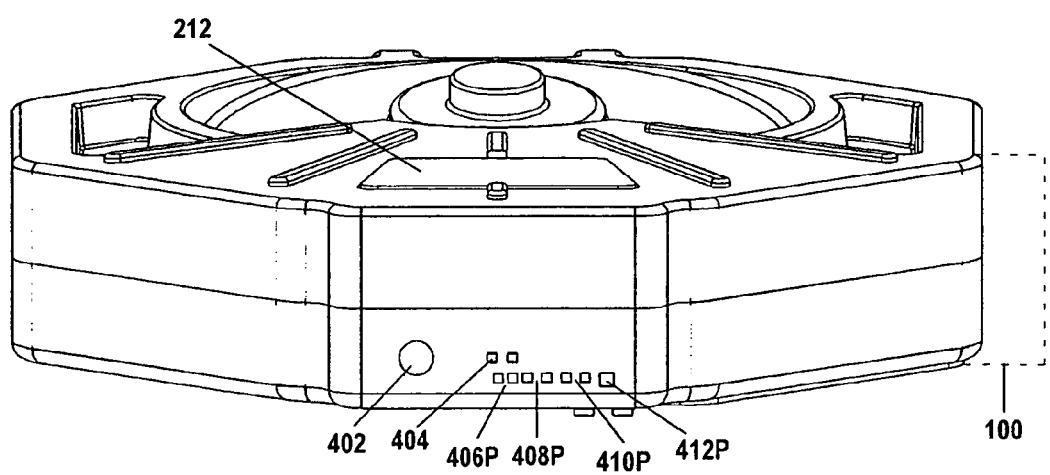
FIG. 4 is a back view of the tray illustrated in FIG. 2.

FIG. 4 is a rear view of tray 100. An alignment lock 402 is present on the back end of tray 100 in order to provide a self-alignment, auto-locking mechanism for tray 100 when inserted into a slot 102 (FIG. 1A) of a dispensing machine 106. In one embodiment, alignment lock 402 includes a ball pin that guides tray 100 into a slot 102 and then automatically aligns and snap locks tray 100 in place. Further, FIG. 4 shows two metallic contacts 404 that, in one embodiment, comprise two single wire serial communication links for communicating directly with optical sensors in the dispensing machine 106. These communication links also allow the circuitry within the smart tray to connect directly to, for example, an electronic network modem, to the dispensing equipment clock system, servo driver circuitry and database, or any other desired external circuitry to implement various desired functions as described herein. It is understood that any suitable programmable and readable non-volatile memory or data storage device may be used in the tray 100. In one embodiment, alignment lock 402 can be made of a conductive material and function as a ground pin. Thus, the metallic contacts 404 and the alignment lock 402 provide a three-contact interface for communicating with circuitry/devices in the dispensing machine 106.

In further embodiments, an electromagnetic field communication device such as a wireless communication device (not shown) may be alternatively or additionally employed in the tray 100 to store and communicate information pertaining to stored medicaments to the dispensing machine and enable various functionalities in accordance with the present invention. Exemplary types of information that may be stored in the wireless communication device and/or other memory device are described in further detail below with reference to FIGS. 17A-18C. Thus, information stored within each tray 100 pertaining to the medicaments stored therein can be automatically provided to the automatic medicament dispensing machine 106 by direct wired contacts to a memory device within tray 100 and/or via electromagnetic transmission such as radio frequency transmission between a wireless communication device within the tray 100 and corresponding reader circuitry, hardware and software within the medicament dispensing machine 106 and/or other external devices. Various types of electromagnetic communication devices (e.g., RFID tags, smart cards, infrared, Bluetooth devices, other two-way full-duplex electromagnetic field communication devices, etc.) and corresponding readers, which may be used in the present invention, are known in the art. As used herein, electromagnetic communication refers to both wired and wireless communication and includes the entire range of electromagnetic radiation, which includes frequencies of $10^{23}$ cycles per second to 0 cycles per second, and wavelengths from $10^{-13}$ centimeters to infinity. From the lowest frequency to the highest (or the longest wavelength to the shortest) the spectrum includes electric current, heat, radio waves, microwaves, infrared radiation, visible light (colors), ultraviolet radiation, X-rays, gamma rays, and cosmic-ray photons.

Figure 8:
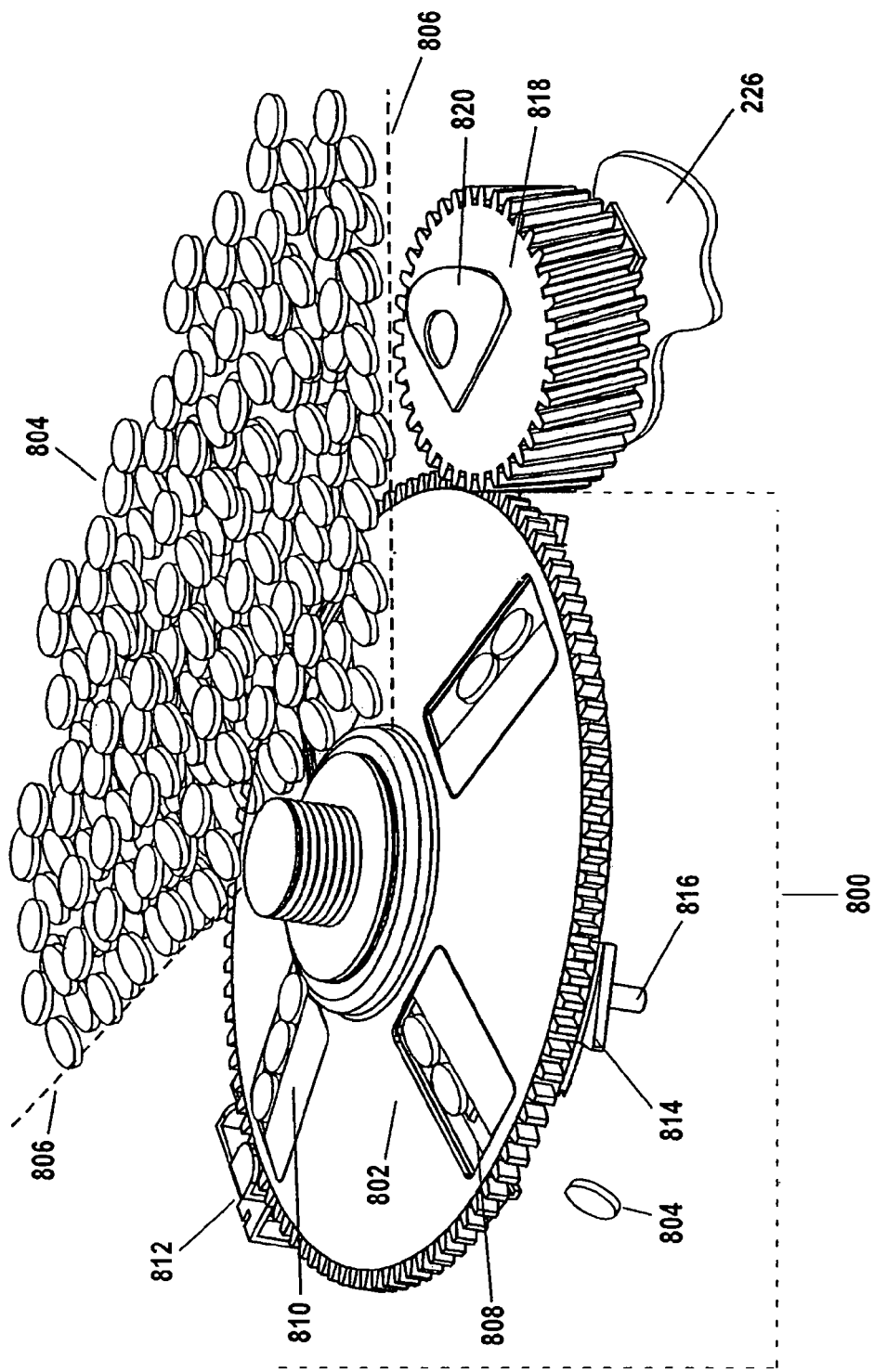
FIG. 8 is a perspective view of a sorting and dispensing mechanism, in accordance with one embodiment of the invention.
Figure 9:
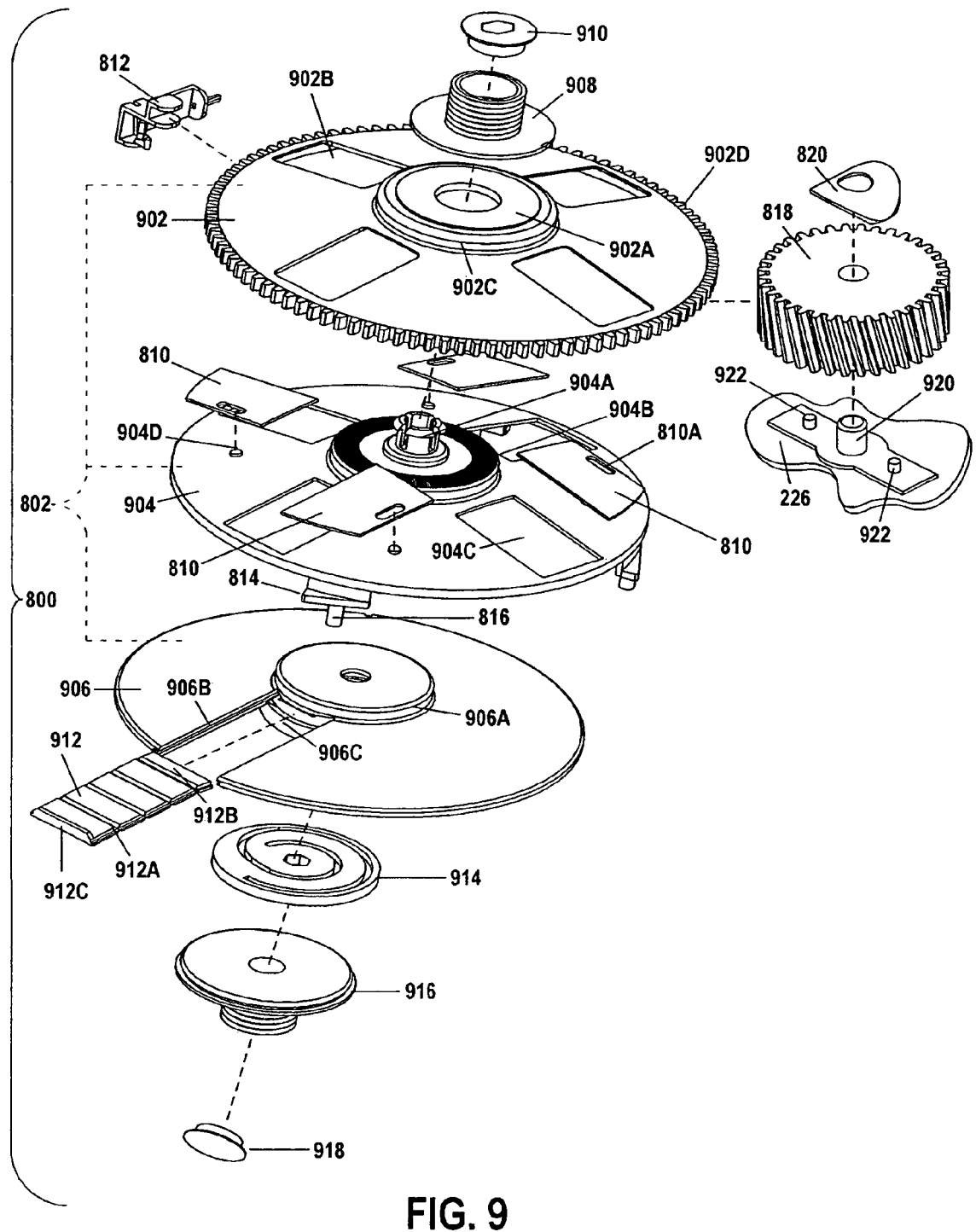
FIG. 9 is an exploded view of the sorting and dispensing mechanism illustrated in FIG. 8.

FIG. 4 also shows a plurality of electromagnetic communication ports for communicating with external device that can be coupled to one or more of the ports. In one embodiment, these ports comprise fiber optic ports 406P, 408P, 410P and 412P, which hold one end of a fiber optic cable. The other of the fiber optic is located within the tray to analyze either contents of the tray or monitor operation of the tray (as discussed in further detail below). In one embodiment, each end of each fiber optic cable comprises molded or shaped optic lens (e.g., a plano-convex lens) for focusing the electromagnetic field for optimal operation. Such molded or shaped optic lens are known in the art. In one embodiment, port 406P connects the medicaments dispensing machine 106 to a fiber optic cable (discussed in further detail below with reference to FIG. 15) that checks the positioning and functioning of tray 100. Port 408P connects the medicaments dispensing machine 106 to a second fiber optic cable that connects to an electromagnetic reading device such as a scanner (discussed below with reference to FIGS. 12A and 12B). In various embodiments, the scanner can function as a bar code scanner and/or as a spectrometer that identifies the color, shape and/or size of the medicament units while they pass through the sorting and dispensing mechanism 800 (FIGS. 8 and 9). The scanner can therefore check and verify the authenticity of the medicaments stored in tray 100. Port 410P connects the medicaments dispensing machine 106 to a third fiber optic cable that connects to a second scanner (discussed below with reference to FIG. 15) at outlet 210, which checks the color, size, shape and/or chemical composition of the medicaments at the time of dispensing. As used herein, the term "scanner" refers to an electronic device that detects or scans for some signal, condition or physical characteristic.

In preferred embodiments, ports 406P, 408P and 410P connect to sensors present in medicaments dispensing machine 106. These sensors include color sensors and spectrometer sensors that are not only capable of detecting the color, shape and/or size of the medicament units but are also capable of detecting a counterfeit medicine by comparing sensed data to data stored in a memory device within the smart tray 100. In other embodiments, the data stored in the memory device in the smart tray is uploaded to memory, e.g., RAM, (not shown) within the medicament dispensing machine 106. Port 412P connects circuitry within the medicaments dispensing machine 106 to a fourth fiber optic cable (discussed below with reference to FIG. 15) that connects to display 244. Thus, circuitry within the medicament dispensing machine 106 and/or the smart tray 100 can control operation of the display 244. Alignment lock 402 ensures correct alignment between the drive gears and fiber optic connections of the tray 100 with corresponding structures/contacts in the dispensing machine 106.

Figure 5:
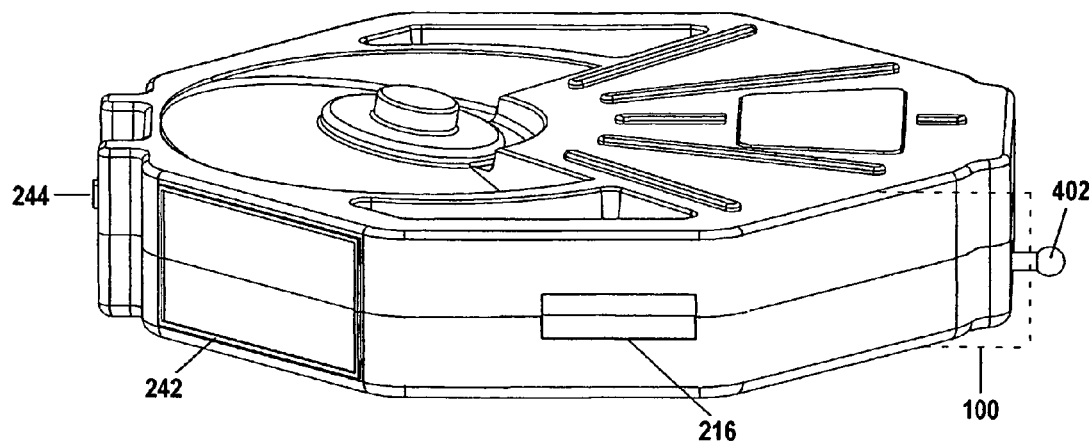
FIG. 5 and FIG. 6 are side views of the tray illustrated in FIG. 2.
Figure 6:
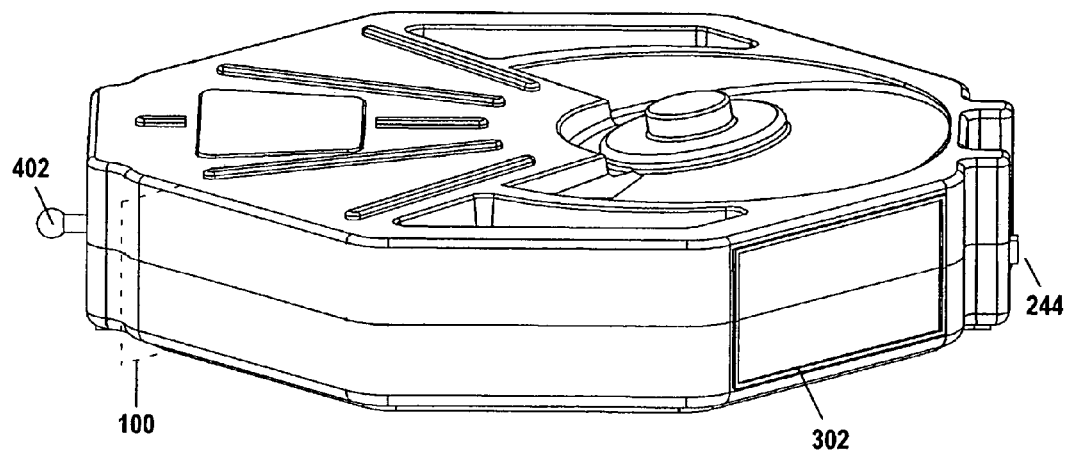

FIGS. 5 and 6 illustrate side views of tray 100 and further show LED display 244 present on the front end of tray 100 and the alignment lock 402 present on the back end of tray 100. FIG. 5 also shows the position of frame area 242 and opening 216 as visible from a right side of tray 100 while FIG. 6 shows frame area 302, as viewed from a left side of tray 100.

Figure 7:
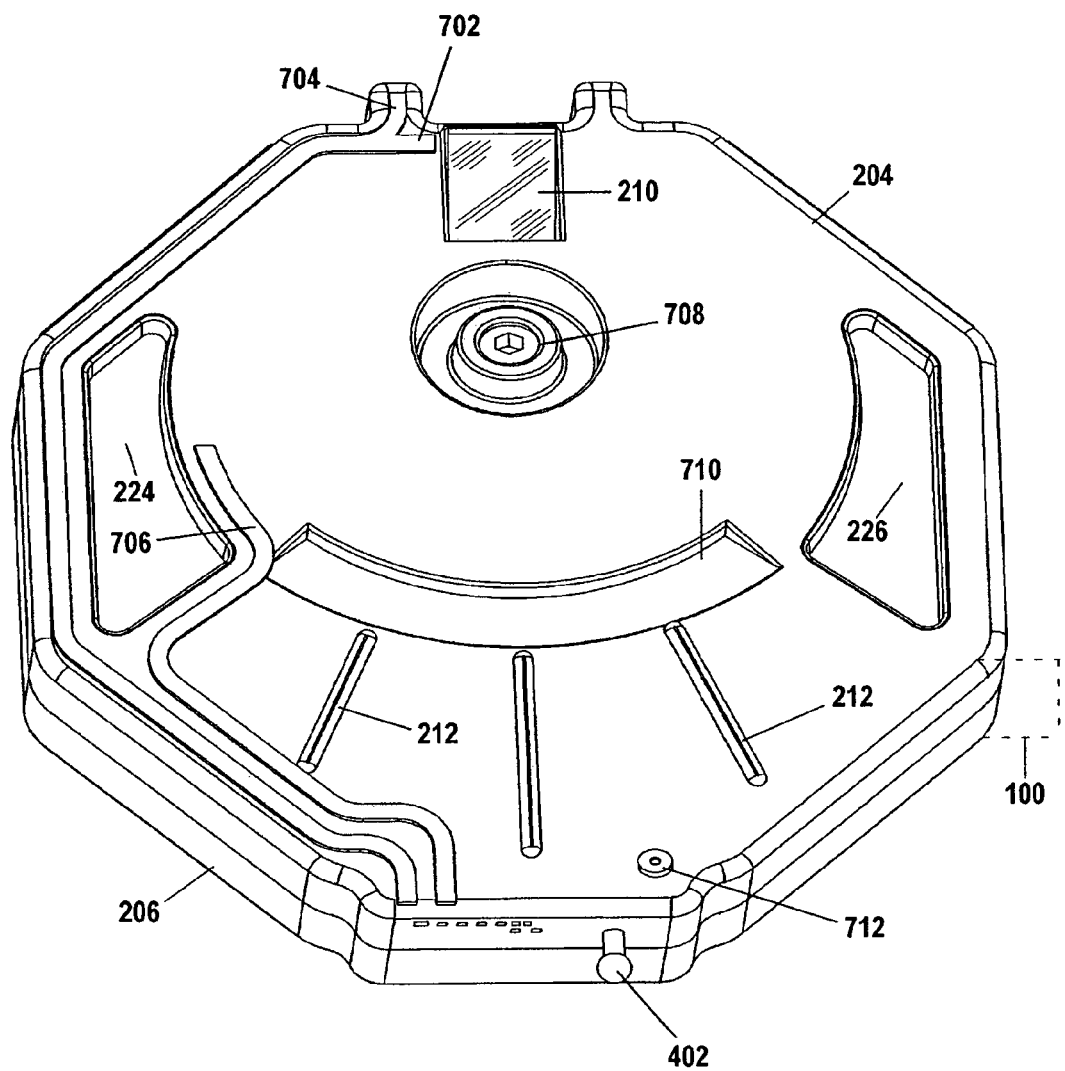
FIG. 7 is a bottom view of the tray illustrated in FIG. 2.

FIG. 7 illustrates a bottom view of tray 100 that further shows embossments 222 on a bottom side of casing 204. The bottom side of casing 204 has a channel 702 for the third fiber optic cable that connects to the scanner at outlet 210. Hence, each medicament unit being dispensed can be viewed from port 410P through the fiber optic cable in channel 702. Channel 704 holds the fourth fiber optic cable, which connects port 412P to display 244. As shown in FIG. 7, channels 702 and 704 merge together to form a single channel. The casing 204 further comprises a channel 706 that holds the first and second fiber optic cables, which connect to ports 406P and 408P, respectively. FIG. 7 also shows an opening 708 at the bottom of casing 202, through which a bottom portion of the sorting and dispensing mechanism 800 is exposed outside casing 202. As discussed in further detail below, opening 708 is used to adjust the spacing of structures within the sorting and dispensing mechanism in accordance with the shape and size of the medicament being dispensed.

The bottom surface of casing 202 further comprises an indented portion or depression 710, which forms an internal protrusion that functions as a loading ramp on an inner surface of casing 202 for loading of medicaments into the sorting and dispensing mechanism 800. A one-way valve 712 is present on the bottom surface of casing 202 and provides an inlet for air or other gas for expanding a compressible medium, air bag or bellow within the storage compartment of the tray 100 in order to push medicament units into the sorting and dispensing mechanism 800. Alternatively, in other embodiments, the compressible medium may be a spring-loaded mechanism for exerting a pressure on the medicaments in a desired direction. The compressible medium (1) serves to load medicaments into the dispensing portion of the tray and (2) stabilizes movement of medicaments within the tray during transit, which helps prevent breakage or chipping of the medicaments (e.g., pills).

FIG. 8 is a perspective view of the sorting and dispensing mechanism 800 in accordance with one embodiment of the invention. The sorting and dispensing mechanism 800 comprises a conical disk assembly 802, which further comprises a gear-toothed periphery. Medicament units 804 are stored in a storage portion of tray 100. The surface walls of tray 100 and a wall 806 formed within tray 100 define the storage portion of the tray 100. Wall 806, the boundaries of which are illustrated by dashed lines 806, prevents medicament units 804 from entering into sorting and dispensing mechanism 800.

The conical disk assembly 802 further comprises radial grooves 808 for receiving and carrying medicament units from the storage portion to an outlet 210. Although in the exemplary embodiment shown in FIG. 8, four radial grooves are illustrated, any desired number of such radial grooves may be incorporated in the conical disk assembly 802. In one embodiment, grooves 808 have an adjustable size, which can be changed according to the shape and size of medicament units 804. A slidably fitted door 810 is present along each groove 808 so as to maintain a desired size and shape of groove 808, as well as maintain the parallel configuration of the adjustable opening or groove to accurately control sorting and alignment of the medicaments during dispensing. This permits only one pill to be dispensed at a time and allows more accurate counting and analysis of each pill that is dispensed.

In one embodiment, conical disk assembly 802 is made of clear plastic. Therefore, the medicament units present in grooves 808 are more easily visible to a scanner 812 present at the periphery of conical disk assembly 802. Additionally, as described in further detail below, the rotating disks 902 and 904 are set apart from one another by a predetermined distance (e.g., 50% of the height of medicament unit) so that a space is provided between the disks 902 and 904. Through the space between the disks 902 and 904, the scanner 812 can directly view at least a portion of the radial side surfaces of medicament units contained in the groove 808 as they are being transported to the outlet 210. In this way, scanner 812 can identify the color, shape, size and/or chemical composition of the medicament units present in grooves 808 and can also identify barcodes or other marks present on the medicament units 804. Scanners or other electromagnetic reading devices capable of performing the types of functions of scanner 812 are well known and commercially available.

Conical disk assembly 802 further comprises one or more latches 814 adjacent to each groove 808. When conical disk assembly 802 rotates to dispense a single unit of medicament, latch 814 interacts with scanner 812 to make it scan the groove 808 and any medicament units contained therein, as described in further detail below with reference to FIG. 9. Furthermore, a projection 816 extends downwardly from each latch 814 for facilitating the opening of door 214 (FIG. 2) when a medicament unit 804 is being dispensed by tray 100.

An idler gear 818 is present inside casing 202 that provides engagement of the gear teeth present on the periphery of conical disk assembly 802 to a drive gear in the medicaments dispensing machine 106. Idler gear 818 provides drive force for rotating the sorting and dispensing mechanism 800. A compressible medium or mechanism such as a spring washer 820 presses idler gear 818 downwards and provides a locking mechanism for idler gear 818 as described in further detail below.

FIG. 9 is an exploded view of the sorting and dispensing mechanism 800. Sorting and dispensing mechanism 800 comprises a conical disk assembly 802 (FIG. 8), which further comprises two rotatable conical disks 902 and 904, and a stationary conical disk 906. Conical disk 902 and conical disk 904 are free to rotate on a central axis and are therefore referred to as rotatable conical disks. Conical disk 904 comprises a snapping mechanism 904A that passes through the center of conical disk 902 and snaps into a threaded cap 908. Snapping mechanism 904A holds conical disk 902 and conical disk 904 together. Furthermore, conical disk 904 comprises a gear-toothed surface 904B on a top surface of the conical disk 904. Conical Disk 902 also comprises a similar gear-toothed surface (not shown) on the bottom of the surface designated as 902A of conical disk 902.

Two embodiments of gear-toothed surfaces 902A and 904B are illustrated in FIGS. 14A and 14B. Gear-toothed surface 902A and gear-toothed surface 904B engage each other such that conical disk 902 and conical disk 904 rotate together in unison. It is understood that the gear-toothed drive mechanism described above is exemplary only and other types of rotational energy engagement elements or mechanisms may also be employed in accordance with the invention. For example, a belt drive assembly or a custom configured transmission system, similar to those implemented in automobiles, may be implemented by those of ordinary skill in the art without undue experimentation. Alternatively, or additionally, magnetic coupling engagement mechanisms or drive assemblies may also be employed in accordance with the invention.

Sorting, separating and dispensing mechanism 800 further includes an end cap 910, which snaps into cap 908 to hermetically seal the dispensing mechanism enclosure. Cap 908 and cap 910 are accommodated in projection 238 (FIG. 2) in casing 202. Threads on the inner surface of projection 236 match with the threads on cap 908.

The distance between conical disk 902 and wall 232 (FIG. 2) can be adjusted by rotating disk assembly 802 and moving cap 908 up and down along the threads of projection 236. In one embodiment of the invention, the distance between conical disk 902 and wall 232 is adjusted equal to 70% of the height of medicament units 804. Further, the distance between conical disk 904 and conical disk 906 is adjusted to 50% of the height of the medicament units 804. In one embodiment, when medicament units 804 are being sorted in grooves 808, conical disks 902 and 904 are set apart by approximately 50% of the height of medicament units 804. Further, there is a space of at least 20% of the height of medicament units 804 between the wall 232 and medicament units 804 when they are positioned within grooves 808. This prevents jamming of medicament units 840 in sorting and dispensing mechanism 800. The adjustment of the height of conical disk 906 within casing 202 is discussed in further detail below.

A radial groove 902B and a radial groove 904C are present on conical disks 902 and 904 respectively, corresponding to each of the grooves 808 shown in FIG. 8. Each of the doors 810 have a groove or slit 810A for receiving therein corresponding pins 904D present on the top surface to conical disk 904. A door-guiding rail is present on the bottom of conical disk 902 (not shown) corresponding to each of the doors 810 such that the doors 810 slide on pins 904D and are guided by the door-guiding rails to maintain a consistently parallel rectangular groove 808 as shown in FIG. 8. The width of grooves 808 can be adjusted by twisting conical disk 902 with respect to conical disk 904 such that the width of the grooves 808 is adjusted substantially equal to the diameter of medicament units 804.

In one embodiment of the invention, conical disk 902 and conical disk 904 rotate in an anti-clockwise direction (as viewed from the top). When conical disk 902 and conical disk 904 rotate while carrying medicament units 804 in grooves 808, the double stepped wall, formed of wall 228 and wall 230, assist in sorting medicament units 804 and prevents them from jamming in the sorting and dispensing mechanism 800. Wall 234 on the other hand prevents medicament units 804 from entering into sorting and dispensing mechanism 800 from the wrong direction.

Conical disk 906 remains stationary throughout the dispensing of medicament units 804. Conical disk 906 provides surface support for medicament units in grooves 808 that are dragged as conical disk 902 and conical disk 904 rotates. As shown in FIG. 9, conical disk 906 comprises a projection 906A at the center of conical disk 906, which provides alignment to conical disk 906 with conical disks 902 and 904. Conical disk 906 further comprises a slot 906B that further comprises guiding rails or channels on opposite sides of the slot 906B for accommodating a "living hinge" 912. Living hinge 912 comprises several rectangular pieces attached to each other through living hinge connections 912A, which provide flexibility to living hinge 912. The top surfaces of the rectangular pieces of the living hinge 912 are substantially planar with the top surface of the conical disk 906 so as to prevent jamming of medicament units that pass over the living hinge as the disks 902 and 904 rotate. Living hinges are well-known in the plastic industry.

Figure 10:
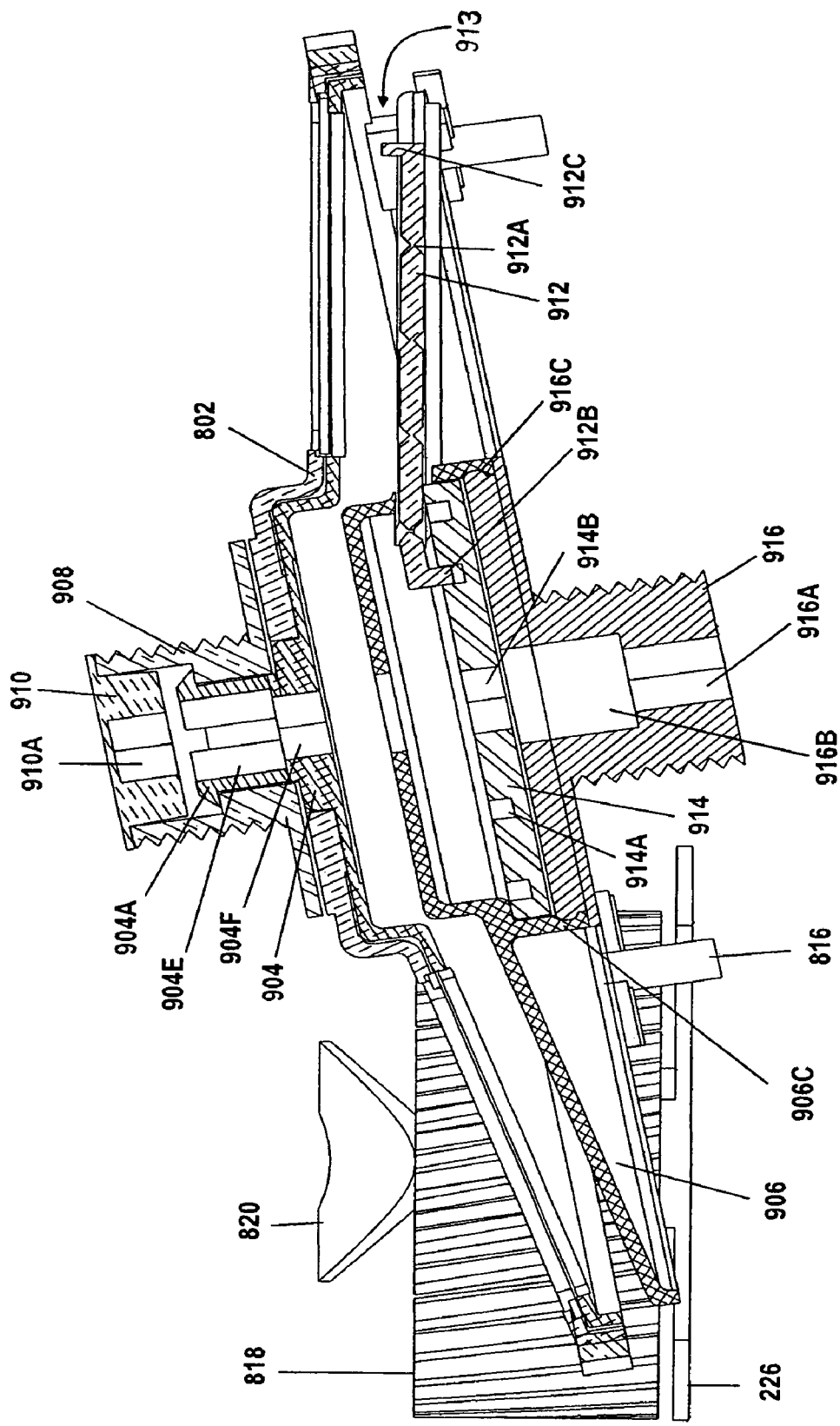
FIG. 10 is a cross-sectional view of the sorting and dispensing mechanism illustrated in FIG. 8.

A pin (not shown) is present at the bottom surface of the rectangular piece 912B which is closest to the center of conical disk 906 (shown in better detail in FIG. 10). The pin extending downwardly from rectangular piece 912B fits into a spiral groove present on the top surface of a disk 914. Disk 914 snaps into a snapping mechanism 906C present at the bottom of the conical disk 906. When disk 914 is rotated, the pin moves in or out in a radial direction following the spiral groove on the disk 914. The length of living hinge 912 may therefore be adjusted by rotating disk 914. Furthermore, living hinge 912 comprises a small stopper 912C at an opposite end of the living hinge 912. In one embodiment of the invention, the length of living hinge 912 is adjusted such that the space between stopper 912C and the diameter of conical disk 906 is equal to 70% of the length of medicament units 804. This allows dispensing of only one medicament unit 804 when groove 808 reaches the slot 906B. The stopper 912C pushes upwardly and tilts a pill contained at a radial, outermost portion of the groove 808 so that the pill falls out an exit aperture 913 and into outlet 210 (FIG. 2). Thus, as shown in FIG. 10, by adjusting the position of stopper 912C within the tray 100, the size of the exit aperture 913 may be adjusted so as to allow the dispensing of only one pill at a time. Stopper 912C also prevents medicament units 804 from sliding down the living hinge 912 into outlet 210. It is appreciated that the accurate dispensing of only a single pill at a time allows for accurate counting, dispensing and monitoring of inventory of medicament units.

Snapping mechanism 906C further snaps into a threaded cap 916 and holds conical disk 906, disk 914 and threaded cap 916 together. The threads present on the outer surface of cap 916 engage with threads present on the inner surface of casing 202. The entire assembly comprising conical disk 906, disk 914 and cap 916 may therefore be moved up or down by rotating cap 916. In one embodiment, the height of the entire assembly comprising conical disk 906, disk 914 and cap 916 is adjusted such that the distance between conical disk 906 and conical disk 904 is equal to 50% of the height of medicament units 41. A cap 918 snaps into cap 916 to provide hermetical sealing of tray 100.

Idler gear 818 rotates on a cylinder 920, which is attached to a lower wall of casing 202. Furthermore, small cylinders 922 are present on the lower wall of casing 202 that fit into matching grooves (not shown) present on the lower surface of idler gear 818. When cylinders 922 engage in the grooves present on the lower surface of idler gear 818, idler gear 818 is locked and cannot rotate. In this way, the tray is "locked" when it is not positioned within a dispensing machine 106 so as to provide security against tampering and theft of medicaments stored in the tray. The drive gear 902D present in the tray 100, engages the gear teeth of idler gear 818. As shown in FIG. 9, the gear teeth of idler gear 818 are configured at a specified angle so as to provide a lifting force when engaged by an external gear (not shown) provided by medicament dispensing machine 106. Thus, in addition to providing a rotating force to the idler gear 818, the external drive gear provides a lifting mechanism for idler gear 818. This lifting mechanism disengages idler gear 818 from the locking mechanism provided by cylinders 922, thereby allowing the idler gear 818 to engage and rotate the drive gear 902D within the tray 100. In one embodiment, the idler gear 818 is a helix gear, which is a well-known type of gear for providing a quiet rotational drive element. Thus, in one embodiment, the smart tray of the present invention reduces operational noise and minimizes potential disturbance to nearby patients or caregivers.

FIG. 10 illustrates a cross-sectional view of the sorting and dispensing mechanism 800, in accordance with one embodiment of the invention. Cap 910 comprises an axial receptacle 910A (e.g., an Allen key receptacle), which adjusts the height of cap 910. A similar receptacle, receptacle 904F is present at the center of conical disk 904 for adjusting the height of cap 904. Disk 914 comprises a spiral groove 914A and an axial receptacle 914B. The pin which extends downwardly from rectangular piece 912B of the living hinge 912 fits in groove 914A, and as disk 914 is rotated, the pin is moved radially inwardly or outwardly. Receptacle 914B provides space for rotating disk 914 and therefore facilitates adjusting the length of living hinge 912. Cap 916 further comprises an axial receptacle 916A, which helps in rotating cap 916. Receptacle 916A therefore facilitates adjusting the height of conical disk 906.

In one embodiment, to accommodate high-speed adjustment of the smart tray in accordance with the size and shape of the particular medicament units to be stored within the tray, all adjustments may be performed at one central location of the tray using only one engagement key. In order to adjust the levels of all components of the conical disk assembly, an engagement key (e.g., an Allen key or slot key) is inserted into the conical disc assembly through receptacle 916A such that the key passes through receptacles or spaces 916B, 914B, 904F, 904E and 910A. Firstly, adjustment of the height of cap 910 is made by rotating the engagement key in receptacle 910A. Subsequently, the engagement key is pulled away from receptacle 910A such that an end of the engagement key is positioned within an empty space 904E. The engagement key is then aligned such that it may be pulled into and received by key receptacle 904F. Thereafter the engagement key is rotated in receptacle 904F in order to adjust the height of conical disk 904. Once the height of conical disk 904 is adjusted, the engagement key is realigned to receptacle 914B and is pulled into receptacle 914B. The engagement key is rotated in receptacle 914B to adjust the length of living hinge 912. Subsequently the engagement key is pulled into an empty space 916B and rotated in empty space 916B so that it aligns with receptacle 916A. The engagement key is then pulled into receptacle 916A and the last adjustment is made by rotating the engagement key in receptacle 916A, in order to adjust the height of conical disk 906.

Figure 11:
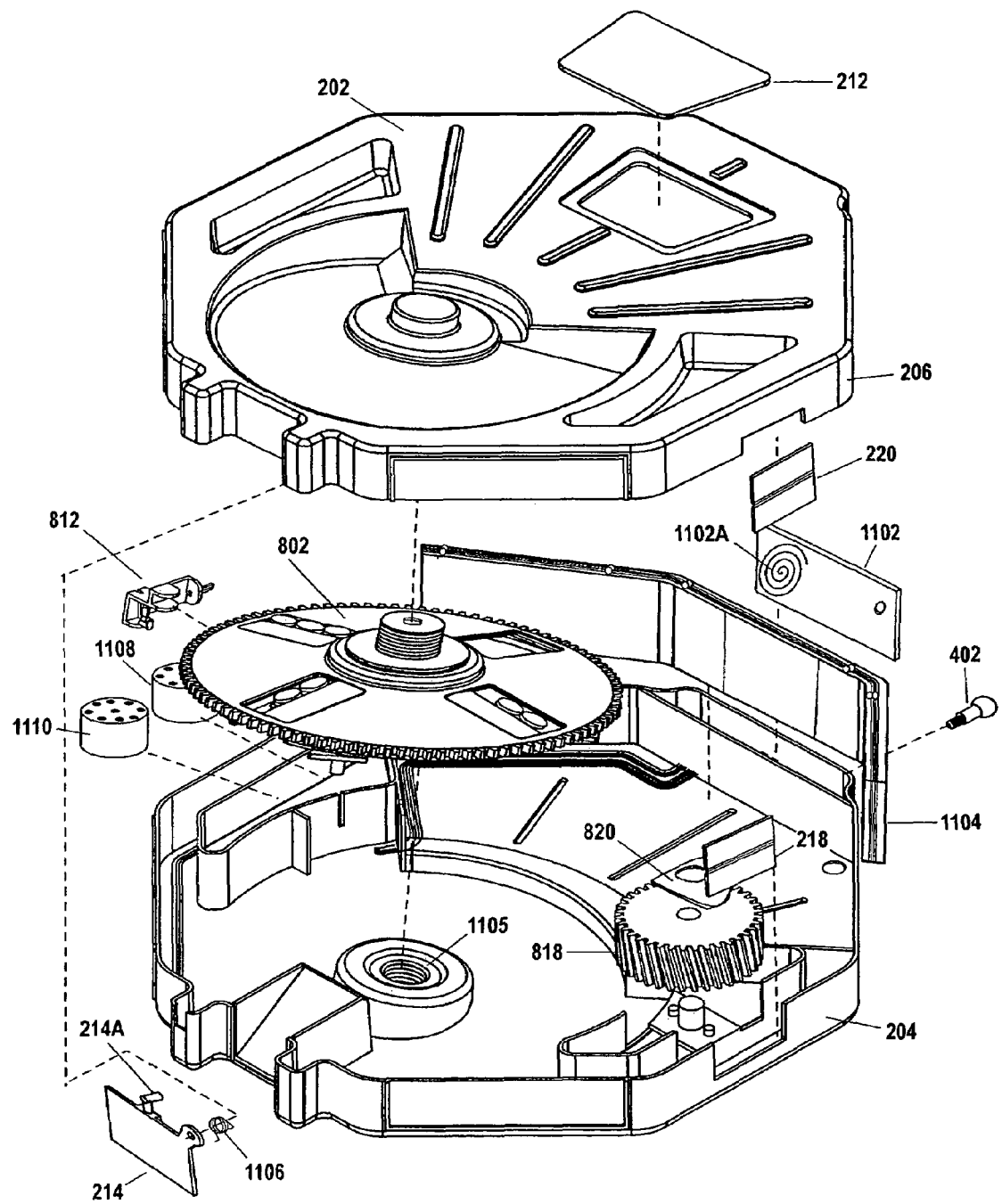
FIG. 11 is an exploded view of the tray illustrated in FIG. 2, in accordance with one embodiment of the invention.

FIG. 11 is an exploded view of the medicaments dispensing tray 100, in accordance with one embodiment of the invention. The sorting and dispensing mechanism 800 is positioned within casing 202 of the tray 100. Tray 100 further comprises an electromagnetic communication device 1102, which has a memory/data storage device and the ability to communicate data to other devices. Further details regarding the information that may be stored in the memory/data storage device of electromagnetic communication device 1102 are provided below with reference to FIGS. 17 and 18. It is understood that any type of suitable data storage device or reprogrammable electron valve device (e.g., any device capable of controlling the storage and flow of electrons) may be utilized to store information in accordance with the present invention.

Electromagnetic communication device 1102 is capable of electromagnetic communication with other devices such as RFID or smart card readers, infrared and/or other circuitry (not shown) within medicaments dispensing machine 106. Tray 100 may be located and identified using electromagnetic communication device 1102, for example, in a shelf in a pharmacy or during transportation. Electromagnetic communication device 1102 further comprises an antenna 1102A for enhancing the communicating ability of tray 100. Many types of electromagnetic communication devices and corresponding readers are known in the art such as RFID tags, smart cards, Infrared, Bluetooth devices, etc., and their corresponding readers.

Shutter 218 and shutter 220 that fit in bottom casing 204 and top casing 206 respectively are also shown in FIG. 11. Shutter 218 and shutter 220 are pressure or spring-loaded doors that cover opening 216 (FIG. 2). As discussed above, opening 216 is used for engagement of idler gear 818 with the drive gear inside medicaments dispensing machine 106.

FIG. 11 further shows a compressible medium, air bag or bellow 1104 (in its compressed state) that pushes medicament units 804 towards sorting and dispensing mechanism 800. Further details regarding the air bellow 1104 are provided below with reference to FIGS. 13A and 13B. FIG. 11 further shows threads 1105 on the bottom surface of casing 202 that accommodates cap 916 (FIG. 9). It should be noted that threads 1105 present on the bottom surface of casing 202 are inclined at a certain angle. In one embodiment of the invention, wherein tray 100 is being used for dispensing small tablets, the axis of the conical disk assembly makes an angle of 10 degrees from the vertical.

Door 214 present at outlet 210 comprises a spring 1106 that keeps door 214 closed when medicament unit 804 is not being dispensed. When medicament unit 804 is being dispensed, projection 816 present on conical disk 904 (FIG. 9) interacts with a projection 214A on door 214 to push open the door. Further, FIG. 11 shows chemical (e.g., oxygen) absorber canisters 1108 and desiccant canisters 1110 present inside tray 100. Chemical absorbers 1108 are typically in the form of bags or sachets containing chemical compounds, the active ingredient of which is powdered iron oxide. For example, oxygen absorbers bring the oxygen level in tray 100 down to 0.01% or less. Such oxygen absorbers are well known in the art and are made available by vendors like SorbentSystems™. Oxygen absorbers 1108 and desiccants 1110 are present under the depression 224 on the top surface of casing 202, as shown in FIG. 2.

Figure 12A:
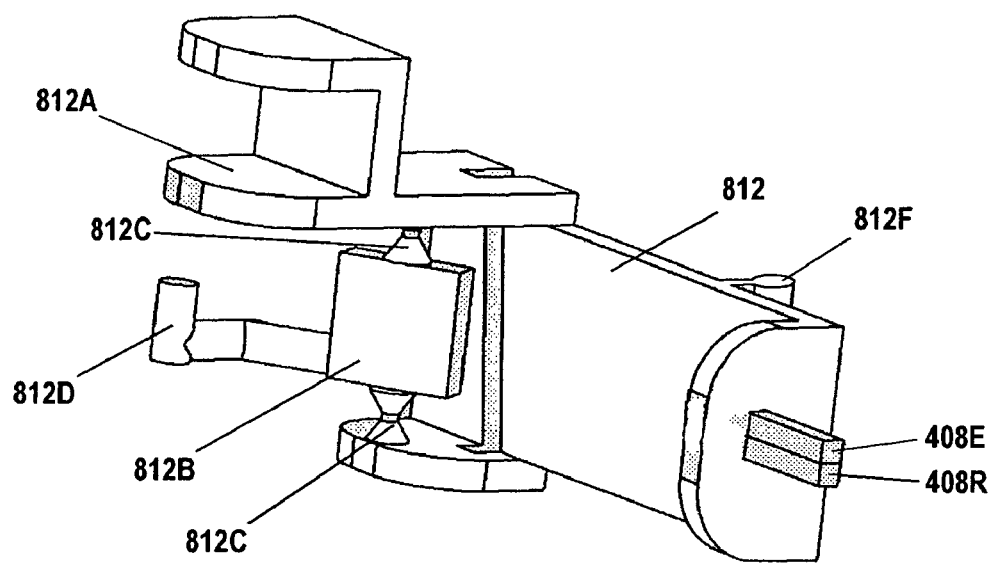
FIG. 12A is a perspective view of a fiber-optic scanner that may be used within a medicament dispensing tray, in accordance with one embodiment of the invention.

FIG. 12A is the perspective view of fiber-optic scanner 812 comprising a C-shaped element 812A that fits on the periphery of conical disk 902 such that the peripheral gear 902D (FIG. 9) freely rotates through the C-shaped element 812A but adjusts the height of the element 812A when the height of the conical disk 902 is adjusted. Thus, when conical disk 902 is moved up or down, scanner 812 follows conical disk 902 in the vertical direction. Hence the position of scanner 812 is maintained parallel to the periphery of the conical disk assembly. A pair of fiber optic cables 408E and 408R are attached to scanner 812. The other ends of fiber optic cables 408E and 408R emerge at port 408P, discussed above with reference to FIG. 3. The light emitting and receiving surfaces (not shown) at the end of fiber optic cable 408E and 408R, respectively, face a reflecting surface 812B. Reflecting surface 812B may be a high polish plastic or may include a thin coating of reflecting material. A beam of light is emitted through fiber optic cable 408E. This beam strikes on surface 812B. The reflected light from 812B is received by fiber optic cable 408R.

Reflecting surface 812B is suspended on scanner 812 by a two-point support. A spring mechanism 812C is present at the lower and upper points of the support and holds reflecting surface 812B at a particular angle. When reflecting surface 812B is rotated from its position, spring mechanism 812C restores reflecting surface 812B to its original position. An arm 812D is attached to reflecting surface 812B such that when conical disk assembly 802 rotates to dispense medicament unit 804, latch 814 interacts with arm 812D to rotate reflecting surface 812B. Once reflecting surface 812B is rotated, spring mechanism 812C restores reflecting surface 812B back to its original position. Hence every time medicament unit 804 is dispensed, reflecting surface 812B sweeps a certain angle. This angle provides a wide field of view to fiber optic cable 408R and as the reflecting surface sweeps through the angle it provides a view of the entire groove 808 and the medicament units 804 present therein to fiber optic cable 408R. In this way, the color, shape and/or size of medicament units 804 present in groove 808 can be identified by a sensor present in medicaments dispensing machine 106 that is connected to port 408P. In a further embodiment, explained in greater detail below with reference to FIG. 15, an additional scanner can be positioned above a top surface of the conical disk 802 to scan a surface of a medicament unit 804 stored in radial groove 808. By providing this additional scanning perspective and associated scan data, the method and system of the present invention provides more accurate identification of incorrect, counterfeit or tampered-with medicament units.

In one embodiment, appropriate processing circuitry and memory for storing comparative data and software reside within the dispensing machine 106 for processing the optical data provided by fiber optic cable 408R, and comparing the data to known optic parameters in order to make a decision as to the authenticity of the medicament units being dispensed. Such optical scanning and processing technologies are well known in the art. Furthermore, it is also understood by those of ordinary skill in the art, that other types of machine readable devices and their corresponding reader may be utilized instead of the fiber optic cables and scanners described above. For example, electromagnetic reading devices such as a charge-coupled device (CCD), or a CMOS optical array reading device, or an array of photo-diodes, or a Hall-effect device or other magnetic flux reading device may be utilized in the present invention.

Figure 12B:
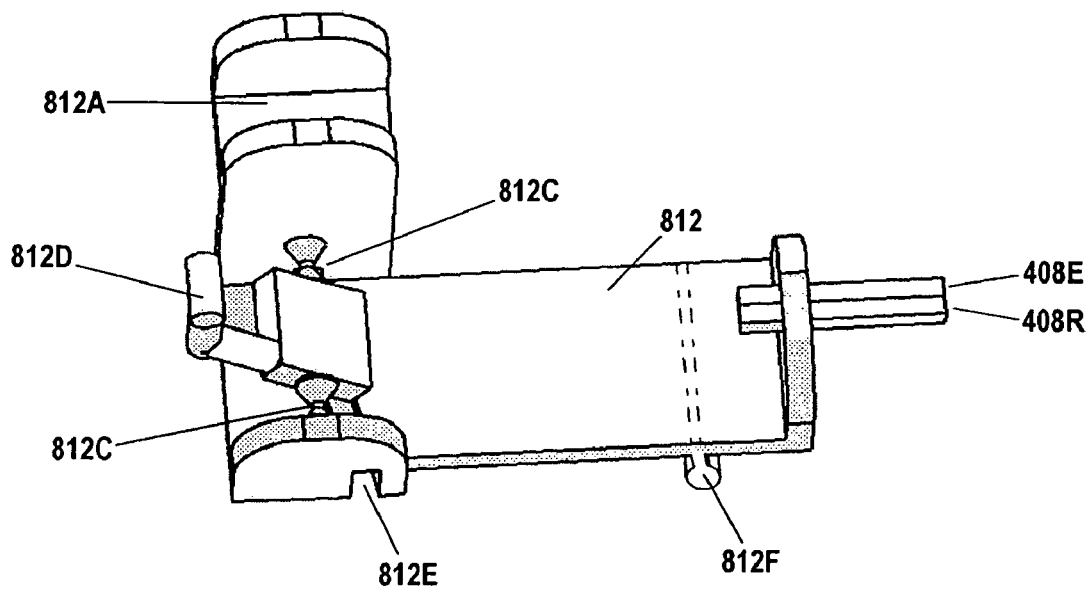
FIG. 12B is a bottom view of the fiber-optic scanner illustrated in FIG. 12A.

FIG. 12B provides another perspective view of the fiber-optic scanner 812 and further shows a groove 812E present on scanner 812. Groove 812E engages on an internal wall present in casing 202 in order to retain and secure scanner 812 in place. Another groove 812F is present on the back side of scanner 812 that engages another portion of an internal wall inside casing 202 so as to provide further support and stability to the scanner 812 inside the tray 100. It is appreciated that when the height of the scanner 812 is adjusted in accordance with the height of the conical disk 902, as described above, the grooves 812E and 812F allow movement in the vertical (or height) direction but securely holds the scanner 812 in place in the horizontal or lateral direction.

Figure 13A:
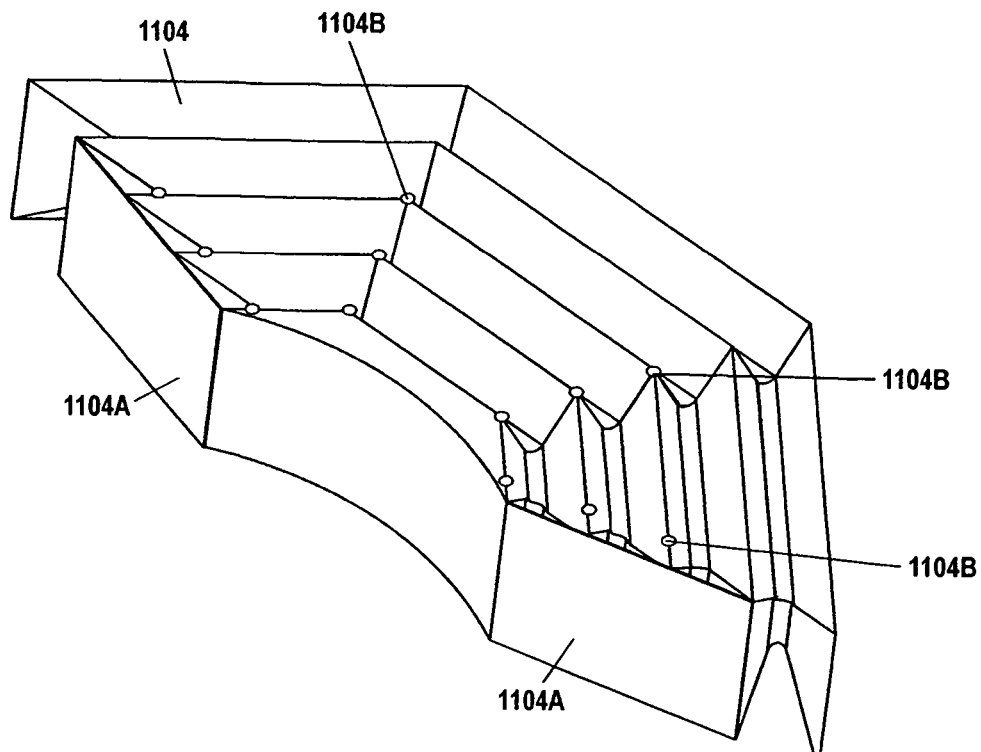
FIG. 13A is a top view of a pneumatic compressive bellow that may be used in a medicament dispensing tray, in accordance with one embodiment of the invention.

FIG. 13A illustrates a top view of a pneumatic compressive bellow 1104. In one embodiment of the invention, compressive bellow 1104 is an air bellow that is used for pushing medicament units 804 towards sorting and dispensing mechanism 800 (FIGS. 8 and 9). The bellow 1104 comprises a front wall 1104A that covers the complete cross-section of the medicaments storage section of tray 100. A wall 1104A ensures that no medicament unit 804 goes under or above compressive bellow 1104. Compressive bellow 1104 also comprises a series of buttons 1104B, formed in shape of small spheres, which move linearly in embossments 222 as compressive bellow 1104 inflates or deflates. Embossments 222 provide guiding rails to buttons 1104B so that bellow 1104 is held in a correct position and alignment.

Figure 13B:
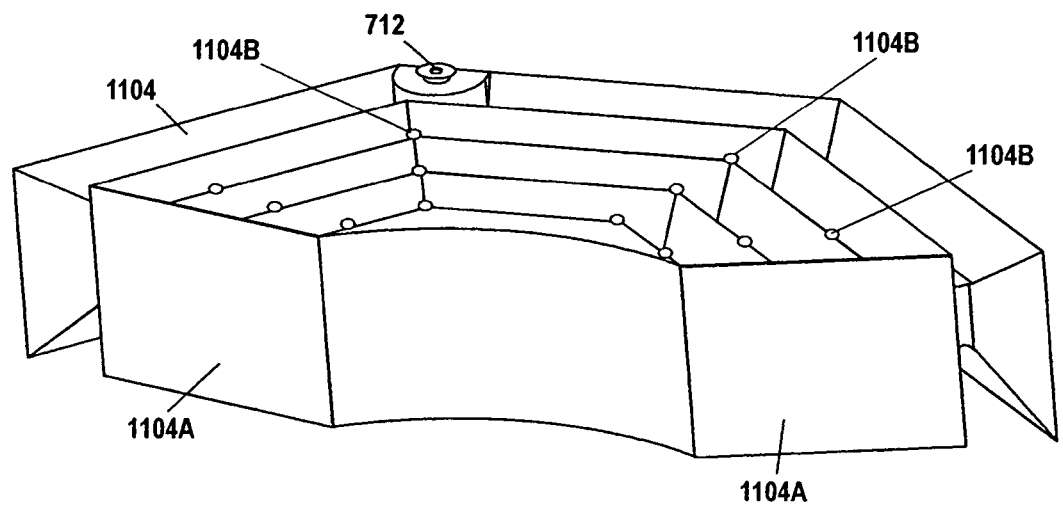
FIG. 13B is a bottom view of the pneumatic compressive bellow illustrated in FIG. 13A.

FIG. 13B illustrates a bottom view of the pneumatic compressive bellow 1104 and further shows a one-way valve 712 present on the bottom surface of compressive bellow 1104. Valve 712 provides an inlet for air into the bellow 1104. An opening to valve 712 is present on the lower surface of casing 202 (shown in FIG. 7). In a fully inflated state, compressive bellow 1104 occupies the entire area of the storage compartment and thus allows complete dispensing of all medicament units 804 within the storage compartment.

FIGS. 14A and 14B are cross-sectional views of two embodiments of gear-toothed surfaces on 902A, present on the bottom surface conical disk 902, and gear-toothed surface 904B, present on the top surface of conical disk 904 (shown in FIG. 8). The gear-toothed surfaces 902A and 904B engage each other to facilitate combined movement of conical disk 902 and conical disk 904.

FIG. 14A shows a ratchet arrangement for engagement of gear-toothed surface 902A with gear-toothed surface 904B that is used in one embodiment of the invention. This ratchet arrangement locks conical disk 902 and conical disk 904 such that they rotate together when rotated in a direction for dispensing medicament units 804, while allowing conical disk 902 and conical disk 904 to be rotated against each other in the other direction. In this way, as discussed above, the width of grooves 808 can be adjusted by rotating conical disk 902 and conical disk 904 against each other.

FIG. 14B shows another embodiment of the engagement mechanism between gear-toothed surface 902A and gear-toothed surface 904B. In this embodiment, gear-teeth of gear-toothed surface 902A and gear-toothed surface 904B are modified such that they engage into each other and lock conical disk 902 and conical disk 904 from rotating against each other in either direction.

FIG. 15 is a perspective view of fiber optic cables 406, 408, 410 and 412 discussed above. A pair of fiber optic cables 406E and 406R is connected to port 406P on one end. The other end of fiber optic cables 406E and 406R face conical disk assembly 802 and acquires a top surface view of conical disk assembly 802. Fiber optic cable 406E is used to emit light on conical disk assembly 802 and fiber optic cable 406R is used to receive reflected light from conical disk assembly 802. Fiber optic cables 406E and 406R communicate information regarding the positioning of conical disk assembly 802. In one embodiment of the invention, conical disk assembly 802 carries markings on the top surface of conical disk assembly 802 (discussed in further detail below with reference to FIG. 16) which are identified by a sensor connected to port 406P. Sensors for receiving optical data from a fiber optic cable are well known. For example, Tri-Color sensors manufactured by MAZeT GmbH, Germany, may be utilized. Additionally, light emitting devices for providing light to fiber optic emitter cables having molded or shaped optic lens at the end of each fiber optic cable are also well known. For example, Sony's RGB 3 Chip LED, model no. GM1WA55360A, may be utilized in accordance with the present invention.

In a further embodiment, the fiber optic cables 406E and 406R can also be used to scan medicament units 804 positioned within radial grooves 808 to assist in identifying color, shape and/or size of the medicament units stored therein. The cables 406E and 406R can alternatively or additionally be used to read one or more bar codes and/or markings present on each medicament unit 804. In this way, the method and system of the present invention further provides accurate detection of incorrect or counterfeit medicaments or detects when medicament units have been tampered with.

Fiber optic cables 408E and 408R connect port 408P to scanner 812 and communicate information such as bar code information and/or the color, shape and/or size of medicament units 804 being carried in grooves 808 of conical disk assembly 802.

Fiber optic cables 410E and 410R connect port 410P to a scanner 1501 present at outlet 210. Scanner 1501 comprises two reflector elements, 1502 and 1504. Fiber optic cable 410E emits light that is reflected by a curved and/or multi-faceted reflective surface 1506. In one embodiment, multiple facets (not shown) can be arranged along a curve or arc (as indicated by surface 1506) or, alternatively, along a straight line. The multiple facets divide an incident light beam into multiple reflected beams each traveling a different path toward a series of angular reflective surfaces 1506B. The beams reflect off the multiple angular reflective surfaces 1506B and become incident on a series of corresponding angular reflective surfaces 1508B on reflective element 1504. The beams are then reflected off of the angular reflective surfaces 1508B and become incident on curved and/or multi-faceted reflective surface 1508. In one embodiment, each facet of reflective surface 1506 has a different height to produce different light intensities or distributions. Alternatively or additionally, each of these facets could have a different reflective finish to produce different intensities. In contrast, in one embodiment, each facet of reflective surface 1508 is designed to maintain, as close as possible, the original beam intensities of the incident beams.

In another embodiment, reflective surface 1506 includes a holographic reflective surface with one or more facets for producing different intensities and guiding each light beam to a proper location. This scattered light is again reflected by the series of reflector surfaces 1506B present on reflector element 1502 towards a series of reflector surfaces 1508B present on reflector element 1504. The holographic reflective surface 1506 scatters the light to bands of different intensities. For example, a band of light 1510 that is reflected towards the bottom most reflector surface 1506B on reflector element 1502 has maximum intensity. On the other hand, a band of light 1512 reflected towards the top most reflector surface 1506B present on reflector element 1502 has minimum intensity. As indicated in FIG. 15, the band of light 1510, which has maximum intensity is shown by a darker, wider dashed line. The band of light 1512, which has minimum intensity is shown by a lighter, thinner dashed line. The bands of light reflected towards the series of reflectors 1508B present on reflector element 1504 are again reflected by the series of reflectors 1508B toward a holographic reflective surface 1508. In one embodiment, the holographic reflective surface 1508 is the mirror image of the holographic reflective surface 1506 and converges the different bands of light and reflects it towards fiber optic cable 410R. In contrast to the holographic reflective surface 1506, however, the surface 1508 is not designed to change the intensity of the incident light beams. In other words, the reflected beams are of the same, or nearly the same, intensity as the incident beams on the holographic reflective surface 1508. Holographic reflective surfaces are well-known in the art. In one embodiment, the holographic reflective surfaces can be an integral component of the respective reflector elements 1502 and 1504, e.g., via plastic injection molding and/or laser etching, so as to form the reflective surfaces 1506 and 1508. In other embodiments, the holographic reflective surfaces can be attached, e.g. via glue or snapped on, to the surfaces 1506 and 1508. Alternatively, the holographic reflective surfaces can be sandwiched between a bottom surface of the tray casing 204 (FIG. 2) and respective underside surfaces of the elements 1506 and 1508, or other desired location on reflective 1502 and 1504.

When medicament unit 804 is being dispensed out of outlet 210, it cuts across the bands of light that travel from the series of reflective surfaces 1506B to the series of reflective surfaces 1508B. According to the size of the medicament unit, different number of bands would be cut across by medicament unit 804 and therefore the intensity of light received by fiber optic cable 410R would depend on the size of medicament unit 804.

A sensor in the medicaments dispensing machine 106, connected to port 410P and coupled to the scanner 1501, detects medication properties and sends to the proper smart tray 100 the information for the smart tray circuitry to count and update the number of medicament units being dispensed and/or that have been dispensed. This data also allows the smart tray 100 to calculate and compare the size of medicament unit 804 being dispensed with data stored in its memory to further verify the authenticity of the medicament units being dispensed. Additionally, in further embodiments, the sensor is capable of determining if there are any problems with the dispensing of medicaments. For example, if more than one medicament unit is being dispensed each time or there is a jam at the dispensing outlet of the dispensing tray, the sensor, via scanner 1501, can detect these conditions.

Fiber optic cable 412 connects port 412P to display 244. In one embodiment, all display information, including colors and digits displayed by display 244, are sent by the medicaments dispensing machine 106 through port 412P and fiber optic cable 412.

FIG. 16 is an illustration of a main conical disk encoder layout, in accordance with one embodiment of the invention. Conical disk assembly 802 carries a marking pattern 1602 on the top surface of conical disk assembly 802. Marking pattern 1602 may be imprinted, put on a label or may be made by injecting a colored substance into the conical disk assembly 802 material. In one embodiment, markings 1602 are preset in each section between grooves 808. Cables 406E and 406R are placed such that the end surfaces of cables 406E and 406R, away from port 406P, face marking pattern 1602. Marking pattern 1602 comprises a marking 1602A at one end of the marking pattern 1602 and marking 1602B on the other end. For example, when the sensor connected to port 406P reads marking 1602A, the sensor identifies that the position of conical disk assembly is just after dispensing of medicament unit 804. When the sensor connected to port 406P reads marking 1602B, the sensor identifies that the position of conical disk assembly is just before dispensing of a medicament unit 804. Furthermore, marking pattern 1602 comprises several markings 1602C. In one embodiment of the invention, markings 1602C are uniformly distributed such that when conical disk assembly 802 is rotating, the sensor connected to port 406P identifies the speed at which conical disk assembly is rotating. Marking pattern 1602 therefore allows the medicament dispensing machine 106 to determine the motion and position of conical disk assembly 802, which further assists in determining any error or malfunctions during operation of tray 100.

Figure 17A:
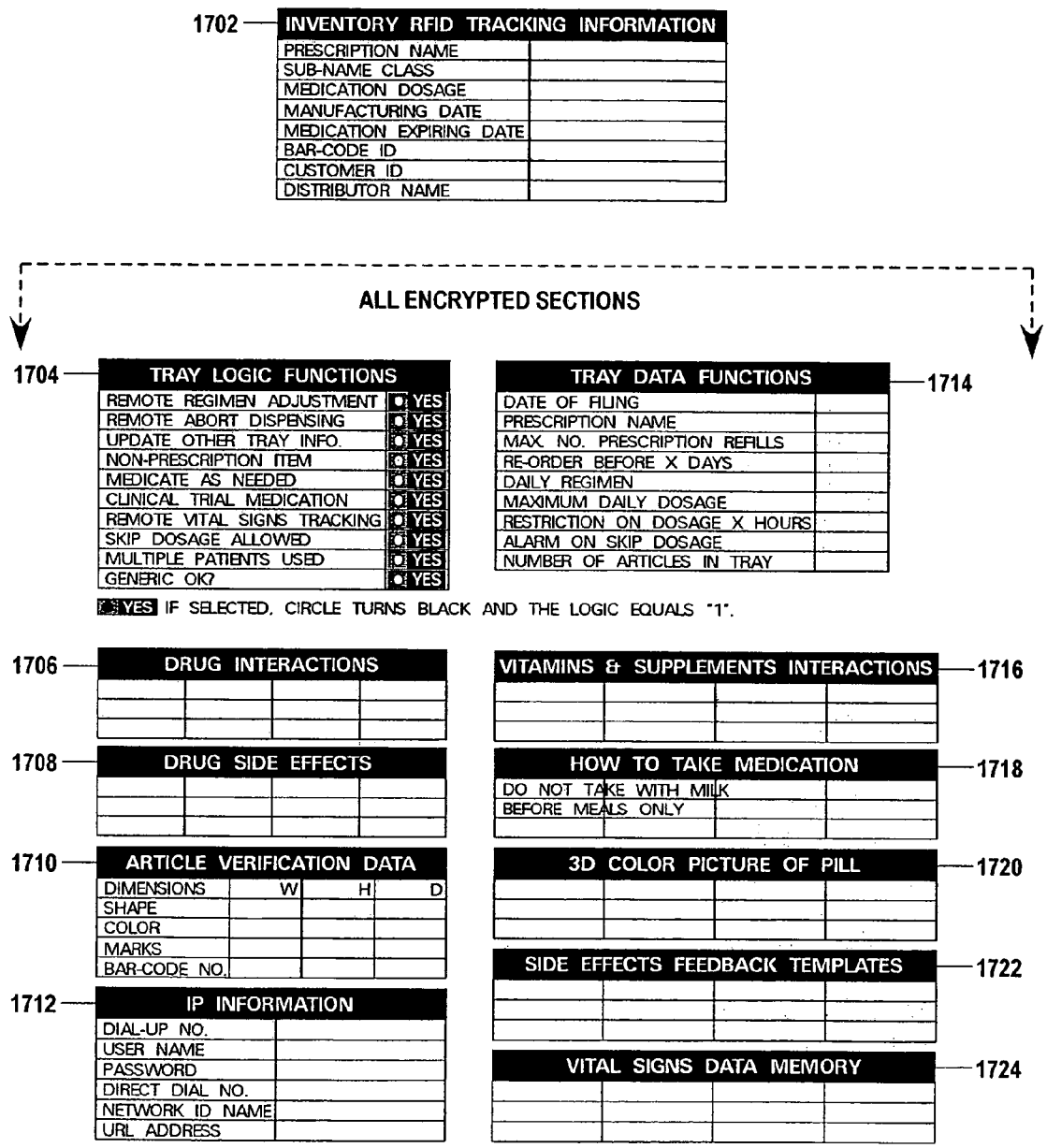
Figure 17E:
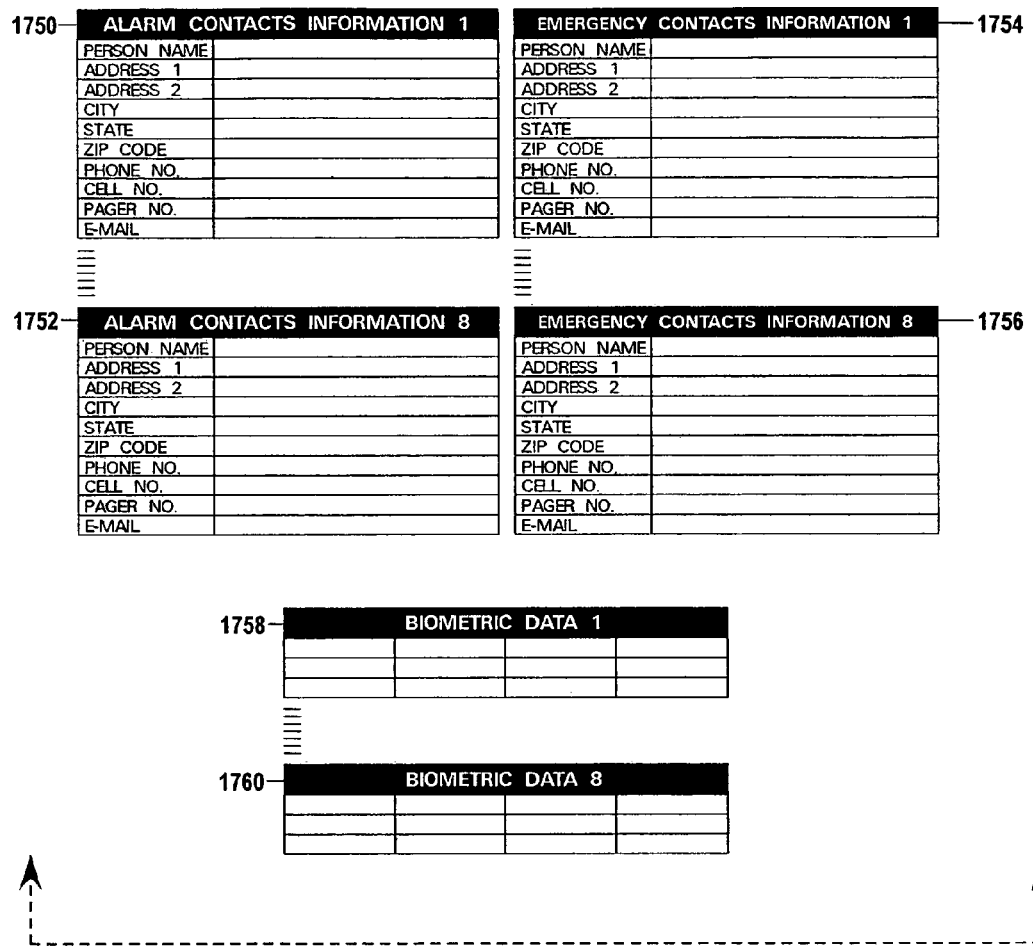

FIGS. 17A, 17B, 17C and 17D provide exemplary layouts of various patient memory tables and microinstructions in accordance with one or more embodiments of the invention. FIG. 17A shows exemplary data that may be stored in the wireless communication device 1102 and/or other memory present in a dispensing tray 100 for use by a patient. Table 1702 includes exemplary information typically provided in a non-encrypted format. This information includes inventory and tracking information for the use of a pharmacy or may be used for transportation of tray 100. This information is available even when tray 100 is in a non-dispensing mode and provides automated shipping logistics for tray 100. This information also allows for automated tracking of tray 100 when tray 100 is at a filling stage at a pharmacy or being shipped. Thus, in one embodiment, this information permits synchronization of commerce between distributors, merchants, shipping logistic companies and end users. For example, after an end user receives a smart tray 100 and inserts it into a dispensing machine 106, the inventory and tracking information will be sent via an electronic communication network, coupled to the dispensing machine, to a pharmacy, manufacturer and/or caregiver. In this way, all parties concerned can verify safe arrival of the smart tray 100 to its intended destination and compliance with prescription refill protocols, etc.

Table 1704 represents exemplary data regarding tray logic functions that may be present in the electromagnetic communication device 1102 and/or other memory. Data regarding tray logic functions include information such as intended use of medicament units present in tray 100, the identity of authorized personnel that may dispense the medicaments in the tray, etc. Table 1706 illustrates drug interactions information. Table 1708 illustrates information regarding the side effects of the drug contained in tray 100. Table 1710 illustrates verification data for medicament units stored in tray 100 such as dimensions, color, shape, size and other identification marks present on medicament units 804. This information is used for identifying authenticity of medicament units 804 as discussed above. Table 1712 illustrates internet protocol (IP) information required for allowing tray 100 to communicate via the Internet with other network devices. Table 1714 illustrates tray data functions such as date on which tray 100 was filled, prescription name, dosage, and other information. Table 1716 illustrates information regarding vitamins and supplement interactions of the drug present in tray 100. Table 1718 illustrates additional information regarding intake of the drug present in tray 100. For example, this information may include instructions such as the drug present in tray 100 should not be taken with milk. Table 1720 illustrates that the electromagnetic communication device 1102, for example, stores a three-dimensional (3-D), color picture of medicament unit 804. This allows a more comprehensive analysis of the entire pill and its dimensions and other characteristics. Table 1722 illustrates information regarding side-effect feedback templates. A medical practitioner can update this information. Table 1724 illustrates information regarding the expected vital signs of a patent when the drug or medicaments in tray 100 are used. Via password protection and/or other security techniques, the information illustrated in tables 1704, 1706, 1708, 1710, 1712, 1714, 1716, 1718, 1720, 1722, and 1724 can be updated or changed by an authorized pharmacist or medical practitioner and cannot be changed by a user.

FIGS. 17B, 17C and 17D illustrate exemplary data pertaining to the users of tray 100 that is present in wireless communication device 1102 and/or other memory residing within the tray 100. In one embodiment, nonvolatile memory within wireless communication device 1102 may store information for multiple users. For example, a tray may be used by a patient A and a patient B. Table 1726 illustrates personal information for patient A. Table 1728 illustrates information regarding allergies for patient A. Table 1730 illustrates information regarding the medical condition of patient A. Table 1732 illustrates personal information for the authorized medical practitioner who prescribes the medication or treatment to the patient. The medical practitioner is hereinafter referred to as the prescriber.

Table 1734 illustrates prescription insurance information for patient A. This information can be directly communicated to the insurance agency and required insurance claims may be made automatically. Tables 1736, 1738, 1740, 1742, and 1744 in FIG. 19C and FIG. 17D illustrate similar information for patient B as the information illustrated by tables 1736, 1728, 1730, 1732, and 1734 for patient A. Though only two exemplary users for tray 100 have been illustrated, several users may use tray 100 and wireless communication device 1102 may contain information for several users. Table 1746 illustrates the drug store or pharmacy information. Table 1748 illustrates payment information such as credit card information and address for delivery etc. Table 1750 and 1752 illustrate contact information in case a patient misses a dosage of medication, in case of adverse side effects of a medicine or in case the patient needs help. This contact information is used in case of a non-emergency situation. This may include contact information for hospitals, ambulance agencies, relatives, friends etc. Though only two tables for alarm contact information have been provided in FIG. 17E, wireless communication device 1102 may store contact information for any number of people provided that enough memory resides within wireless communication device 1102.

Tables 1754 and 1756 illustrate emergency contact information. This information includes contact details for the prescriber, hospitals, ambulance agencies etc., which are required to be contacted in case of an emergency. Though only two tables for alarm contact information have been provided in FIG. 17E, wireless communication device 1102 may store contact information for several people. Tables 1758 and 1760 illustrate biometric information for the users of tray 100. Biometric information may include thumbprints, voice recognition information and retina identification information. This information is used to identify the rightful user of tray 100. The medicaments dispensing machine 106 may check for one or more of these biometric information to identify the user before dispensing a medicament unit. Wireless communication device 1102 may include biometric information for multiple users.

In one embodiment, the information illustrated in tables 1704, 1706, 1708, 1710, 1712, 1714, 1716, 1718, 1720, 1722, 1724, 1726, 1728, 1730, 1732, 1734, 1736, 1738, 1740, 1742, 1744, 1746, 1748, 1750, 1752, 1754, 1756, 1758, and 1760 is in an encrypted format. This information is available only when tray 100 is in a dispensing mode, i.e., when tray 100 is inserted in the medicaments dispensing machine. Further, this information is revealed only when the authenticity of a user has been verified.

The information illustrated in tables 1726, 1728, 1730, 1732, 1734, 1736, 1738, 1740, 1742, 1744, 1746, 1748, 1750, 1752, 1754, 1756, 1758, and 1760 may be changes or updated by a patient or a care giver. The patient or the caregiver may change this information through phone, Internet browser, fax, email, pager or other means.

Figure 18A:
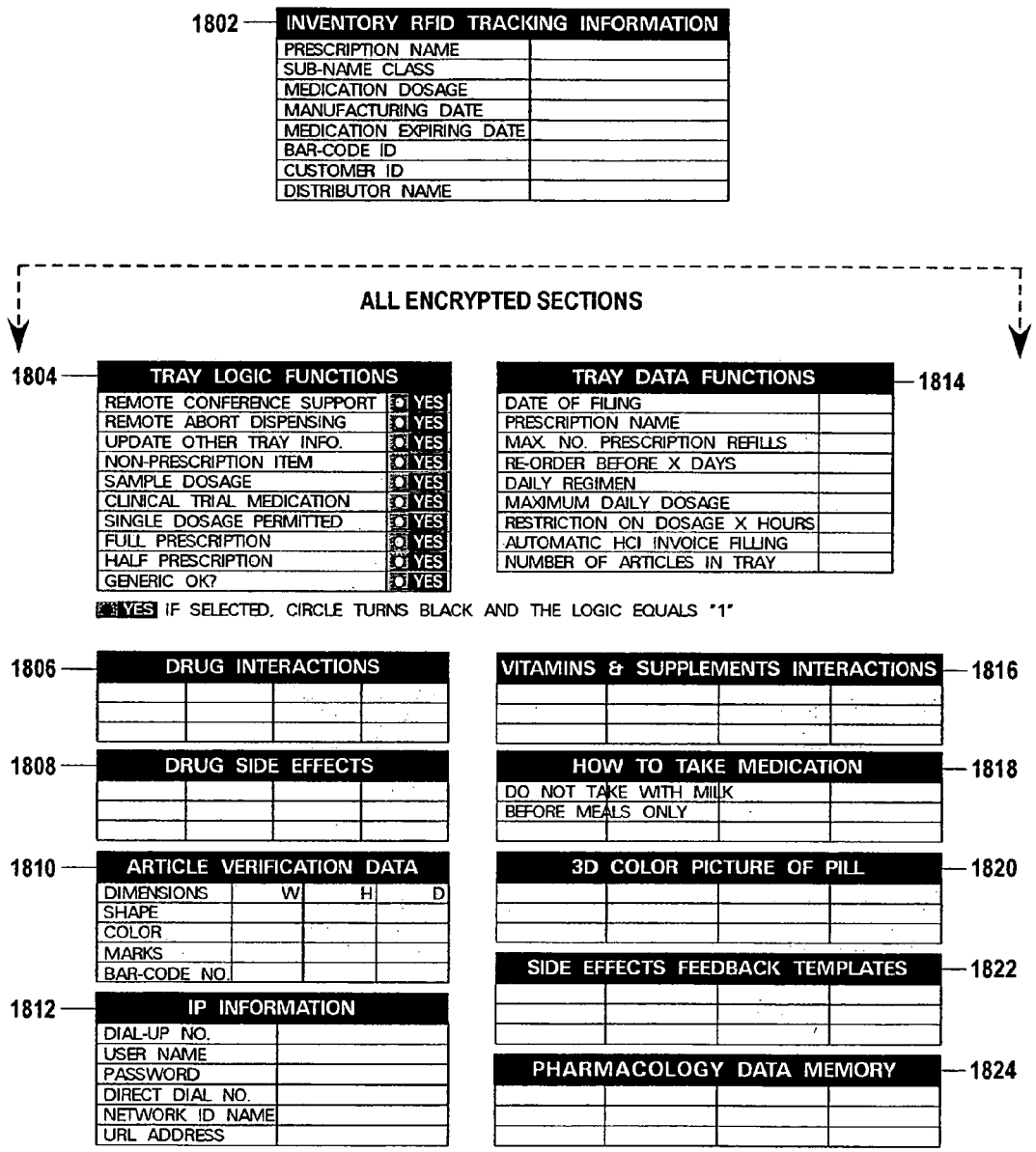
Figure 18C:
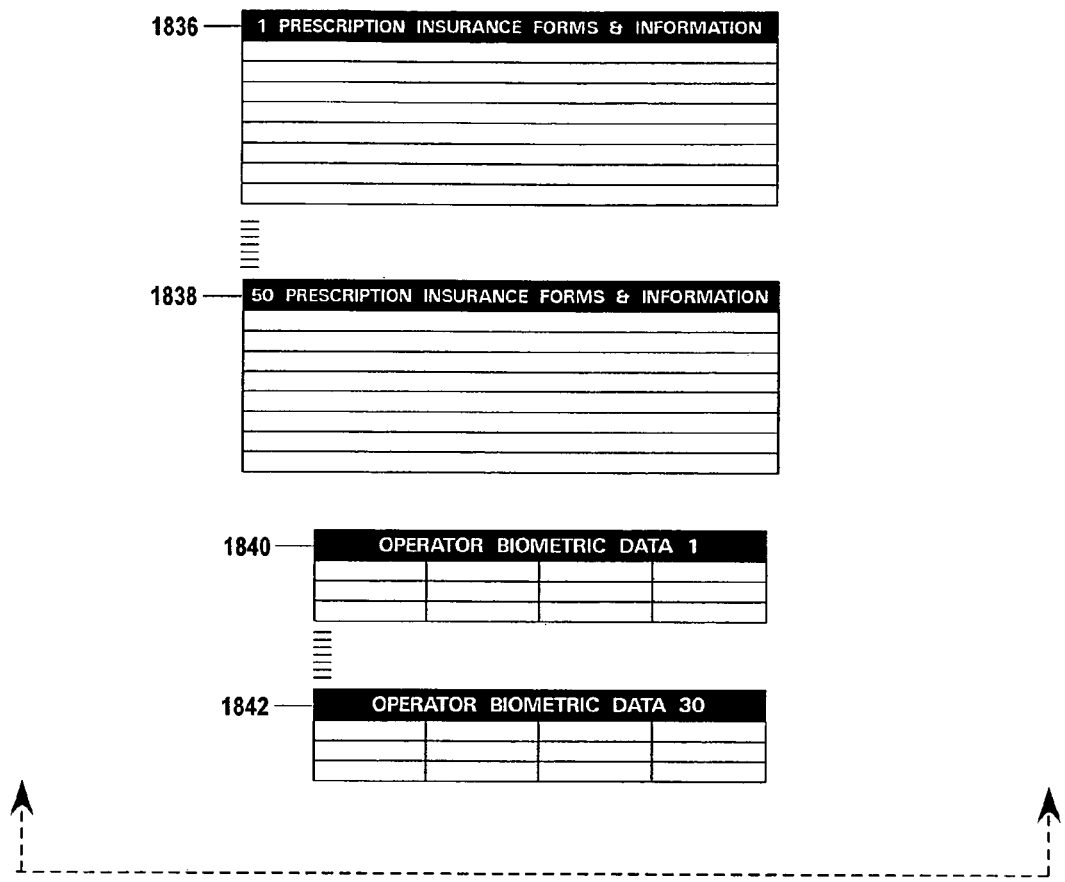

FIGS. 18A, 18B, and 18C illustrate exemplary layouts of a healthcare professional memory table. FIG. 18A shows exemplary data that may be stored in a wireless communication device 1102 and/or other memory present in a dispensing tray that is used for professional healthcare by a caregiver. Tray 100 may be used for professional healthcare in places like hospitals, clinics, a nursing home, a medical practitioner's office, or a pharmacy. Table 1802 includes information present in a non-encrypted format. This information includes inventory and tracking information for use by a pharmacy or during transportation of tray 100. This information is available even when tray 100 is in a non-dispensing mode. This information provides automated shipping logistics for tray 100 and also provides an automated tracking system for tray 100 when tray 100 is at filling stage, at a pharmacy or being shipped.

Table 1804 represents exemplary data regarding tray login functions that may be present in wireless communication device 1102. Data regarding tray logic functions include information such as intended use of medicament units present in tray 100. Table 1806 illustrates drug interactions information. Table 1808 illustrates information regarding the side effects of the drug contained in tray 100. Table 1810 illustrates verification data for medicament units stored in tray 100 such as dimensions, color, shape, size and other identification marks present on medicament units 804. This information is used for identifying authenticity of medicament units 804. Table 1812 illustrates Internet protocol (IP) information required for tray 100 to communication via the Internet with other network devices. Table 1814 illustrates tray data functions. Tray data functions include information such as date on which tray 100 was filled, prescription name, dosage, and other information. Table 1816 illustrates information regarding vitamins and supplement interactions of the drug present in tray 100. Table 1818 illustrates additional information regarding intake of the drug present in tray 100. For example, this information may include instructions such as the drug present in tray 100 should not be taken with milk. Table 1820 illustrates that wireless communication device 1102 stores a 3-dimensional, color picture of medicament unit 804. Table 1822 illustrates information regarding side-effect feedback templates. A medical practitioner can update this information. The medical practitioner can update this information using phone, Internet browser, fax, email, pager or other means. Table 1824 illustrates information regarding the pharmacology data for the drug or medicaments in tray 100.

In one embodiment, the information illustrated in tables 1804, 1806, 1808, 1810, 1812, 1814, 1816, 1818, 1820, 1822, and 1824 can be updated or changed by an authorized pharmacist or medical practitioner and cannot be changed by a user. Much of the information not pertaining to dosages and medication type prescribed can be updated automatically by the main server to insure security and safety to the end patient. For example, FDA recalls, side effect templates, instructions how to take a medication, health insurance policy changes, to name a few, can be automatically updated with the latest available information If, for example, an insurance company decides to no longer pay for a particular brand medication, the end user and/or the caregivers can be promptly notified.

FIGS. 18A and 18B illustrate exemplary data pertaining to the prescriber and the operators of tray 100 that is present in wireless communication device 1102. Table 1826 and 1828 illustrate the personal information of the prescribers for the medicaments in tray 100. Though information for only two prescribers has been illustrated in FIG. 18B, wireless communication device 1102 may store personal information for a multiple prescribers, depending on its memory capacity and/or the capacity of other memory residing inside the tray 100. As discussed above, any suitable form of programmable memory or data storage device may be used in the present invention. Table 1830 illustrates information regarding acceptance of payment for the medicaments. For example, this information includes mode of payment such as credit card, check or cash. Table 1832 illustrates information regarding approval of the prescription by insurance company. Table 1834 illustrates contact information for the drug store or pharmacy that has provided tray 100. Tables 1836 and 1838 illustrate the information regarding the insurance for the medication, including the prescription insurance form. Though only two tables representing prescription insurance forms and information have been provided, wireless communication device 1102 may include information for multiple prescription insurance forms and information. Tables 1840 and 1842 illustrate biometric information for the operators of tray 100. Biometric information may include thumbprints, voice recognition information and retina identification information. This information is used to identify the rightful user of tray 100. The medicaments dispensing machine may check for one or more of these biometric information to identify the user before dispensing a medicament unit. Wireless communication device 1102 may include multiple biometric information for multiple users.

At each stage of transit and operation of each tray 100, wireless communication device readers (e.g., those comparable to RFID tag and/or "smart card" readers) are provided at desired locations during transit, at pharmacies, at hospitals and within automatic medicament dispensing machines such that information stored within the memory of the wireless communication devices may be accessed, read and or changed for each tray. In this way, a secure, intelligent and automated process of tracking and dispensing medicaments is provided by the present invention. In one embodiment, the wireless communication device readers are communicatively coupled or networked to other readers and network devices (e.g., computers, servers, etc.) such that information pertaining to many trays at various locations may be tracked, accessed and stored at various locations where a communicatively coupled network device resides.

In a further embodiment, when a tray 100 is inserted into a medicament dispensing machine 106, all necessary information contained in the wireless communication device 1102 within the tray 100 is automatically shared by serial circuitry (not shown) within the dispensing machine 106. In other words, the circuitry within the dispensing machine 106 can access the memory within the smart tray 100, thereby increasing the amount of memory useable by the dispensing machine 106. Conversely, circuitry within the smart tray 100 can access one or memories within the dispensing machine 106 to process and/or store data contained therein. In alternative or additional embodiments, data may be downloaded or uploaded between the memories contained in the smart tray 106 and the dispensing machine 100 for processing and/or storage. The dispensing machine 106 thereafter uses this information to monitor and control access to medicaments stored within that tray 100. In this fashion, a sort of "plug and play" functionality is provided for medicament dispensing trays 100, which requires a minimum amount of manual operations by a human.

Figure 19:
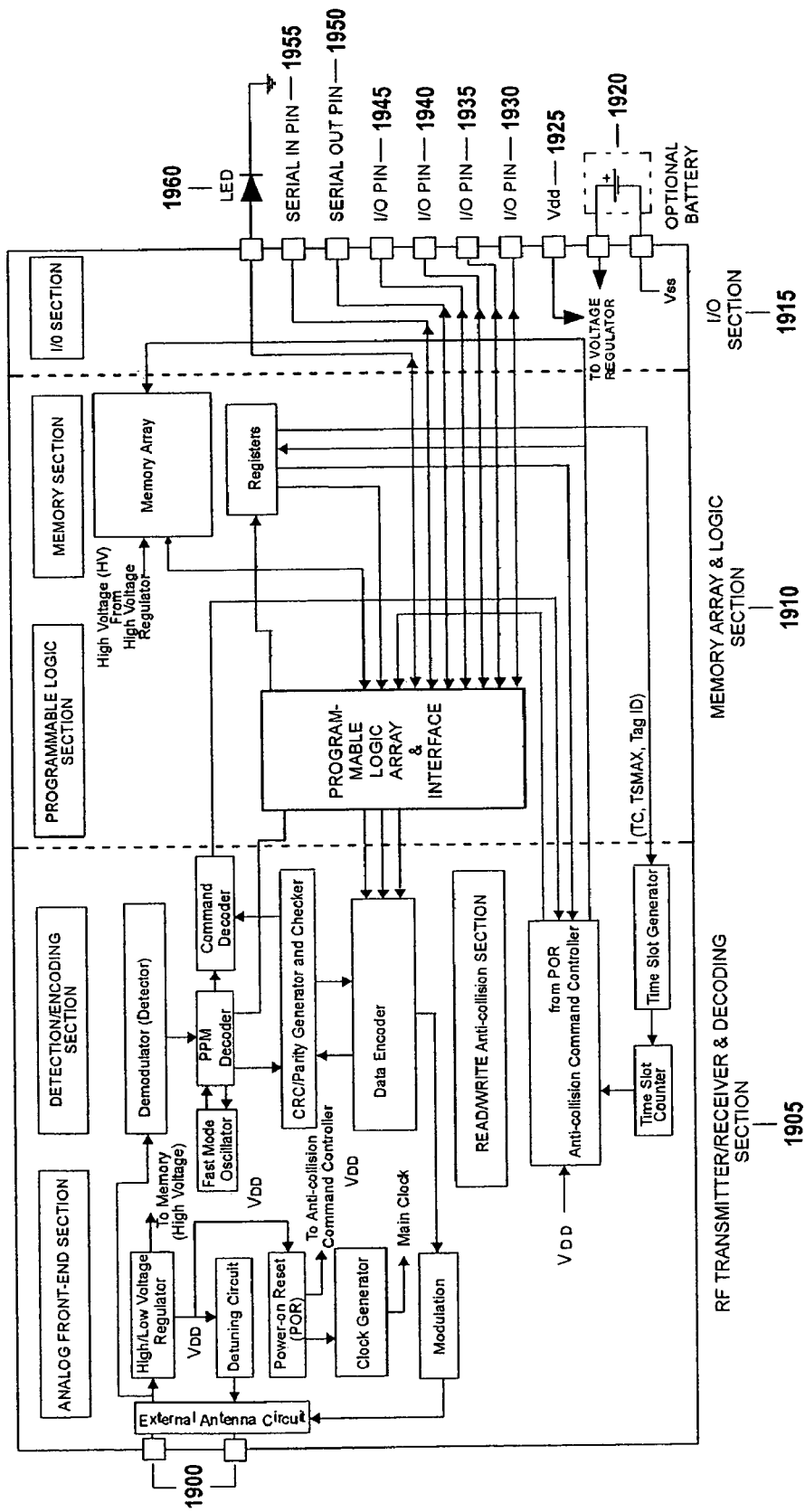
FIG. 19 is a block diagram of electronic components and/or circuitry residing within a smart tray, in accordance with one embodiment of the invention.

FIG. 19 is the block diagram of a custom integrated circuit (IC) including known RFID technologies and micro circuitry. The unit is comprised of four sections: 1900, 1905, 1910 and 1915. Section 1900 provides contacts to an external antenna (e.g., an inductor coil) which may be located on an external printed circuit board on which the custom IC is placed.

Section 1905 is the electromagnetic transmitter and receiver decoding section for transmitting, receiving, encoding and decoding data/information. In one embodiment, section 1905 operates in accordance with standard RFID tag communication protocols, which use a standard 13.68 megahertz frequency to transmit and receive data. As is known to those of ordinary skill in the art, current RFID communication protocols implement "anti-collision" routines and techniques which permit multiple RFID tags within a given proximity to operate simultaneously and communicate with external devices without interfering with each other. As is shown in section 1905, an Anti-Collision Command Controller is provided to provide anti-collision functionality to the smart tray. Because multiple smart trays can simultaneously (or near-simultaneously in an interleaving fashion) communicate with an external device (e.g., a RFID tag reader), inventory control and/or tracking of multiple smart trays during transit can be simplified. Section 1905 can comprise well known transceiver circuitry and/or components for transmitting and receiving data. In one embodiment, as shown in FIG. 19, section 1905 includes standard components such as a time-slot generator, time slot counter, a data encoder, a CRC/Parity Generator and Checker, a demodulator, a PPM Decoder, a Command Decoder, a Fast Mode Oscillator, a modulator, clock generator, power-on-reset circuit, a detuning circuit and a voltage regulator. All of these components are standard components that are well known in the art and, therefore, a discussion of their operation and functionality is omitted herein. It is understood, however, that the circuit architectures and components illustrated and described herein are exemplary only and that other circuit architectures, devices and components may be designed and implemented by those of ordinary skill in the art to perform the functions described herein, without undue experimentation.

Section 1910 comprises a memory array and logic section, which includes a reprogrammable electron valve array for storing data, programs and encryption data, status registers, and a programmable logic array and interface for executing desired logical functions or operations. Such devices and components are also well known in the art.

Section 1915 is the Input/Output section which provides an interface and contact terminals or pins for communicatively coupling a smart tray to a dispensing machine or other desired external device (e.g., an inventory tracking or medicament loading machine). The Input/Output section 1915 includes pins 1920 which provides contacts for an optional external battery (not shown). Standard RFID tags normally operate without any battery power but instead receive their power from an external electromagnetic field provided by an external reader device. This may pose a problem, however, if RFID tags are used in hospitals, military bases, etc., where other equipment that is sensitive to electromagnetic radiation may be located. In such environments, it may be desirable to limit the level of electromagnetic radiation. Therefore, having an optional battery power supply allows the operation of RFID tags or circuits in these locations without using electromagnetic fields to power the RFID tags/circuits.

A direct communication path can be established between a smart tray and a dispensing machine via serial input and output pins, 1955 and 1950, respectively. In one embodiment, the serial input and/or output pin 1955 and 1950, respectively, can provide power as well as data to the smart tray 100. Pins 1930, 1935, 1940 and 1945 are provided for future expansion or different functions of the smart tray circuitry. Pin 1960 provides an output contact directly to an LED which can be used to provide visual alerts to persons who are adding and removing trays so they have additional information rather than just a written label on the smart tray to make sure that they are dealing with the correct tray. For example, circuitry within the tray can send a signal to the LED so that it provides a red light, for example, if it is in inventory mode waiting to placed into a dispensing machine 106. In this way, a person retrieving a tray to be inserted into a dispensing machine is informed of which tray is the correct tray.

Figure 20A:
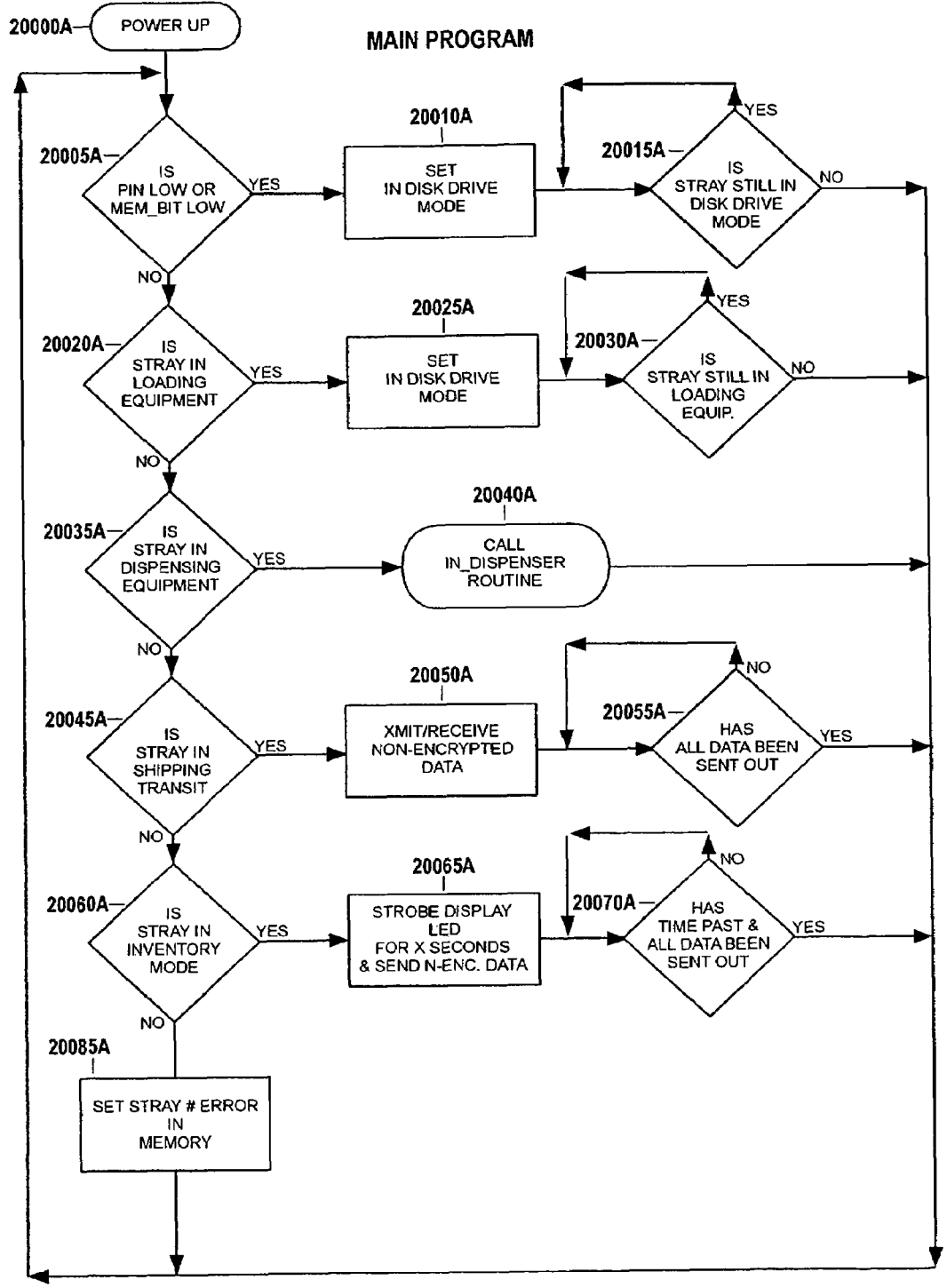
FIGS. 20A-20E illustrate flowchart diagrams of various logical functions performed by software, firmware and/or hardware residing within a smart tray, in accordance with various embodiments of the present invention.
Figure 20B:
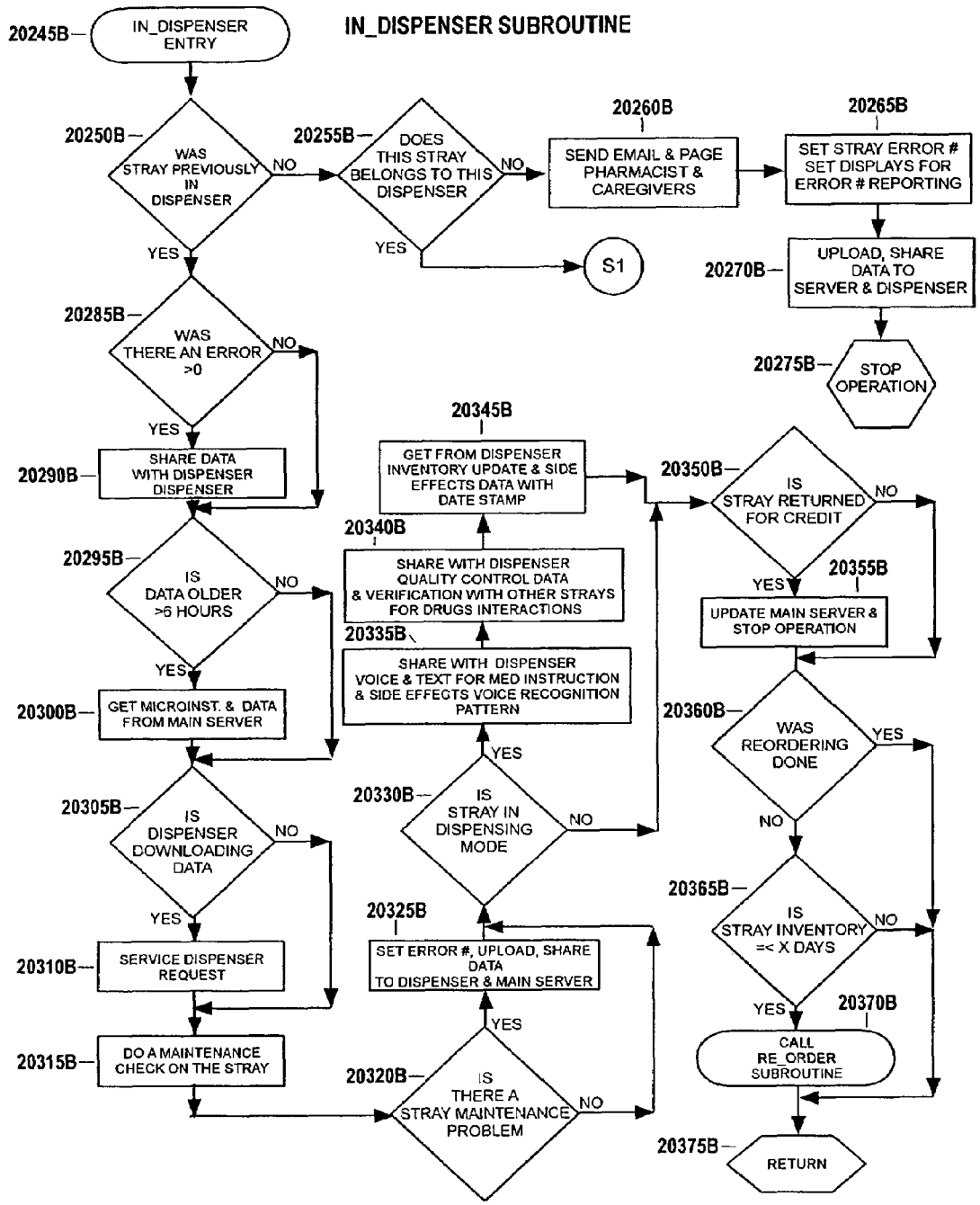
Figure 20C:
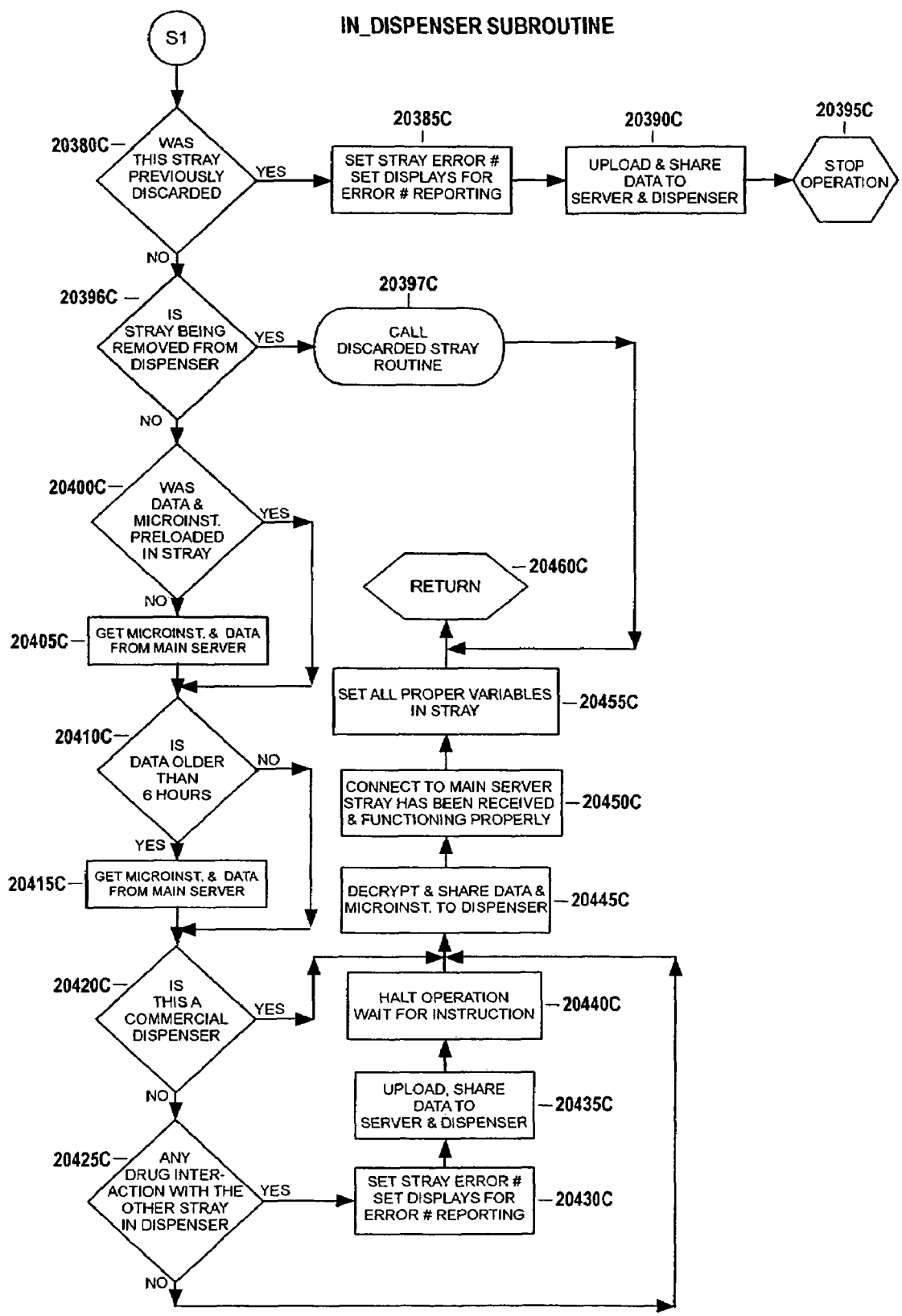
Figure 20D:
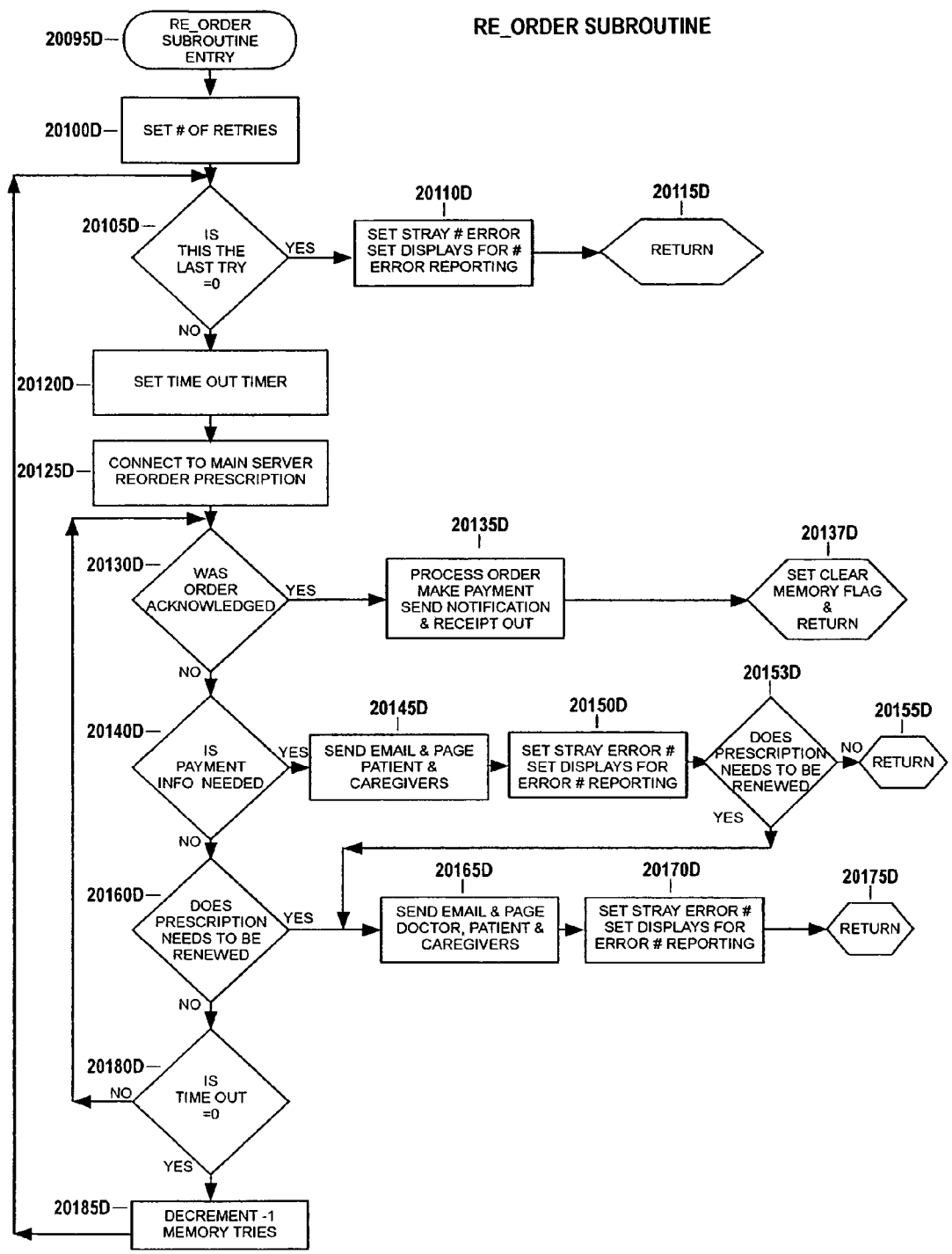
Figure 20E:
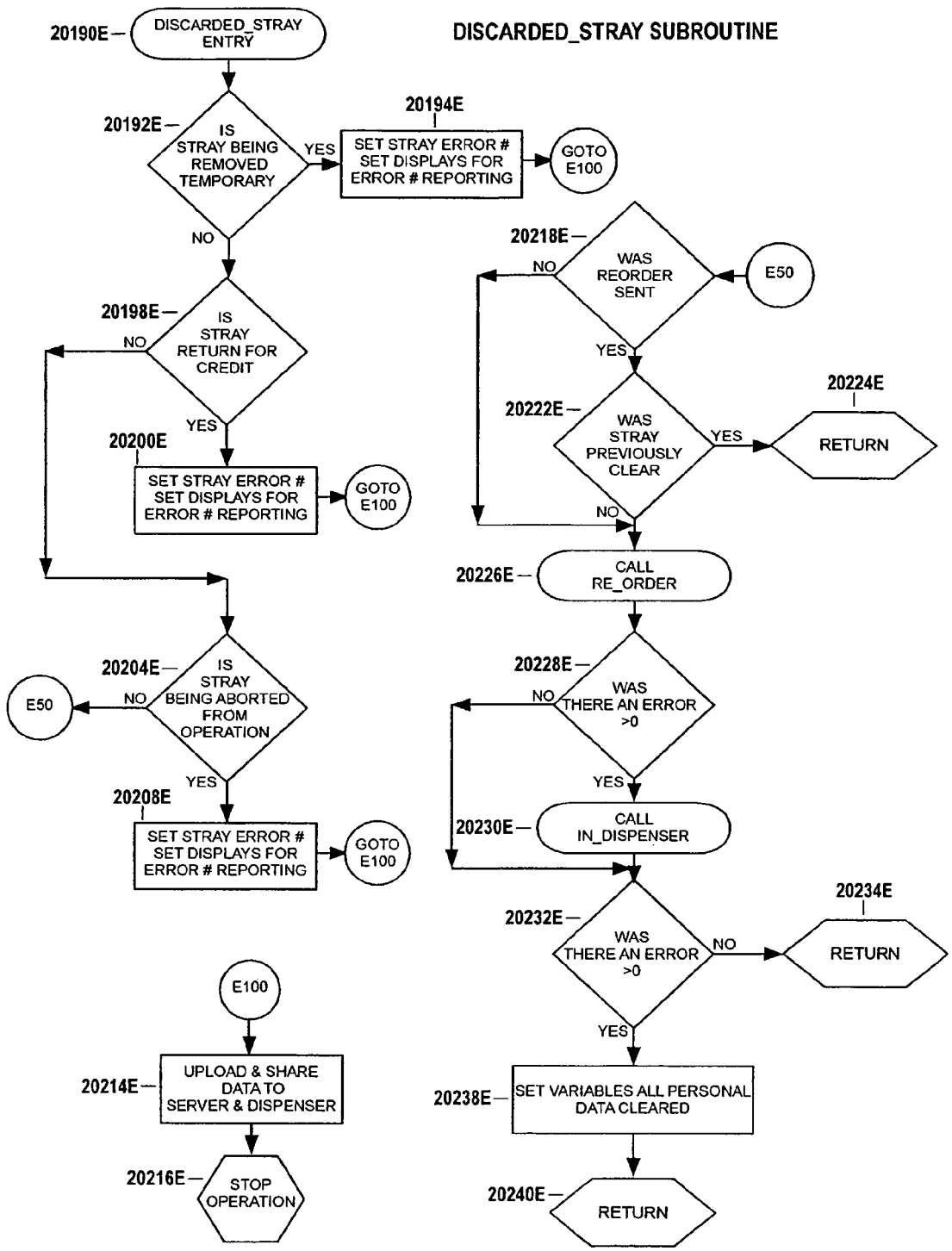

FIGS. 20A-20E illustrate flowcharts of various functions implemented by the programmable logic array of section 1910 (FIG. 19), in accordance with one or more embodiments of the invention. It is understood, however, that other known processing circuitry (e.g., a microprocessor, ASIC, etc.) may perform these functions via software and/or firmware residing within an internal memory of the smart tray. The flowcharts are divided into one main program or routine and four subroutines, in accordance with one embodiment of the invention. FIG. 20A (starting at 20000A) is the main program. FIGS. 20B and 20C (starting at 20245B) illustrate an In_Dispenser Subroutine when the smart tray is inserted into a dispensing machine. FIG. 20D (starting at 20095D) is a Re_Order Subroutine when a smart tray is empty or near-empty, or before it is discarded. FIG. 20E (starting at 20190E) is a Discarded_Stray Subroutine when a tray is either empty or removed from the dispensing equipment smart tray Referring to FIG. 20A, at step 20000A, electronic circuitry within the smart tray is powered up. In preferred embodiments, this occurs either: (a) when the Tray is placed into the dispenser and is activated by signals and/or power supplied by the dispenser, or (b) when the Tray is placed within proximity of an external device that provides an electromagnetic field to energize circuitry (e.g., RFID circuitry) within the Tray, or (c) by using a battery to power the internal circuitry of the tray.

The main program starts at step 20005A which first determines whether the tray is in "disk drive mode." In one embodiment, it makes this determination at step 20005A by checking whether a pin on the IC chip within the smart tray is set to low or a designated bit in a status register is set. If the designated pin or register bit is set, at step 20010A, the smart tray is placed in disk drive mode. The disk drive mode is the mode wherein the smart tray is ready to provide requested data stored in its memory array and store data received from an external device (e.g., a medicament loading machine) in its memory array. At step 20015A, the program periodically checks the status of the designated pin or bit and determines whether the tray should still be in disk drive mode. If the status of the pin or bit has changed, the process returns to step 20005A.

If at step 20005A, it is determined that the designated pin or register bit is not set to low (or alternatively to high), then at step 20020A, the smart tray determines whether it is in a loading mode. In one embodiment, this determination is made by checking whether the voltage on the designated pin is set to high or the designated bit in the status register is set to high. Alternatively, a different pin and/or register bit from that discussed above can be used to make this determination. If it is determined that the smart tray has been inserted into medicament loading equipment, the tray is then ready to receive medicaments from the loading equipment. While the tray is being filled with medicaments (e.g., pills), at step 20025A, the tray is set to disk drive mode so that the loading equipment can communicate with the tray. In one embodiment, the disk drive mode places the tray into a direct memory access (DMA) mode for faster reading and writing of information from and to memory within the tray. Various DMA schemes and protocols are known in the art. For example, information such as quantity and type of pill, designated patient information, transit information, may be communicated between the loading equipment and the tray. The loading equipment receives all necessary and/or desired information from memory within the tray. Conversely, the tray receives and stores all pertinent information from the loading equipment. Thus, by utilizing DMA protocols, the tray can facilitate high speed loading of medicaments into the smart tray 100 and reduce medicament filling time and costs. At step 20030A, the tray determines if it is still coupled to the loading equipment. If not, loading of medicaments has been completed and the process returns to step 20005A.

At step 20035A, the smart detects if it has been loaded into medicament dispensing equipment (e.g., a medicament dispensing machine 106 (FIG. 1A)). If the tray is in a dispensing machine, at step 20040A, the program calls an In_Dispenser Subroutine, described in further detail below with reference to FIG. 19D. After the In_Dispenser Subroutine has been completed, the main program returns to step 19005A.

At step 20045A, the smart tray determines if it is in a transit or shipping mode. Again, appropriate pins and/or status register bits may be set to control and determine whether the tray is in this mode. If it is in the shipping mode ("yes"), the program proceeds to step 20050A, wherein non-encrypted data is transmitted and received between the smart tray and shipping/tracking equipment (e.g., a RFID reader device)(not shown). The nonencrypted data can include data such as manufacturer, lot number, number and type of pills, etc. that is not confidential health data. Each tray, among multiple trays in a single RF communication zone, can be detected using the standard of 13.68 megahertz in that zone. This allows various members of the supply and distribution chain including the manufacturer, carrier, distributor and retailer to access that information from a RFID tag or circuitry within each tray and to synchronize and speed up the movement and tracking of each tray from the manufacturer to the end-user. At step 20055A, the program determines if all required or requested data has been transmitted to the shipping/tracking equipment. If so, the process returns to step 20005A.

At step 20060A, the smart tray determines if it is in an inventory mode. In one embodiment, a status register bit is set by a signal from a external device (e.g., a RFID tag reader) to place the tray in inventory mode. Inventory mode accommodates situations where the pharmacist or distributor knows that there will be a continuing demand for trays containing a standard number of a specified pill. For example, many diabetics need to take two pills each day so there will be a continuing demand for trays loaded with 60 pills to provide a 30 day supply. Those trays would be prepackaged and maintained in inventory at the pharmacist or other distributor. If the tray is in Inventory Mode and activated by a standard RFID reader device (e.g., via an electromagnetic field emitted by the reader), at step 20065A, a strobe light or LED attached to an external surface of the tray is turned on for a predetermined length of time in order to facilitate identification of the tray and ensure that a person looking for the inventory retrieves the right inventory. In one embodiment, the "time out" of the strobe LED circuitry is adjustable and is set to provide a 25 second lead time, for example. At step 20070A, the program determines if the "time out" period has expired and/or whether all desired inventory data has been transmitted to a reader device. If yes, the program returns to step 20005A.

At step 20085A, the program stores all error codes corresponding to errors that occurred during any of the operations described above. For example, if information transmitted or received by the smart tray is corrupted, or the tray is not functioning properly, or was not loaded properly into a dispensing machine, or the color of the pill does not match an indicated color, or any other predefined condition occurs, such condition can be designated to generate a pre-specified error code. If an error was detected, then at step 20085A the program identifies a proper error code and stores the error code in memory within the tray. The program then returns to step 20005A.

In one embodiment, as described below with reference to FIG. 20B, any error codes stored within memory of the tray are handled at the time the tray is inserted into a dispensing machine. However, it is understood that in other embodiments, such errors may be addressed when the tray is in a loading machine or communicatively coupled to an external device (e.g., an RFID reader).

FIG. 20B illustrates a flow chart for the In_Dispenser Subroutine called at step 20040A (FIG. 20A), in accordance with one embodiment of the invention. At step 20250B, it is determined whether the tray was previously inserted and removed from the dispenser. It is important to determine if the tray has been aborted or recalled due to cancellation of medication, malfunctioning of the tray, or any other reason. If so, the tray should not be reinstalled into the dispenser without proper authorization and precautions.

If the tray had not previously been in a dispenser machine ("no" at 20250B), then at step 20255B, the subroutine determines if the tray has been designated for the dispenser into which it is being inserted. If the tray belongs to the particular dispenser into which it is being inserted, ("yes" at 20255B), the subroutine jumps to point S1, which is the beginning of the subroutine illustrated in FIG. 20C.

If the tray does not belong to the dispenser into which it is being inserted, ("no" at 20255B), at step 20260B, an email and/or page is sent to an appropriate pharmacist or caregiver to alert that person. As described above, in one embodiment, the dispenser is connected to a main server via a computer network. Via this connection and appropriate software residing within the dispenser and main server, an e-mail and/or page can be sent to a designated pharmacist and/or caregiver to alert them that the tray is being inserted into the wrong dispenser. In one embodiment, the dispenser or tray itself can display a warning, either via it's optic display on the tray or a display screen coupled to the dispenser, for example, to inform the person inserting the tray into the dispenser that the tray is not authorized for this particular dispenser. If the tray is still inserted after this warning, an email and/or page can then sent to appropriate personnel.

At step 20265B, an error code number corresponding to the tray being inserted into an unauthorized dispenser is determined and a warning or instruction is provided on a display of the dispenser to not insert or remove the smart tray from the dispenser. At step 20270B, data concerning this error is uploaded to the main server coupled to the dispenser via a computer network or electromagnetic communication network. At step 20275B, the tray is disabled so that no medication can be dispensed or information transferred from the tray. In one embodiment, the error code stored in the tray will prevent the dispenser from engaging the tray and/or communicating with the tray. This is one of the many safety features of the tray and overall system.

Going back to step 20250B, if the tray had previously been in the dispenser ("yes" at 20250B), the subroutine proceeds to step 20285B to determine if there was a previous error associated with the tray. If there was an error ("yes" at 20285B), at step 20290B, all the information in the tray is shared with the dispenser. If there was no error ("no" at 20285B), there is no need to share that information from the tray to the dispenser because it is already there.

At step 20295B, the process determines if the data in the tray is older than 6 hours, for example. It is desirable to ensure that all data is current and that there has not been some recent change such as a change in the prescription dosage, discontinuation of the medication due to side effects, interaction with other medications, FDA recall, etc. To make sure that the information is always current, in one embodiment, information is downloaded every 6 hours from the main server. This time period is adjustable depending on the desired frequency of checking for updates.

If the data is older than 6 hours ("yes" at 20295B), at step 20300B, a communication link is established between the dispenser and the main server in order to download all microinstructions and other desired data to be inserted in the tray. If the data is not older than 6 hours ("no" at 20295B), then the process proceeds to step 20305B, which determines if the dispenser is downloading data to the tray. If the dispenser is downloading data ("yes" at 20305B), then as soon as that downloading is completed, at step 20310B, a service dispenser request is initiated wherein the dispenser verifies that all the sensors and the engagement and sorting mechanisms of the smart tray are functioning properly. After that check or if the dispenser was not downloading any data ("no" at 20305B), the process proceeds to step 20315B which performs a maintenance check on the smart tray. This maintenance check can be more comprehensive than the service request described above and can check such things as how old the tray is, how old the pills are, whether there have been any status change regarding the pills (e.g., a recall) or the patients designated to receive the medication, etc. Thus, the dispenser is capable of performing a totally automatic maintenance verification of the smart tray.

At step 20320B, the program determines if there is a smart tray maintenance problem. If the answer is "yes" and there is a maintenance problem, an error code corresponding to the problem is identified and stored. This error code is then uploaded to the main server. This enables the automatic and immediate scheduling of service calls without intervention of any person because the system can automatically generate an alert describing the problem, the location of the equipment and the contact persons at the end user that need to be notified.

Next, at step 20330B, the program determines if the smart tray is in dispensing mode. If it is in dispensing mode ("yes" at 20330B), at step 20335B, all instructions including any voice and text data to tell the end user how to take the medication is shared from the tray to the dispenser. In one embodiment, also shared are side effect voice templates to inform the patient of side effects. Alternatively, text and graphics may be provided to a display coupled to the dispenser to inform the patient of side effects or other desired information. In one embodiment, for hearing impaired patients, the dispenser also includes a vibrator and voice recognition software to convert voice data into text that may be displayed on the display screen. For example, blind or deaf patients may be able to receive signals from the dispenser based on predefined and distinct vibration patterns. Such vibrators are well known in the art and are used in cell phones, for example.

At step 20340B, the tray also shares with the dispenser quality control data such as drug interaction data to verify no adverse reactions with drugs contained in other smart trays in the dispenser. This interaction data may further include information pertaining to interaction with certain foods, vitamins or herbal remedies that would be detrimental to the patient. At step 20345B, the smart tray receives from the dispenser any inventory updates and side effect data with a date stamp. Thus, there is a two-way communication protocol established between the smart tray and the dispensing equipment such that both the tray and the dispensing equipment have the most up-to-date information.

At step 20350B, the program asks if the smart tray is being returned for credit. If yes, at step 20355B, the main server is updated with the information that there is a request for credit for the tray and all operations of the tray are stopped and/or the tray is disabled. So the tray can be removed and the inventory information in the tray will be accurate since it cannot dispense anymore. This provides accurate inventory control.

At step 20360B, the program determines if reordering has been completed for medicaments contained in the tray. If the answer is "yes", the subroutine ends at step 20375B and returns to the main program (FIG. 20A). If the answer is "no," at step 20365B, the subroutine determines if the inventory in the tray is equal or below a specified reorder level. That reorder level will depend upon the number of pills to be taken each day, the expected lead time to get the new tray delivered to the end user and some additional time to provide a margin of safety.

If the inventory level in the tray is greater than the specified reorder level ("no" at 20365B), the subroutine ends at step 20375B and returns to the main program (FIG. 20A). If the inventory level in the tray is less than or equal to the specified reorder level ("yes" at 20365B), at step 20370B, the Re_Order Subroutine is called. As described in further detail below with respect to FIG. 20D, this will cause dispenser to send a re-order request to the main server. After completing the Re_Order Subroutine, the In_Dispenser subroutine ends at step 20375B.

FIG. 20C is a continuation of the In_Dispenser Subroutine that begins in FIG. 20B. At step 20255B (FIG. 2B) if the tray is determined to belong to the dispenser, then there is a call to subroutine S1, which deals with the situation when the tray was not previously in a dispenser and is now placed into a proper dispenser. As shown in FIG. 20C, the subroutine S1 begins at step 20380C, which determines if the tray was previously discarded. If it was previously discarded ("yes" at 20380C), at step 20385C, an appropriate error code is set and an error message is displayed to an appropriate end user. At step 20390C, data pertaining to the error is uploaded to the dispenser and ultimately to the main server. At step 20395C, all further operations pertaining to the discarded tray are stopped and/or the tray is disabled.

If the tray was not previously discarded ("no" at 20380C), at step 20400C, it is determined whether the tray is being removed from the dispenser. If yes, then at step 20397C, the Discarded_Stray Subroutine is called. This subroutine is described in further detail below with reference to FIG. 20E. If the tray is not being removed from the dispenser ("no" at 20396C), than step 20400C determines if all necessary data and microinstructions were loaded into the smart tray memory when it was loaded with the medications. If the data and microinstructions were not loaded ("no" at 20400C), at step 20405B, a communications link is established between the dispenser and the main server and all the necessary data and microinstructions are downloaded from the main server to the dispenser and to the tray. The main server knows which data and microinstructions to send by a unique identification code associated with the smart tray. This unique identification code may be stored in a memory within the smart tray or provided on an external surface or label affixed to the smart tray in a human and/or machine readable format. Thus, even if desired data is not stored in the smart tray, an external device (e.g., a dispensing machine, a loading machine, or reader at a pharmacy) may be able to retrieve the data from a server computer via an electronic communication network based on the unique identification code. Such data can include, for example, all medical data pertaining to the medicaments and patients, quality control data, microinstructions for dispensing equipment etc.

At step 20410C, the program determines if the data is older than 6 hours. This step and the following step 20415C function the same as steps 20295B and 20300B, respectively, described above with respect to FIG. 20B.

At step 20420C, the process determines whether the dispenser is a commercial dispenser or not. A commercial dispenser would be a dispenser used in a physician's office, pharmacy or other location where the dispenser is dispensing medications into a bottle that will be given to the patient. A noncommercial dispenser is one that will be used directly by the patient or caregiver to manage the medication regimen of the patient. If this dispenser is a commercial dispenser ("yes" at 20420C), then the subroutine proceeds directly to step 20445C (discussed below).

If this dispenser is not a commercial dispenser ("no" at 20420C), then at step 20425C, the subroutine determines if there is any drug interaction with medications in the other smart trays in the dispenser. If there are no drug interactions with the medications in the other smart trays in the dispenser ("no" at 20425C), the process proceeds directly to step 20445C (discussed below).

If there is a drug interaction with a medication in another smart tray in the dispenser ("yes" at 20425C), at step 20430C, a corresponding error code is generated and stored in the smart tray. Additionally, the error code information is sent to the dispenser for display on the display of the dispenser for the end user to see. At step 20435C, the error code information is also uploaded to the main server so that proper action can be taken by an employee or administrator of the overall system. Next, at step 20440C, all operations pertaining to the tray are halted and/or the tray is disabled such that it can no longer dispense medicaments. At this point, the dispenser can wait for instructions from the main server or a designated doctor, caregiver or other official. For example, an authorized physician at the dispenser site can enter an appropriate authorization code and thereafter enable the tray and/or dispenser to dispense medicines and remove or update the error code information. It is appreciated that many different scenarios, criteria and methods of disabling and enabling the tray and/or dispenser are possible and could be readily implemented by those of ordinary skill in the art, without undue experimentation.

At step 20445C, the subroutine decrypts all information and shares all necessary data and microinstructions from the tray to the dispenser. It is appreciated that the encryption and decryption of information performed by the present invention allows for compliance with Health Insurance Portability and Accountability Act (HIPAA) privacy laws. Thus, the dispenser is automatically provided with all necessary information concerning the operation and quality control of the tray.

At step 20450C, the dispenser communicates with the main server and tells it that the smart tray has been received and has been installed and is functioning properly.

At step 20455C, the subroutine sets all proper variables in the smart tray for error flags, alarms, and other instruction parameters and direction of process flow parameters depending on particular error codes as may be designed by a programmer for a particular application. For example, an FDA recall may trigger a certain error code resulting in a pre-specified process flow.

At step 20460C, subroutine S1 ends and returns to the main program (FIG. 20A) at step 20005A.

FIG. 20D illustrates a flow chart for the Reorder Subroutine called at step 20370B (FIG. 20B), in accordance with one embodiment of the invention. If the inventory in the Tray goes below a predetermined number of pills, the tray or dispenser will automatically send a reorder request to the main server. Of course, the main server is programmed to alert an appropriate person (e.g., send an automatic email, provide a message on a display, etc.) so as to ultimately communicate to a designated pharmacist or medicine distributor that a new tray is being requested. The main server can also facilitate making arrangements for payment.

Because there can be errors in communications with the main server, at step 20100D, a permitted number of communication retries is set and initiated (as necessary) to accommodate such possible communication errors. In one embodiment, up to 8 retries are performed before the communication is terminated and it is reported as an alarm back to the dispensing machine. At step 20105D, the subroutine determines if the communication try was the last one. If it was the last try and it failed, at step 20110D, an error code is set and stored in the tray and a corresponding message is displayed on the dispenser's display. The subroutine then ends at step 20115D and returns to the main program (FIG. 20A).

In addition to the number of tries, a "time out" timer is also set to control the length of time required for each try to establish a connection with the main server. This "time out" timer is set/reset at step 20120D. If a connection with the main server is established, at step 20125D, the tray or dispenser reorders the appropriate prescription(s). At step 20130D, it is determined if the order was acknowledged by the pharmacy or distributor with which the order was placed at 20125B. If it was acknowledged ("yes"), at step 20135D, the main server assists in processing the order, making payments and sending notification of the processed order and payment. At step 20137D, a memory flag for the tray is cleared and an error flag is reset to 0, indicating that all pending re-orders have been taken care of. At this point, the re-order subroutine returns to the main program (FIG. 20A).

If at step 20130D, the order was not acknowledged, then at step 20140D, it is determined whether payment information is needed. For example, if credit card information from the payer is not valid (e.g. the card has expired, been reported stolen, over its credit limit, incorrect information, etc.), this would prevent the reorder transaction from being completed. If additional information is needed, at step 20145D, the subroutine sends an e-mail and/or page to the patient or its designated caregivers to inform them that additional payment information is needed. Next, at step 20150D, appropriate smart tray error reporting codes are stored in the tray sent to the display of the dispenser for reporting the need for additional payment information. At step 20153D, it is determined whether the prescription needs to be renewed. If the prescription does not need to be renewed, the subroutine terminates and returns to the main program at step 20005A (FIG. 20A).

Alternatively, if at step 20140D, it is determined that payment information is not needed, at step 20160D, it is determined whether the prescription needs to be renewed. For example, if the prescription was for four months and one refill, the current reorder might exceed that limit and the patient would need to get a renewed prescription from the doctor. If at either step 20153D or 20160D it is determined that the prescription needs to be renewed, the process proceeds to step 20165D where an e-mail and/or a page is sent to a designated doctor and/or all the designated caregivers to the patient to inform them that the prescription needs to be renewed. Next, at step 20170D, appropriate error reporting codes are set and stored in the smart tray and a message describing the need for prescription renewal is displayed on the dispenser's display. Thereafter, at step 20175D, the subroutine returns to the main program (FIG. 20A).

At step 20180D, the subroutine determines if the re-order process has "timed out." In order to avoid unreasonable delays, if a predetermined time period has elapsed, the re-order attempt is determined to have failed and, at step 20185D, the number of retries is decremented by 1 and the process returns to step 20105D. If the time out period has not expired, the subroutine returns to step 20130D and continues to wait for an order acknowledgement.

FIG. 20E illustrates a flow chart for the Discarded_Stray Subroutine which is called at step 20397C (FIG. 20C) before the tray is removed from the Dispenser. There may be several reasons why the tray is being removed, with different actions to be done to the information stored in the tray depending on the reason for the tray's removal. For example, the tray might be removed because it is empty, in which case the patient information contained in the tray's RFID tag will need to be deleted. Or the tray might be removed to be placed back in inventory or returned for a credit. This Subroutine will make those determinations and take the appropriate action.

The Discarded_Stray Subroutine starts at 20190E and immediately proceeds to step 20192E, where it determines if the smart tray is being removed only temporarily. For example, a smart tray might be temporarily removed to replace it with a different smart tray containing different medications prescribed for a limited duration and then later the original smart tray is reinserted back into the dispenser. On the other hand, a smart tray might be removed permanently because it is empty or the patient's medication regimen has been permanently altered. Appropriate codes received from the main server, or entered by an authorized physician or caregiver can be utilized to determine if the removal of the tray is only temporary, or the dosage of the medication is changed or should be completely aborted, or whether the tray should be discarded or returned for credit.

If the smart tray is being removed for a temporary reason ("Yes" at 20192E), then the function at 20194E will set the error number in the Smart Tray. The subroutine then "jumps" to a point designated by "E100" where at step 20214E, information pertaining to the temporary removal of the original smart tray and all required data and information pertaining to the replacement tray (if any) is uploaded to the main server and dispenser (where it can be displayed on the dispenser's display screen for the user to view). At step 20216E the subroutine stops all further operations with respect to the original smart tray. The subroutine then returns to the main program.

If the smart tray is not being removed for a temporary reason ("No" at 20192E), the subroutine proceeds to step 20198E where it determines if the smart tray is being returned for credit. That would occur in several circumstances such as an FDA recall or where a patient died or his or her medication regimen changed (e.g. patient was experiencing side effects or got a different prescription that caused an older prescription to be terminated) or the patient had a smart tray containing medications that were no longer required. Because the smart trays are hermetically sealed and an accurate inventory of the pills in the smart tray is maintained, along with information such as the lot number, expiration date, etc. It might be possible to return that smart tray with those unused pills for credit.

If the smart tray is being returned for credit ("Yes" at 20198E), then the function at step 20200E will set the error number in the smart tray. The program then proceeds to E100 where at step 20214E information concerning the return of the tray for credit is uploaded to the server and dispenser (where it can be displayed on the dispenser's display screen for the user to view. At step 20216E all further operation pertaining to that smart tray are stopped. The smart tray can then be removed and the inventory information in the smart tray will be accurate since it cannot dispense any more pills, thereby providing exact inventory control.

If the smart tray is not being returned for credit ("No" at 20198E), the subroutine proceeds to step 20204E to determine if the smart tray is being removed from operation. That could result from the same factors discussed above with regard to 20198E (e.g. FDA recall, patient death or medication regimen change) where the smart tray is to be removed without being be returned for credit. If the smart tray is being aborted ("Yes" at 20204E), then the function at step 20208E will set the error number in the Smart Tray. It will then proceed to point E100 in the flow chart where at step 20214E corresponding information is uploaded to the server and dispenser (where it can be displayed on the dispenser's display screen for the user to view. At step 20216E, the subroutine will then stop further operations pertaining to that smart tray.

If the smart tray is not being aborted ("No" at 20204E), then we proceed to point E50 in the flow chart. Point E50 starts at step 20218E to determine if a reorder request was sent for a new smart tray. It will verify if a previous reorder of the medication has been sent out before removing that smart tray from the dispensing equipment. If the reorder had not been sent ("No" at 20218E), it will go to 20226E which calls the Re_Order Subroutine, as described above with respect to FIG. 20D, in accordance with one embodiment of the invention. If the reorder was sent out ("Yes" at 20218E), at step 20222E, the subroutine determines if the information stored in the memory in the smart tray was previously cleared. If the information had been cleared ("Yes" at 20222E), at step 20224E, the subroutine terminates and returns to the program that called it. But if the information had not been cleared ("No" at 20222E), it goes to step 20226E which calls the Re_Order Subroutine described above with respect to FIG. 20D.

After the Re_Order Subroutine is completed, at step 20228E, the subroutine reads the memory of the smart tray and determines if there was an error during the reordering process (as would be indicated by an error code stored in the smart tray memory). If it is determined there was no error ("No" at 20228E), then the subroutine proceeds directly to step 20232E. If there was an error ("Yes" at 20228E), at step 20230E, the subroutine calls the In_Dispenser Subroutine described above with respect to FIGS. 20B and 20C. During the In_Dispenser Subroutine, those errors will be displayed on the dispenser display and uploaded to the main server. After the In_Dispenser Subroutine is completed, the Discarded_Stray Subroutine will proceed to step 20232E.

At 20232E it determines if there was an "error" during one of the previous subroutines. If there is no error ("No" at 20232E) then the subroutine proceeds to step 20234E and returns to the calling program or subroutine. If there was an error ("Yes" at 20232E) this indicates that the smart tray is to be removed to be discarded (i.e., thrown away in the garbage) rather than being put back in inventory and the subroutine proceeds directly to step 20236E. At that point, all variables indicating status of the tray (i.e., discarded) and all personal information is erased to protect the privacy of the end user of the smart tray. This is done to ensure that, even if the smart tray has been discarded, no other person can invade the personal data of the patient or the end user. Thus, in one embodiment, the smart tray is designed to comply with the HIPPA privacy standard. At step 20240E, the subroutine ends and returns to the calling program or subroutine.

As described above, various exemplary functions of the smart tray in conjunction with a dispenser machine and a main server, communicatively coupled to the dispenser, have been described. It is understood by those skilled in the art that these various functions can be implemented via software, firmware and/or hardware residing in the tray, dispensing machine and main server to perform and coordinate the functionality and communication protocols described above. Such software, firmware and/or hardware, and various modifications thereof, can be designed and implemented by those of ordinary skill in the art without undue experimentation.

Figure 21:
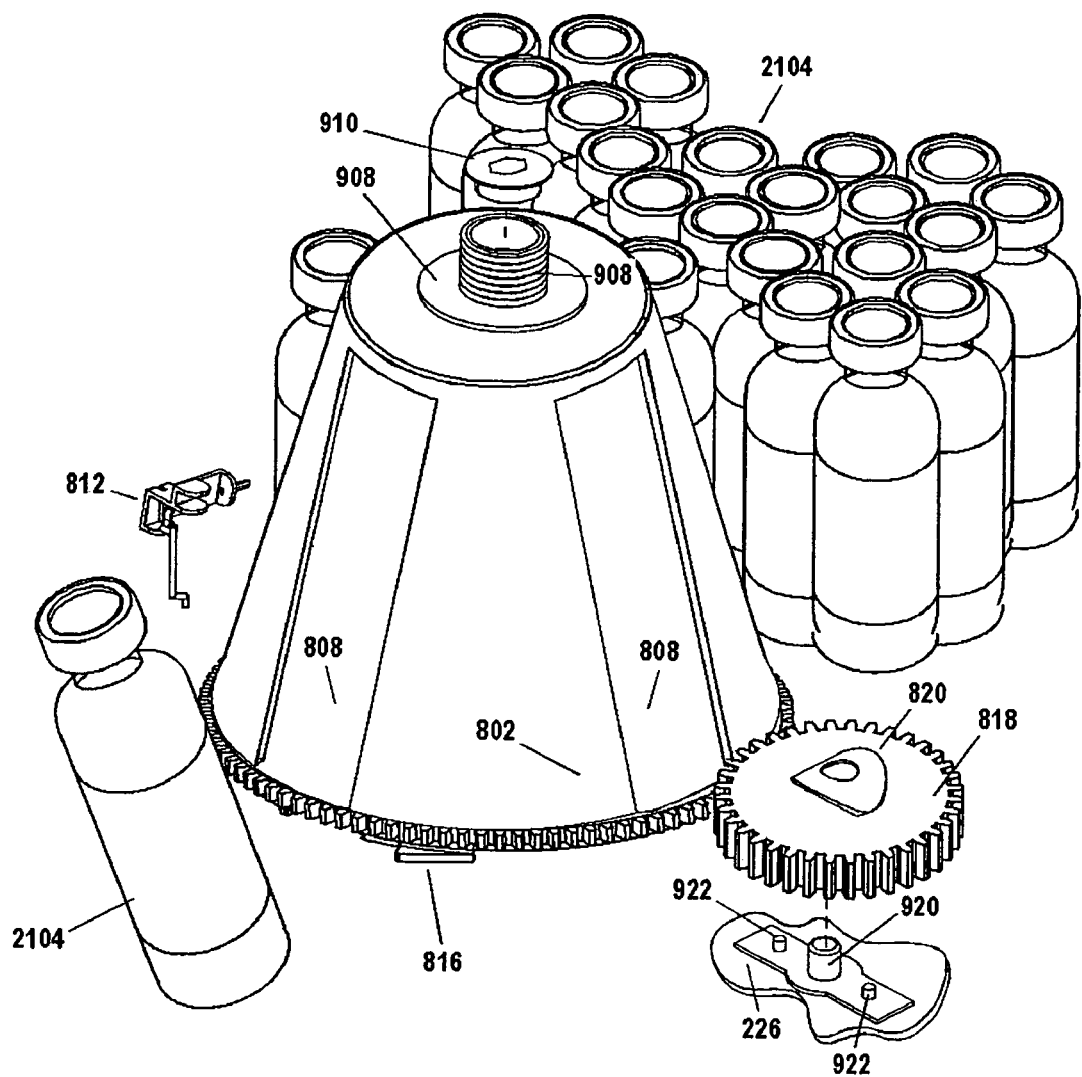
FIG. 21 provides a perspective view of a tray for sorting and dispensing bottles or containers of medicaments, in accordance with an alternative embodiment of the invention.

FIG. 21 illustrates a perspective view of an alternative embodiment of the invention. This embodiment of the invention is used to dispense uniform sized bottles 2104 filled in tray 100. Conical disk assembly 802 is modified to accommodate bottles 2104 in grooves 808 rather than individual medicament units (e.g., pills or tablets). In this embodiment, the height of tray 100 is increased (e.g., to three and a half inches) in order to accommodate bottles 2104. Such modifications to the conical disk assembly 802 and tray 100 can easily be made by those of ordinary skill in the art, without undue experimentation, so as to comport within the teachings of the present invention.

Thus, as illustrated by the exemplary embodiments described above, the smart dispensing trays of the invention, and associated methods and systems, have several advantages over existing automated medicaments dispensing systems. The smart dispensing tray provides an accurate, low cost, compact and high storage capacity medicaments dispensing mechanism. The tray has a precise central adjustment mechanism which allows for automated filling at high speed. Further the invention allows remote and automatic detection of counterfeit medication. The tray enclosure has a hermetically sealing mechanism that permits the return of unused medications to their distributors for a refund. The tray is further capable of automatically providing medical information data for use during filling, transport, and dispensing of medicaments. Additionally, other desired information about the medicaments, intended patients, authorized caregivers, etc. may also be provided by the tray. The tray can also provide information regarding the side effects of one or more medications. This information can be updated by feedback received from patients and caregivers. In some embodiments, this information is automatically downloaded to processing devices (e.g., RFID tag readers and/or computer memory) for use by pharmacist, hospital, patient, caregiver, shipper, etc. Further the tray provides a means for communicating over a computer network and hence may be operated and monitored via a remote network computer.

While various embodiments of the invention have been illustrated and described, those of ordinary skill in the art will appreciate that the above descriptions of the embodiments are exemplary only and that the invention may be practiced with modifications or variations of the devices and techniques disclosed above. Those of ordinary skill in the art will know, or be able to ascertain using no more than routine experimentation, many equivalents to the specific embodiments of the invention described herein. Such modifications, variations and equivalents are contemplated to be within the spirit and scope of the present invention as set forth in the claims below.

What is claimed is:

1. A medicaments dispensing container for containing a plurality of medicament units, comprising:
   a housing configured to contain the plurality of medicament units;
   an information storage device configured to maintain information pertaining to the plurality of medicament units in the medicaments dispensing container, wherein the information pertaining to the plurality of medicament units comprises inventory information for the plurality of medicament units in the medicaments dispensing container, wherein said information pertaining to the plurality of medicament units in the medicaments dispensing container is automatically communicated to an insurance agency to facilitate automatic claim processing; and
   a communication device communicatively coupled to the information storage device and configured to allow communication of the inventory information between the information storage device and an external computing device to facilitate automated inventory tracking for the plurality of medicament units.

2. The medicaments dispensing container of claim 1, further comprising an indicator communicatively coupled to the information storage device and configured to be activated when a quantity of medicament units remaining in the medicaments dispensing container reaches a predetermined amount.

3. The medicaments dispensing container of claim 2, wherein said indicator comprises at least one of a luminous indicator, an audible indicator and a radio frequency indicator.

4. The medicaments dispensing container of claim 2, further comprising an indicator communicatively coupled to the information storage device and configured to be activated upon a determination by the inventory control logic that the quantity of medicament units remaining in the medicaments dispensing container has reached a predetermined amount.

5. The medicaments dispensing container of claim 1, wherein said communication device is at least one of a wired and a wireless communication device.

6. A medicaments dispensing container for containing a plurality of medicament units, comprising:
   an information storage device configured to maintain information pertaining to the plurality of medicament units in the medicaments dispensing container, wherein the information pertaining to the plurality of medicament units comprise inventory information for the plurality of medicament units in the medicaments dispensing container; and
   logic configured to update the inventory information, determine whether to reorder additional medicament units based on the updated inventory information, wherein said logic is configured to send a signal to an external computing device to reorder additional medicament units, and wherein said logic is further configured to cause a communication to be sent to at least one of a patient and a caregiver if it is determined that the additional medicament units are to be reordered.

7. The medicaments dispensing container of claim 6, wherein said logic is further configured to process payment information for the reorder.

8. The medicaments dispensing container of claim 6, wherein said logic is further configured to cause a communication to be sent to at least one of a patient and a caregiver if payment information is needed for the reorder.

9. The medicaments dispensing container of claim 6, wherein the information pertaining to said plurality of medicament units in the medicaments dispensing container comprises patient information and the logic is further configured to remove the patient information from the information storage device when there are no more medicament units in the medicaments dispensing container.

10. The medicaments dispensing container of claim 6, wherein said logic is further configured to send a signal to the external computing device indicating a quantity of medicament units remaining in the medicaments dispensing container.

11. The medicaments dispensing container of claim 6, wherein said logic is further configured to send a signal to the external computing device indicating a quantity of medicament units remaining in the medicaments dispensing container when the updated inventory level reaches a predetermined amount.

12. The medicaments dispensing container of claim 6, wherein said logic is further configured to determine whether a patient for whom the medicament units in the medicaments dispensing container were prescribed is authorized to receive a refill of a prescription.

13. The medicaments dispensing container of claim 6, wherein said information storage device is further configured to receive said information pertaining to said plurality of medicament units in the medicaments dispensing container from medicament loading equipment.

14. The medicaments dispensing container of claim 6, wherein said external computing device comprises a computing device associated with loading equipment and said communication device is configured to allow communication of at least one of a quantity of medicament units, a type of medicament units, patient information, and transit information between the information storage device and the external computing device.

15. The medicaments dispensing container of claim 6, wherein said external computing device comprises at least one of a loading equipment computing device, a shipping equipment computing device, a computing device of a dispenser, and a server.

16. The medicaments dispensing container of claim 6, wherein said information pertaining to said plurality of medicament units in the medicaments dispensing container further comprises at least one of a group consisting of patient information, caregiver information, and medicament information.

17. The medicaments dispensing container of claim 16, wherein said external computing device is a server, and further comprising logic configured to retrieve said information pertaining to said plurality of medicament units in the medicaments dispensing container from the server.

18. The medicaments dispensing container of claim 17, wherein said logic comprises logic configured to determine whether said information pertaining to said plurality of medicament units in the medicaments dispensing container is in the information storage device, and to provide an identification code of the medicaments dispensing container to the server.

19. The medicaments dispensing container of claim 16, wherein said medicament information comprises at least one of a group consisting of: an intended use for the medicament; drug interaction precautions pertaining to the medicament units in the medicaments dispensing container; side effects of the medicament units in the medicaments dispensing container; an identification of the medicament units in the medicaments dispensing container; the dosage the medicament units in the medicaments dispensing container; the date the medicament units were packaged in the medicaments dispensing container; a color image of the medicament units in the medicaments dispensing container; inventory data regarding the medicament units in the medicaments dispensing container; an expiration date of the medicament units in the medicaments dispensing container; drug interaction information regarding the medicament units in the medicaments dispensing container; supplement interaction information regarding the medicament units in the medicaments dispensing container; manufacture information regarding the medicament units in the medicaments dispensing container; a lot number for regarding the medicament units in the medicaments dispensing container; and recall information regarding the medicament units in the medicaments dispensing container.

20. The medicaments dispensing container of claim 19, further comprising inventory update logic, communicatively coupled to said information storage device and configured to determine a quantity of medicament units dispensed from the medicaments dispensing container; and to determine whether to reorder additional medicament units based on said medicament information when a quantity of medicament units remaining in the medicaments dispensing container reaches a predetermined level.

21. The medicaments dispensing container of claim 16, wherein said patient information comprises at least one of a group consisting of: an identification of a recipient of the medicament units in the medicaments dispensing container; a number of refills authorized for the medicament units in the medicaments dispensing container; an authorized caregiver for said patient; patient insurance information; payment information; patient medical history; patient vital signs; patient reaction to the medicament units in the medicaments dispensing container; instructions for administering the medicament units in the medicaments dispensing container; patient contact information; and patient biometric information.

22. The medicaments dispensing container of claim 21, further comprising inventory update logic, communicatively coupled to said information storage device and configured to determine a quantity of medicament units dispensed from the medicaments dispensing container; and to determine whether to reorder medicament units based on said patient information when a quantity of medicament units remaining in the medicaments dispensing container reaches a predetermined level.

23. The medicaments dispensing container of claim 6, wherein said information storage device is further configured to accept updates from a dispensing machine by way of the communication device.

24. The medicaments dispensing container of claim 21, wherein said information storage device is further configured to accept said updates, wherein said updates are entered by a caregiver.

25. A medicaments dispensing container for containing a plurality of medicament units, comprising:
an information storage device configured to maintain information pertaining to the plurality of medicament units in the medicaments dispensing container, wherein the information pertaining to the plurality of medicament units comprise inventory information for the plurality of medicament units in the medicaments dispensing container; and logic configured to update the inventory information, determine whether to reorder additional medicament units based on the updated inventory information, and send a signal to an external computing device to reorder additional medicament units; wherein said logic is further configured to process payment information for the reorder.

26. A medicaments dispensing container for containing a plurality of medicament units, comprising:

an information storage device configured to maintain information pertaining to the plurality of medicament units in the medicaments dispensing container, wherein the information pertaining to the plurality of medicament units comprise inventory information for the plurality of medicament units in the medicaments dispensing container; and logic configured to update the inventory information, determine whether to reorder additional medicament units based on the updated inventory information, and send a signal to an external computing device to reorder additional medicament units, wherein said logic is further configured to cause a communication to be sent to at least one of a patient and a caregiver if payment information is needed for the reorder.

27. A medicaments dispensing container for containing a plurality of medicament units, comprising:

an information storage device configured to maintain information pertaining to the plurality of medicament units in the medicaments dispensing container, wherein the information pertaining to the plurality of medicament units comprise inventory information for the plurality of medicament units in the medicaments dispensing container; and logic configured to update the inventory information, determine whether to reorder additional medicament units based on the updated inventory information, and send a signal to an external computing device to reorder additional medicament units, wherein the information pertaining to said plurality of medicament units in the medicaments dispensing container comprises patient information and the logic is further configured to remove the patient information from the information storage device when there are no more medicament units in the medicaments dispensing container.

28. A medicaments dispensing container for containing a plurality of medicament units, comprising:

a housing configured to contain the plurality of medicament units;

an information storage device configured to maintain information pertaining to the plurality of medicament units in the medicaments dispensing container, wherein the information pertaining to the plurality of medicament units comprises inventory information; and logic contained within the housing, communicatively coupled to the information storage device and configured to sense a quantity of medicament units dispensed from the medicaments dispensing container and update the inventory information to reflect the quantity of medicament units dispensed from the medicaments dispensing container, thereby to maintain an updated inventory of medicament units remaining in the medicaments dispensing container, wherein the logic is configured to determine whether to order additional medicament units based on the updated inventory information, wherein said medicament units in the medicaments dispensing container are provided under a prescription, and wherein the logic is further configured to determine a number of refills remaining under the prescription.

29. A medicaments dispensing container for containing a plurality of medicament units, comprising:

a housing configured to contain the plurality of medicament units;

an information storage device configured to maintain information pertaining to the plurality of medicament units in the medicaments dispensing container, wherein the information pertaining to the plurality of medicament units comprises inventory information for the plurality of medicament units in the medicaments dispensing container;

logic configured to update the inventory information and determine whether to reorder additional medicament units based on the updated inventory information, wherein said logic is further configured to send a signal to an external computing device to reorder additional medicament units, and wherein said logic is further configured to cause a communication to be sent to at least one of a patient and a caregiver if it is determined that the additional medicament units are to be reordered; and a sensor unit contained within the housing and communicatively coupled to the information storage device, wherein the sensor unit is configured to sense a medicament unit being dispensed from the medicaments dispensing container.

30. A medicaments dispensing container for containing a plurality of medicament units, comprising:

a housing configured to contain the plurality of medicament units;

an information storage device configured to maintain information pertaining to the plurality of medicament units in the medicaments dispensing container, wherein the information pertaining to the plurality of medicament units comprises inventory information for the plurality of medicament units in the medicaments dispensing container;

logic configured to update the inventory information and determine whether to reorder additional medicament units based on the updated inventory information, wherein said logic is further configured to send a signal to an external computing device to reorder additional medicament units, and wherein said logic is further configured to process payment information for the reorder; and a sensor unit contained within the housing and communicatively coupled to the information storage device, wherein the sensor unit is configured to sense a medicament unit being dispensed from the medicaments dispensing container.

31. A medicaments dispensing container for containing a plurality of medicament units, comprising:

a housing configured to contain the plurality of medicament units;

an information storage device configured to maintain information pertaining to the plurality of medicament units in the medicaments dispensing container, wherein the information pertaining to the plurality of medicament units comprises inventory information for the plurality of medicament units in the medicaments dispensing container;

logic configured to update the inventory information and determine whether to reorder additional medicament units based on the updated inventory information, wherein said logic is further configured to send a signal to an external computing device to reorder additional medicament units, and wherein said logic is further configured to cause a communication to be sent to at least one of a patient and a caregiver if payment information is needed for the reorder; and a sensor unit contained within the housing and communicatively coupled to the information storage device, wherein the sensor unit is configured to sense a medicament unit being dispensed from the medicaments dispensing container.

32. A medicaments dispensing container for containing a plurality of medicament units, comprising:

a housing configured to contain the plurality of medicament units;

an information storage device configured to maintain information pertaining to the plurality of medicament units in the medicaments dispensing container, wherein the information pertaining to the plurality of medicament units comprises inventory information for the plurality of medicament units in the medicaments dispensing container and patient information;

logic configured to update the inventory information and determine whether to reorder additional medicament units based on the updated inventory information, wherein said logic is further configured to send a signal to an external computing device to reorder additional medicament units, and wherein the logic is further configured to remove the patient information from the information storage device when there are no more medicament units in the medicaments dispensing container; and a sensor unit contained within the housing and communicatively coupled to the information storage device, wherein the sensor unit is configured to sense a medicament unit being dispensed from the medicaments dispensing container.

* * * * *

UNITED STATES PATENT AND TRADEMARK OFFICE
CERTIFICATE OF CORRECTION

PATENT NO. : 7,630,790 B2
APPLICATION NO. : 11/056521
DATED : December 8, 2009
INVENTOR(S) : Handfield et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 534 days.

Signed and Sealed this

Second Day of November, 2010

David J. Kappos
*Director of the United States Patent and Trademark Office*